United States Patent
de Mollerat du Jeu

(10) Patent No.: US 12,152,248 B2
(45) Date of Patent: *Nov. 26, 2024

(54) MEMBRANE-PENETRATING PEPTIDES TO ENHANCED TRANSFECTION AND COMPOSITIONS AND METHODS FOR USING SAME

(71) Applicant: LIFE TECHNOLOGIES CORPORATION, Carlsbad, CA (US)

(72) Inventor: Xavier de Mollerat du Jeu, Encinitas, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 749 days.

This patent is subject to a terminal disclaimer.

(21) Appl. No.: 17/006,629

(22) Filed: Aug. 28, 2020

(65) Prior Publication Data

US 2020/0392537 A1 Dec. 17, 2020

Related U.S. Application Data

(60) Continuation of application No. 15/811,423, filed on Nov. 13, 2017, now Pat. No. 10,760,098, which is a division of application No. 14/569,583, filed on Dec. 12, 2014, now Pat. No. 9,856,496.

(60) Provisional application No. 61/915,429, filed on Dec. 12, 2013.

(51) Int. Cl.
| | |
|---|---|
| *C12N 15/88* | (2006.01) |
| *A61K 47/54* | (2017.01) |
| *A61K 47/64* | (2017.01) |
| *C07K 14/00* | (2006.01) |

(52) U.S. Cl.
CPC ............ *C12N 15/88* (2013.01); *A61K 47/543* (2017.08); *A61K 47/544* (2017.08); *A61K 47/6455* (2017.08); *C07K 14/001* (2013.01); *C12N 2810/40* (2013.01)

(58) Field of Classification Search
None
See application file for complete search history.

(56) References Cited

U.S. PATENT DOCUMENTS

| | | | |
|---|---|---|---|
| 6,664,040 B2 | 12/2003 | Sherman et al. |
| 7,253,143 B1 | 8/2007 | Hanson et al. |
| 7,544,664 B2 | 6/2009 | Avrameas |
| 7,754,678 B2 | 7/2010 | Guo et al. |
| 8,410,045 B2 | 4/2013 | Michel et al. |
| 8,877,725 B2 | 11/2014 | Iversen et al. |
| 9,006,415 B2 | 4/2015 | Ren et al. |
| 9,006,417 B2 | 4/2015 | Yaworski et al. |
| 9,132,198 B2 | 9/2015 | Kelley et al. |
| 9,303,075 B2 | 4/2016 | Brinkmann et al. |
| 9,303,076 B2 | 4/2016 | Brinkmann et al. |
| 9,856,496 B2 | 1/2018 | De et al. |
| 9,865,496 B2 | 1/2018 | Kim et al. |
| 2009/0186802 A1 | 7/2009 | Alluis et al. |
| 2010/0203611 A1 | 8/2010 | Ishizaka et al. |
| 2011/0256088 A1 | 10/2011 | Ren et al. |
| 2013/0108662 A1 | 5/2013 | Brock et al. |
| 2013/0323752 A1 | 12/2013 | Witte-Hoffmann |
| 2015/0211021 A1 | 7/2015 | De |

FOREIGN PATENT DOCUMENTS

| | | |
|---|---|---|
| CN | 102153629 A | 8/2011 |
| CN | 102272142 A | 12/2011 |
| CN | 102573919 A | 7/2012 |
| CN | 103097397 A | 5/2013 |
| EP | 1966240 B1 | 3/2011 |
| JP | 2001517939 A | 10/2001 |
| WO | WO-9840502 A1 | 9/1998 |
| WO | WO-0207773 A2 | 1/2002 |
| WO | WO-02072616 A2 | 9/2002 |
| WO | WO-2007069068 A2 | 6/2007 |
| WO | WO-2010075575 A1 | 7/2010 |
| WO | WO-2011127210 A1 | 10/2011 |

(Continued)

OTHER PUBLICATIONS

Hwang, et al. (1998) "Three-Dimensional Solution Structure of Lactoferricin B, an Antimicrobial Peptide Derived from Bovine Lactoferrin", Biochemistry, 37: 4288-98. (Year: 1998).*
EP20176262.2, Extended European Search Report, dated Feb. 11, 2021, 13 pages.
Cai Y. et al., "The effect of N-or C-terminal alterations of the connector of bacteriophage phi29 DNA packaging motor on procapsid assembly, pRNA binding, and DNA packaging", Nanomedicine vol. 4, No. 1, Mar. 2008, pp. 8-18.
De Coupade, C. et al., "Novel human-derived cell-penetrating peptides for specific subcellular delivery of therapeutic biomolecules", Biochemical Journal, vol. 390, No. 2, Aug. 23, 2005, pp. 407-418.
Foged C., et al., "Cell-Penetrating Peptides for Drug Delivery across Membrane Barriers", Expert Opinion in Drug Delivery, Jan. 2008, vol. 5(1), pp. 105-117.

(Continued)

*Primary Examiner* — Robert M Kelly
(74) *Attorney, Agent, or Firm* — Brigitte Hajos

(57) ABSTRACT

The present invention is directed to non-naturally occurring peptides containing a membrane-penetrating amino acid sequence and further at least one polycationic moiety or peptide sequence. The peptides are suitable for use in delivery a cargo to the interior of a cell. Suitable cargo includes nucleic acid molecules (including DNA, RNA or PNA), polypeptides, or other biologically active molecules. The present invention is further directed to transfection complexes containing the non-naturally occurring peptides of the present invention in non-covalent association with at least one cationic lipid and a cargo to be delivered to the interior of a cell. The invention further relates to methods for the preparation and use of the non-naturally occurring peptides for the formation of transfection complexes and the delivery of a cargo to the interior of a cell in culture, an animal or a human. The invention also relates to compositions and kits useful for transfecting cells.

20 Claims, 14 Drawing Sheets

Specification includes a Sequence Listing.

(56) References Cited

FOREIGN PATENT DOCUMENTS

WO     WO-2011026641 A9     11/2011
WO     WO-2013138795 A1     9/2013

OTHER PUBLICATIONS

Kim, et al., "Mammalian cell transfection: the present and the future", Analytical and Bioanalytical Chemistry. vol. 397, 2010, pp. 3173-3178.

PCT/US2014/070176, "International Search Report and Written Opinion dated Apr. 29, 2015", Apr. 29, 2015, 14 Pages.

Thermo Fisher Scientific, "Factors Influencing Transfection Efficiency", https://www.thermofisher.com/us/en/home/references/gibco-cell-culture-basics/transfection-basics/factors-influencing-transfection-efficiency.html), No Journal, No Volume, No Issue, Author Unknown, Publisher: Thermo Fisher Scientific, Green Island, NY, 2014, 3 pages.

\* cited by examiner

MEMBRANE-PENETRATING PEPTIDES TO ENHANCED TRANSFECTION AND COMPOSITIONS AND METHODS FOR USING SAME

CROSS-REFERENCE TO RELATED APPLICATIONS

This application is a continuation of and claims the right of priority under 35 U.S.C. § 120 to U.S. application Ser. No. 15/811,423, filed on Nov. 13, 2017, now U.S. Pat. No. 10,760,098, which is a divisional of U.S. application Ser. No. 14/569,583, filed Dec. 12, 2014, now U.S. Pat. No. 9,856,496, which claims the right of priority under 35 U.S.C. § 119(e) to U.S. Provisional Application Ser. No. 61/915,429, filed Dec. 12, 2013. The aforementioned applications are commonly owned with the present application and the entire contents thereof are hereby expressly incorporated by reference in their entirety as though fully set forth herein.

SEQUENCE LISTING

The instant application contains a Sequence Listing which has been submitted electronically in ASCII format and is hereby incorporated by reference in its entirety. Said ASCII copy, created on Mar. 3, 2015, is named LT00804_SL.txt and is 35,579 bytes in size.

FIELD OF THE INVENTION

The present invention generally relates to the fields of transfection and cell culture. In particular, the invention provides peptides which are suitable for use as a cell-penetrating peptide, transfection complexes containing the peptides and use thereof for the intracellular delivery of cargo.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND

Lipid aggregates such as liposomes have been found to be useful as delivery agents to introduce macromolecules, such as DNA, RNA, proteins, and small chemical compounds such as small molecules or pharmaceutically active molecules, to cells and tissues in laboratory and clinical research settings. In particular, lipid aggregates comprising cationic lipid components have been shown to be especially effective for delivering anionic molecules to cells. In part, the effectiveness of cationic lipids, and positively charged complexes formed with cationic lipids, is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA and RNA are known to be effective agents for efficient transfection of target cells.

The structure of various types of lipid aggregates varies, depending on the composition and method of forming the aggregate. Such aggregates include liposomes, unilamellar vesicles, multilameller vesicles, micelles and the like, having particular sizes in the nanometer to micrometer range. Methods of making lipid aggregates are generally known in the art. The main drawback to use of conventional phospholipid containing liposomes for delivery is the liposome composition has a net negative charge which is not attracted to the negatively charged cell surface. By combining cationic lipid compounds with a phospholipid, positively charged vesicles and other types of lipid aggregates can bind nucleic acids, which are negatively charged, can be taken up by target cells, and can transfect target cells. (Felgner, P. L. et al. (1987) *Proc. Natl. Acad. Sci. USA* 84:7413-7417; Eppstein, D. et al., U.S. Pat. No. 4,897,355.).

Methods for incorporating cationic lipids into lipid aggregates are well known in the art. Representative methods are disclosed by Felgner et al., supra; Eppstein et al. supra; Behr et al. supra; Bangham, A. et al. (1965) *M. Mol. Biol.* 23:238-252; Olson, F. et al. (1979) *Biochim. Biophys. Acta* 557:9-23; Szoka, F. et al. (1978) *Proc. Natl. Acad. Sci. USA* 75:4194-4198; Mayhew, E. et al. (1984) *Biochim. Biophys. Acta* 775:169-175; Kim, S. et al. (1983) *Biochim. Biophys. Acta* 728:339-348; and Fukunaga, M. et al. (1984) *Endocrinol.* 115:757-761. Commonly used techniques for preparing lipid aggregates of appropriate size for use as delivery vehicles include sonication and freeze-thaw plus extrusion. See, e.g., Mayer, L. et al. (1986) *Biochim. Biophys. Acta* 858:161-168. Microfluidization is used when consistently small (50 nm to 200 nm) and relatively uniform aggregates are desired (Mayhew, E., supra). Cationic lipids have also been used in the past to deliver interfering RNA (RNAi) molecules to cells (Yu et al. (2002) *PNAS* 99: 6047-6052; Harborth et al. (2001) *Journal of Cell Science* 114:4557-4565).

The use of cationic lipids has become increasingly popular since its introduction over 15 years ago. Several cationic lipids have been described in the literature and some of these are commercially available. DOTMA (N-[1-(2,3-dioleyloxy)propyl]-N,N,N-trimethylammonium chloride) was the first cationic lipid to be synthesized for the purpose of nucleic acid transfection. See Felgner et al. (Proc. Nat'l Acad. Sci. 84, 7413 (1987); U.S. Pat. No. 4,897,355). DOTMA can be formulated alone or can be combined with DOPE (dioleoylphosphatidylethanolamine) into a liposome, and such liposomes can be used to deliver plasmids into some cells. Other classes of lipids subsequently have been synthesized by various groups. For example, DOGS (5-carboxyspermylglycinedioctadecylamide) was the first polycationic lipid to be prepared (Behr et al. Proc. Nat.'l Acad. Sci. 86, 6982 (1989); U.S. Pat. No. 5,171,678) and other polycationic lipids have since been prepared. The lipid DOSPA (2,3-dioleyloxy-N-[2(spermine-carboxamido)ethyl]-N,N-dimethyl-1-propanami-nium) has been described as an effective delivery agent (U.S. Pat. No. 5,334,761).

In other examples, cholesterol-based cationic lipids, such as DC-Chol (N,N-dimethyl-N-ethylcarboxamidocholesterol) have been prepared and used for transfection (Gao et al. Biochem. Biophys. Res. Comm. 179, 280 (1991)). In another example 1,4-bis(3-N-oleylamino-propyl)piperazine was prepared and combined with histone H1 to generate a delivery reagent that was reported to be less toxic than other reagents (Wolf et al. BioTechniques 23, 139 (1997); U.S. Pat. No. 5,744,335). Several reagents are commercially available. Some examples include LIPOFECTIN® (DOTMA:DOPE) (Invitrogen, Carlsbad, Calif.), LIPO-FECTAMINE® (DOSPA:DOPE) (Invitrogen), LIPO- FECTAMINE® 2000 (Invitrogen) FUGENE®, TRANSFECTAM® (DOGS), EFFECTENE®, and DC-Chol.

None of these reagents can be used universally for all cells. This is perhaps not surprising in light of the variation in composition of the membranes of different types of cells as well as the barriers that can restrict entry of extracellular material into cells. Moreover, the mechanism by which cationic lipids deliver nucleic acids into cells is not clearly understood. The reagents are less efficient than viral delivery methods and are toxic to cells, although the degree of toxicity varies from reagent to reagent.

However, transfection agents, including cationic lipids, are not universally effective in all cell types. Effectiveness of transfection of different cells depends on the particular transfection agent composition. In general, polycationic lipids are more efficient than monocationic lipids in transfecting eukaryotic cells. In many cases, cationic lipids alone are not effective or are only partially effective for transfection.

While the use of lipid aggregates to introduce exogenous compounds into cells (a process known in the art as "transfection") has become a routine procedure in many labs and has been adapted for use in a wide variety of cell types and lineages, it is estimated that approximately 60% of the cells and cell lines that routinely use this technique research and clinical settings are considered difficult to transfect, meaning they typically exhibit less than 60% transfection efficiency. Cells defined as difficult to transfect include primary cells, such as stem cells, progenitor cells, neuronal cells and other cell types derived from neural tissues, primary blood cells ("PBMC"), HUVEC, and the like, as well as certain cell lines that, while established, are difficult to efficiently transfect using commercially available transfection reagent. Examples of difficult to transfect cell lines include PC12, HepG2, 3T3, LNCaP, A549, Jukat, and PC3, among others.

Over the last several decades, a number of naturally occurring peptides capable of promoting the translocation of materials into a cell by passing through the cell membrane. These so-called "membrane-penetrating peptides" ("MPPs") or "cell-penetrating peptides ("CPPs") have been used to promote the transport proteins, nucleic acids, polymers, or other functional molecules into cells.

Membrane/cell-penetrating peptides (CPPs) such as the antennapedia-derived penetratin (Derossi et al., J. Biol. Chem., 269, 10444-10450, 1994) and the Tat peptide (Vives et al., J. Biol. Chem., 272, 16010-16017, 1997) have been used to deliver cargo molecules such as peptides, proteins and oligonucleotides (Fischer et al., Bioconjug. Chem., 12, 825-841, 2001) into cells. Areas of application range from purely cell biological to biomedical research (Dietz and Bahr, Mol. Cell., Neurosci, 27, 85-131, 2004). Initially, cellular uptake was believed to occur by direct permeation of the plasma membrane (Prochiantz, Cuff. Opin. Cell Biol., 12, 400-406, 2000). In recent years, evidence has been mounting to indicate that at least some CPPs increase cellular uptake of cargo by promoting endocytosis (for a review, see Fotin-Mleczek et al., Curr. Pharm. Design, 11, 3613-3628, 2005). Given these recent results, the specification of a peptide as a CPP/MPP therefore does not necessarily imply a specific cellular import mechanism, but rather refers to a function as a peptide that, when associated with a cargo molecule, either covalently or non-covalently, enhances the cellular uptake of the cargo molecule.

There exists a need for additional reagents that enhance the delivery of cargo and macromolecules into cells by improving transfection efficiency of all cell in both research and clinical settings, particularly cells that are considered "difficult to transfect" (i.e., those cells that are either refractory to transfection or that exhibit substantially lower transfection efficiency than standard transformed cell lines routinely used in laboratory settings), yet are easy to use and prepare and leverage the wide array of cationic lipid-based transfection reagents that are currently available.

SUMMARY

The present invention provides novel non-naturally occurring peptides having a cell penetrating function and being capable of forming transfection complexes with a cargo molecule and one or more cationic lipids.

Disclosed herein are compositions and methods that provide improved efficiency for introducing macromolecules, such as nucleic acids, into cells in culture or in a tissue in vivo. Accordingly, certain embodiments provide herein a complex containing, in non-covalent association, a cargo molecule, such as a nucleic acid molecule, a transfection agent and a non-naturally occurring peptide, where the non-naturally occurring peptide contains a membrane-penetrating peptide sequence. In certain aspects, the complexes contain a macromolecule to be introduced into the cell, such as a peptide, a protein, or a nucleic acid.

In one aspect of the invention, the non-naturally occurring peptides of the present invention have the general structure:

A-L-B, or

B-L-A;

Where A is membrane penetrating peptide, L is either a bond or a linker peptide, and B is a cationic moiety or a cationic polypeptide. In some preferred though non-limiting embodiments, A is a peptide sequence selected from those set forth in Table 1, or a variant thereof retaining at least a portion of its ability to enhance transfection efficiency. In some embodiments, the peptide sequence of A is between 5 to about 50 amino acids, and A is characterized in that it improves delivery of a molecule into a cell by at least 50% or more.

In some embodiments, the peptide sequence of A is between 5 to about 50 amino acids, and A is characterized in that it improves delivery of a molecule into a cell by at 75% or more.

In some embodiments, A is at least 75% identical to any one of the peptides set forth in Table 1, or a variant thereof retaining at least a portion of its ability to enhance transfection efficiency, where A is characterized in that it improves delivery of a molecule into a cell by at least 10% or more. In some embodiments, A is selected from the list consisting of any one of SEQ ID NO. 1 through SEQ ID NO. 68, or a variant thereof.

In one aspect of the invention, the non-naturally occurring peptide is selected from any one of the peptides set forth in Table 4.

Further embodiments of the present invention are directed to transfection complexes containing the non-naturally occurring peptides described above in combination with one or more transfection reagents, which transfection reagents may include one or more cationic lipids, and optionally one or more helper and/or neutral lipids.

In some embodiments, a transfection complex may include a cargo to be delivered to the interior of a cell, or optionally may be administered to an animal or to a human patient who would benefit from the administration thereof. In some exemplary though non-limiting embodiments, preferred cargo molecules suitable for use with the present invention include nucleic acid molecules such as DNA molecules or RNA molecules. Suitable DNA molecules may include a DNA molecule having an expressible nucleic acid sequence, such as an expression vector or a cDNA molecule comprising an open reading frame encoding a protein. Other suitable molecules that may function as suitable cargo in the practice of the present invention include RNA molecules, such as an mRNA molecule or an RNAi molecule.

Further embodiments of the present invention are directed to methods for preparing transfection complexes and to methods for the use thereof to deliver a cargo molecule to the interior of a cell. Methods for preparing a transfection complex can include contacting a cargo molecule with at least one cationic lipid or transfection reagent and the non-naturally occurring peptides of the present invention, optionally in the presence of one or more helper lipids and/or one or more neutral lipids, under conditions that promote the formation of a transfection complex capable of conveying the cargo to the interior of a cell.

Further embodiments of the present invention are directed to methods for transfecting cells that include forming transfection complexes comprising at least one cargo molecule, at least one cationic lipid or transfection reagent, and a non-naturally occurring peptides in accordance with the present invention, optionally having one or more helper lipids and/or one or more neutral lipids, and contacting the transfection complex with a cell under conditions that promote the transfection of the cell. Yet further embodiments of the present invention are directed to pharmaceutical preparations comprising a cargo or a drug to be delivered to an animal or a human subject, at least cationic lipid or transfection reagent and a non-naturally occurring peptide of the present invention, optionally in the presence of one or more helper lipids and/or one or more neutral lipids, to form a pharmaceutically active complex suitable for the delivery of a drug or biologically active compound to an animal or to a human subject having need thereof for the treatment of a physiological condition or disorder.

Other embodiments of the present invention will be apparent to one of ordinary skill in light of the following drawings and description of the invention, and of the claims.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings in which:

DETAILED DESCRIPTION OF THE EMBODIMENTS

Figure 1:
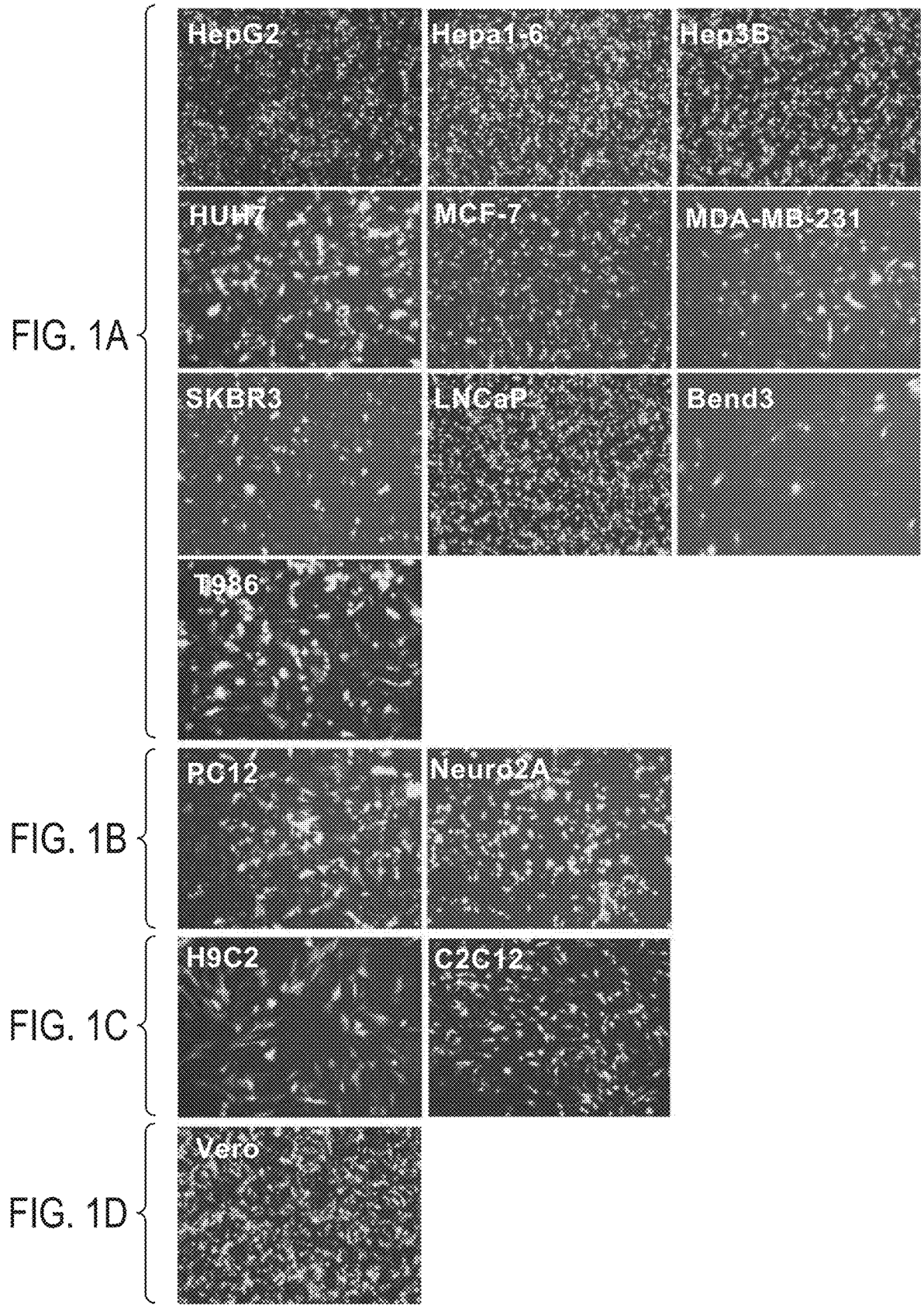
FIG. 1A shows a panel of 10 different cancer cell lines expressing Green Fluorescent Protein (GFP) that were transfected with an expression vector encoding GFP using LIPOFECTAMINE® 3000 in combination with a peptide according to one embodiment.
FIG. 1B shows 2 different neuronal cell lines expressing GFP that were transfected with an expression vector encoding GFP using LIPOFECTAMINE® 3000 in combination with a peptide according to one embodiment.
FIG. 1C shows 2 different myoblast cell lines expressing GFP that were transfected with an expression vector encoding GFP using LIPOFECTAMINE® 3000 in combination with a peptide according to one embodiment.
FIG. 1D shows a kidney fibroblast cell line expressing GFP that were transfected with an expression vector encoding GFP using LIPOFECTAMINE® 3000 in combination with a peptide according to one embodiment.

The present invention provides improved reagents and compositions that are suitable for the transfection of cells. In particular, the present invention provides compositions and reagents that enhance the transfection efficiency of all cells, including those cell types that are considered to typically be difficult to transfect. The compositions and reagents of the present invention, when used in accordance with the methods described herein as well as with the general knowledge and expertise within the purview of one having ordinary skill level in the art can typically increase the transfection efficiency of such by up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 100% or in excess of 100%. The invention accomplishes this by providing novel peptides comprising a cell/membrane penetrating peptide sequence used in combination with one or more transfection lipids as described in greater detail below.

Definitions

The terms used throughout this specification generally have their ordinary meanings in the art, within the context of the invention, and in the specific context where each term is used. Certain terms are discussed below, or elsewhere in the specification, to provide additional guidance to the practitioner in describing the various embodiments of the invention and how to make and use them. It will be appreciated that the same concept can be expressed in more than one way. Consequently, alternative language and synonyms may be used for any one or more of the terms discussed herein, nor is any special significance to be placed upon whether or not a term is elaborated or discussed in greater detail herein. Synonyms for certain terms may be provided. A recital of one or more synonyms does not exclude the use of other synonyms. The use of examples anywhere in this specification, including examples of any terms discussed herein, is illustrative only, and in no way limits the scope and meaning of the invention or of any exemplified term.

The term "introduction" when used in the context of introducing a macromolecule into cell culture refers to the provision of the macromolecule or compound into the culture medium with the understanding that the goal of introducing the macromolecule is to enable the transfer of macromolecule from the extracellular compartment to the cytoplasmic compartment of the cultured cell.

The term "introduction" of a macromolecule or compound into at least one cell refers to the provision of a macromolecule or compound to a cell, such that the macromolecule or compound becomes internalized in the cell. For example, a macromolecule or compound can be introduced into a cell using transfection, transformation, injection, and/or liposomal introduction, and may also be introduced into a cell using other methods known to those of ordinary skill in the art. Preferably, a macromolecule or compound is introduced into a cell by liposomal introduction. The macromolecule is preferably a protein, peptide, polypeptide, or nucleic acid. The macromolecule may a protein. Alternatively, the macromolecule may be a peptide. Alternatively, the macromolecule may be a polypeptide. The macromolecule may also be a nucleic acid.

The term "cargo", when used herein in the context of the delivery of a cargo into the interior of a cell, such as by mean of transfection, generally refers to any substance that is to be conveyed to the interior of a cell, either in culture in a laboratory or in a tissue in an animal or a human. A cargo may, depending on the application, be a macromolecule such as a nucleic acid, a protein, or a peptide, or may be a drug or other organic small molecule.

The term "macromolecule," as used herein, encompasses biomolecules. In one embodiment, the term macromolecule refers to nucleic acid. In a preferred embodiment, the term macromolecule refers to deoxyribonucleic acid (DNA) and ribonucleic acid (RNA). In some embodiments, the term macromolecule refers to DNA. The DNA can be either linear DNA or circular DNA, such as DNA in the form of a circular plasmid, an episome or an expression vector. In certain preferred though non-limiting embodiments, the term macromolecule refers to complementary DNA (cDNA) have an expressible nucleic acid sequence, including at least one open reading frame operably linked to one or more nucleic acid sequence required for the transcription of an mRNA from the expressible nucleic acid sequence. A macromolecule can be charged or uncharged. A DNA molecule is an example of a charged macromolecule. In some instances, the term "macromolecule", as used herein, may be used interchangeably with the terms "expressible nucleic acid" and "expression vector". In other embodiments, the term "macromolecule refers to an RNA molecule. The RNA molecule may be any type of RNA molecule, including but not limited to an mRNA, a siRNA, a miRNA, an antisense RNA, a ribozyme, or any other type or species of RNA molecule familiar to those skilled in the art without limitation, which would be sought to be delivered to the interior of a cell.

The term "transfection" is used herein to mean the delivery of nucleic acid, protein or other macromolecule to a target cell, such that the nucleic acid, protein or other macromolecule is expressed or has a biological function in the cell.

The term "expressible nucleic acid" as used herein includes both DNA and RNA without regard to molecular weight, and the term "expression" means any manifestation of the functional presence of the nucleic acid within the cell including, without limitation, both transient expression and stable expression. Functional aspects include inhibition of expression by oligonucleotides or protein delivery.

The term "expression of nucleic acid" and their equivalents refer to the replication of the nucleic acid in a cell, to transcription of DNA to messenger RNA, to translation of RNA to protein, to post-translational modification of protein, and/or to protein trafficking in the cell, or variations or combinations thereof.

The term "cell" as used herein refers includes all types of eukaryotic and prokaryotic cells. In preferred embodiments, the term refers to eukaryotic cells, especially cells grown in culture, or cells found in a tissue in an animal or a human. In preferred embodiments, a cell refers to a mammalian cell. In certain exemplary though non-limiting embodiments, the term "cell" is meant to refer to any cell and cell line that is routinely used in research and clinical settings, and may include immortalized cell lines, transformed cell lines, or primary cells, without limitation.

The phrase "difficult to transfect", or similar variants of the phrase, when used in the context of transfection procedures and reagents, is a relative term that generally refers to any cell or cell line that typically exhibits less than 60% transfection efficiency when transfected using standard commercially available transfection reagents such as, e.g., cationic lipids (examples of which include, but are not limited to, LIPOFECTAMINE® 2000, LIPOFECTAMINE® LTX, LIPOFECTAMINE®, LIPOFECTIN®, FUGENE® HD, X-TREMEGENE™ HP, and the like). Cells typically thought of as "difficult to transfect" include primary cells, such as stem cells, progenitor cells, neuronal cells and other cell types derived from neural tissues, primary blood cells ("PBMC"), HUVEC, and the like, as well as certain cell lines that, while established, are difficult to efficiently transfect using commercially available transfection reagents. Examples of difficult to transfect cell lines include, but are not limited to, PC12, HepG2, 3T3, LNCaP, A549, Jurkat, primary cells, H9 embryonic stem cells, cultured embryonic stem cells, culture induced pluripotent stem cells (iPS cells), K-562, L6, L929, MCF-7, RAW 264.7, HT29, U937, Vero, HCT116, C6, C2C12, HL60, THP1, BHK, PC3, P19, SH-SY5Y, U2OS, HUH7, and PC3, among others. The recitation herein of various specific cell types and cell lines that are thought of in the art is in no way meant to limit the scope of the present invention solely to those cell lines or close derivatives thereof, but is merely meant to illustrate the preponderance of cell lines and types commonly used in laboratory settings that typically display less than 60% transfection efficiency using commonly available cationic lipid based transfections reagents, and which would benefit from the novel compositions and formulations described herein to improve the relative transfection efficiency by at least 5% or more.

By "cell culture" or "culture" is meant the maintenance of cells in an artificial, in vitro environment.

"Recombinant protein" refers to protein that is encoded by a nucleic acid that is introduced into a host cell. The host cell expresses the nucleic acid. The term "expressing a nucleic acid" is synonymous with "expressing a protein from an RNA encoded by a nucleic acid. "Protein" as used herein generically refers to any naturally occurring or synthetic polymer of amino acids, e.g., peptides, polypeptides, proteins, lipoproteins, glycoproteins, etc.

As used herein, the term "polypeptide" generally refers to a naturally occurring, recombinant or synthetic polymer of amino acids, regardless of length or post-translational modification (e.g., cleavage, phosphorylation, glycosylation, acetylation, methylation, isomerization, reduction, farnesylation, etc. . . . ), that are covalently coupled to each other by sequential peptide bonds. Although a "large" polypeptide is typically referred to in the art as a "protein" the terms "polypeptide" and "protein" are often used interchangeably. In general, the first amino acid residue or group of amino acid residues in a polypeptide are said to be at the "amino-terminal" or "N-terminal" of the polypeptide. Similarly, the last amino acid residue, or group of amino acid residues in a polypeptide are said to be at the "carboxy-terminal" or "C-terminal".

The term "peptide" as used herein is intended to be a generic term which broadly includes short peptides (typically less than 100 amino acids), polypeptides (typically more than 100 amino acids, and proteins (which contain one or more polypeptide chains). The peptides of this invention typically have more than two amino acids; preferred peptides have more than 4 amino acids.

When used herein in the context of polypeptides described herein, the terms "variant", "variants", and the like, generally refer to polypeptide(s) that are structurally similar to a reference polypeptide but are characterized by differences in amino acid sequence between the polypeptides and the reference polypeptide (e.g., having at least 10%, at least 20%, at least 30%, at least 50%, at least 75%, at least 85%, or at least 95% sequence identity) and/or in the presence or absence of one or more biochemical modifications (e.g., post-translational modifications, substitutions, adduct additions, and the like). While a subset of the general activities of certain variants may be similar, structural differences occurring between the variants may result in at least a portion of their activities being non-overlapping. A "variant" may refer to a polypeptide molecule that is altered at one or more locations in the polypeptide sequence, including additions, deletion, substitutions of one or more than one contiguous amino acid in the sequence, as well as covalent modifications of the molecule, relative to the polypeptide molecule. Thus, in some instances, the terms "variant" and "isoform" may be used interchangeably. Illustrative examples of such variants would include, by way of example only, polypeptides in which replacement of a hydrogen group by an alkyl, acyl, thiol, amide or other such functional group has occurred at one or more amino acid residues. A variant may have "conservative" changes, wherein a substituted amino acid may have similar structural and/or chemical properties (e.g., replacement of a non-polar amino acid residue with a different non-polar amino acid residue). A variant may also have "nonconservative" changes (e.g., replacement of a polar amino acid residue with a non-polar or a charged amino acid residue). Variants may also include similar minor variations in amino acid sequence including, but not limited to, deletions, truncation, insertions, or combinations thereof. Guidance in determining which amino acid residues may be substituted, inserted, or deleted without abolishing or otherwise substantially affecting biological activity is widely available in the art. Further guidance may be found using computer programs well known in the art, for example, DNASTAR software. In general and in the context of the present invention, a variant will retain at least a subset of the biological functions typically associated with a known membrane penetrating peptide, such as, for example, the ability to facilitate the translocation of a cargo colecule, such as, e.g., a nucleic acid molecule, across a cell membrane to the cytosolic compartment thereof.

As used herein, the term "amino acid" generally refers to naturally occurring or synthetic amino acids, as well as amino acid analogs and amino acid mimetics that function in a manner similar to naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine or norvaline) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. The term "amino acid" can refer to amino acids or their derivatives (e.g., amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine, N-acetyl cysteine.

"Kit" refers to transfection, DNA, RNAi, or other cargo (e.g., protein or anionic molecule) delivery or protein expression or knockdown kits which include one or more of the reagents of the present invention or mixtures thereof. The kits may include one or more of the non-naturally occurring peptides described herein, optionally with one or more cationic lipids or transfections reagents. In some embodiments, the peptide and the lipid reagents may be provided in a single formulation. In other embodiments, the lipid and the peptide may be provided separately, with instruction to the user to combine the reagents at the time of use. Such kits may comprise a carrying means being compartmentalized to receive in close confinement one or more container means such as vials, test tubes and the like. Each of such container means comprises components or a mixture of components needed to perform transfection. Such kits may optionally include one or more components selected from any cargo molecules such as, e.g., nucleic acids (preferably one or more expression vectors, DNA molecules, RNA molecules or RNAi molecules), cells, one or more compounds of the present invention, lipid-aggregate forming compounds, transfection enhancers, biologically active substances, etc.

The medium, methods, kit and composition of the present invention are suitable for either monolayer or suspension culture, transfection, and cultivation of cells, and for expression of protein in cells in monolayer or suspension culture. Preferably, the medium, methods, kit and composition of the present invention are for suspension culture, transfection, and cultivation of cells, and for expression of protein product in cells in suspension culture.

By "culture vessel" is meant any container, for example, a glass, plastic, or metal container, that can provide an aseptic environment for culturing cells.

The term "combining" refers to the mixing or admixing of ingredients.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector. Certain vectors used in accordance with the practice of invention described herein may be well-known vectors used in the art, such as, e.g., pCDNA 3.3, or a modified version thereof. Non-limiting examples of the types of modification to a vector that may be suitable in the practice of the present invention include, though are not limited to, modification such as the addition of modification of one or more enhancers, one or more promoters, one or more ribosomal binding sites, one or more origins of replication, or the like. In certain preferred though non-limiting embodiments, and expression vector used in the practice of the present invention may include one or more enhancer elements selected to improve expression of the protein of interest in the present transient expression system. The selected enhancer element may be positioned 5' or 3' to the expressible nucleic acid sequence used to express the protein of interest.

As used herein, the phrase "expression vector containing an expressible nucleic acid" generally refers to a vector as defined above which is capable to accommodating an expressible nucleic acid sequence having at least one open-reading frame of a desired protein of interest (said protein of interest being selected by the user of the present invention) in additional to one or more nucleic acid sequences or elements that are required to support the expression thereof in a cell or in a cell-free expression system. Such additional nucleic acid sequences or elements that may be present in an expression vector as defined herein may include, one or more promoter sequences, one or more enhancer elements, one or more ribosomal binding sites, one or more translational initiation sequences, one or more origins of replication, or one or more selectable markers. A variety of nucleic acid sequences or elements serving this purpose are familiar to the skilled artisan, and the selection of one or more thereof for use in the practice of the present invention is well within the purview of the skilled practitioner.

The terms "polynucleotide" and "nucleic acid" are used interchangeably herein and refer to any nucleic acid, including deoxyribonucleic acid (DNA) and ribonucleic acid (RNA). In preferred embodiments, "nucleic acid" refers to DNA, including genomic DNA, complementary DNA (cDNA), and oligonucleotides, including oligo DNA. In certain preferred though non-limiting embodiments, "nucleic acid" refers to genomic DNA and/or cDNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, the term "RNA-interference" or "RNAi" generally refers to the process of sequence-specific post-transcriptional gene silencing. RNAi is a process by which specific mRNAs are degraded into short RNAs. To mediate RNAi, a double-stranded RNA (dsRNA) with substantial sequence identity to the target mRNA is introduced into a cell. The target mRNA is then degraded in the cell, resulting in decreased levels of that mRNA and the protein it encodes.

As used herein, the term "RNAi construct" generally refers to small interfering RNAs (siRNAs), hairpin RNAs, and other RNA species that can be cleaved in vivo to form siRNAs. The term also encompasses expression vectors capable of giving rise to transcripts that form dsRNAs or hairpin RNAs in cells, and/or transcripts that can produce siRNAs in vivo. The term "RNAi expression vector" refers to replicable nucleic acid constructs used to express (transcribe) RNA that produces siRNA duplexes in a host cell in which the construct is expressed.

As used herein, the term "short-interfering RNA" or "siRNA" generally refers to a short (approximately 19 to about 25 nucleotides in length), double stranded RNA molecule of defined nucleotide sequence that is capable of mediating RNAi.

As used herein the terms "complexation reaction," "complexation media" or the like, generally refer to a physiologically acceptable culture media or reaction in which a nucleic acid is complexed to a transfection reagent formulation. Typically, a nucleic acid that is to be introduced into a cell for the purpose of expressing a protein is first complexed with a suitable transfection reagent (such as, e.g., a cationic lipid formulation) to lipid/nucleic acid complexes or aggregates.

Drug refers to any therapeutic or prophylactic agent other than food which is used in the prevention, diagnosis, alleviation, treatment, or cure of disease in man or animal.

A variety of techniques and reagents are available for the introduction of macromolecules into a target cell in a process known as "transfection". Commonly used reagents include, for example, calcium phosphate, DEAE-dextran and lipids. For examples of detailed protocols for the use of reagents of these types, numerous references texts are available for example, Current Protocols in Molecular Biology, Chapter 9, Ausubel, et al. Eds., John Wiley and Sons, 1998. Additional methods for transfecting cells are known in the art, and may include electroporation (gene electrotransfer), sono-poration, optical transfection, protoplast fusion, impalefection, magnetofection, or viral transduction.

A "reagent for the introduction of macromolecules" into cells or a "transfection reagent" is any material, formulation or composition known to those of skill in the art that facilitates the entry of a macromolecule into a cell. For example, see U.S. Pat. No. 5,279,833. In some embodiments, the reagent can be a "transfection reagent" and can be any compound and/or composition that increases the uptake of one or more nucleic acids into one or more target cells. A variety of transfection reagents are known to those skilled in the art. Suitable transfection reagents can include, but are not limited to, one or more compounds and/or compositions comprising cationic polymers such as polyethyleneimine (PEI), polymers of positively charged amino acids such as polylysine and polyarginine, positively charged dendrimers and fractured dendrimers, cationic β-cyclodextrin containing polymers (CD-polymers), DEAE-dextran and the like. In some embodiments, a reagent for the introduction of macromolecules into cells can comprise one or more lipids which can be cationic lipids and/or neutral lipids. Preferred lipids include, but are not limited to, N-[1-(2,3-dioleyloxy) propyl]-N,N,N-trimethylamonium chloride (DOTMA), dioleoylphosphatidylcholine (DOPE),1,2-Bis(oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC), cholesteryl (4'-trimethylammonio)butanoate (ChoTB), cetyltrimethylammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dimyristyloxypropyl-3-dimethyl-hydroxyethyl ammonium bromide (DMRIE), O,O'-didodecyl-N-[p(2-trimethylammonioethyloxy)benzoyl]-N, N,N-trimethylam-monium chloride, spermine conjugated to one or more lipids (for example, 5-carboxyspermylglycine dioctadecylamide (DOGS), N,N$^I$,N$^{II}$,N$^{III}$-tetramethyl-N,N$^I$, N$^{II}$,N$^{III}$-tet-rapalmitylspermine (TM-TPS) and dipalmitoyl-phasphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trilysyl-alanyl-TRIS mono-, di-, and tri-palmitate, (3β-[N-(N', N'-dimethylaminoethane)-carbamoyl] cholesterol (DC-Chol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido)ethyl]-N,N-dimethyl-1-propanamin-iniumtrifluoroacetate (DOSPA) and combinations thereof.

Those skilled in the art will appreciate that certain combinations of the above mentioned lipids have been shown to be particularly suited for the introduction of nucleic acids into cells for example a 3:1 (w/w) combination of DOSPA and DOPE is available from Life Technologies Corporation, Carlsbad, Calif. under the trade name LIPOFECTAMINE™, a 1:1 (w/w) combination of DOTMA and DOPE is available from Life Technologies Corporation, Carlsbad, Calif. under the trade name LIPOFECTIN®, a 1:1 (M/M) combination of DMRIE and cholesterol is available from Life Technologies Corporation, Carlsbad, Calif. under the trade name DMRIE-C reagent, a 1:1.5 (M/M) combination of TM-TPS and DOPE is available from Life Technologies Corporation, Carlsbad, Calif. under the trade name CELLFECTIN® and a 1:2.5 (w/w) combination of DDAB and DOPE is available from Life Technologies Corporation, Carlsbad, Calif. under the trade name LIPFECTACE®. In addition to the above-mentioned lipid combinations, other formulations comprising lipids in admixture with other compounds, in particular, in admixture with peptides and proteins comprising nuclear localization sequences, are known to those skilled in the art. For example, see international application no. PCT/US99/26825, published as WO 00/27795, both of which are incorporated by reference herein.

Lipid aggregates such as liposomes have been found to be useful as agents for the delivery of macromolecules into cells. In particular, lipid aggregates comprising one or more cationic lipids have been demonstrated to be extremely efficient at the delivery of anionic macromolecules (for example, nucleic acids) into cells. One commonly used cationic lipid is N-[1-(2,3-dioleoyloxy)propyl]-N,N,N-trimethylammonium chloride (DOTMA). Liposomes comprising DOTMA alone or as a 1:1 mixture with dioleoylphosphatidylethanolamine (DOPE) have been used to introduce nucleic acids into cells. A 1:1 mixture of DOTMA:DOPE is commercially available from Life Technologies Corporation, Carlsbad, Calif. under the trade name of LIPOFECTIN™. Another cationic lipid that has been used to introduce nucleic acids into cells is 1,2-bis(oleoyl-oxy)-3-3-(trimethylammonia) propane (DOTAP). DOTAP differs from DOTMA in that the oleoyl moieties are linked to the propylamine backbone via ether bonds in DOTAP whereas they are linked via ester bonds in DOTMA. DOTAP is believed to be more readily degraded by the target cells. A structurally related group of compounds wherein one of the methyl groups of the trimethylammonium moiety is replaced with a hydroxyethyl group are similar in structure to the Rosenthal inhibitor (RI) of phospholipase A (see Rosenthal, et al., (1960) J. Biol. Chem. 233:2202-2206.). The RI has stearoyl esters linked to the propylamine core. The dioleoyl analogs of RI are commonly abbreviated DOR1-ether and DOR1-ester, depending upon the linkage of the lipid moiety to the propylamine core. The hydroxyl group of the hydroxyethyl moiety can be further derivatized, for example, by esterification to carboxyspermine.

Another class of compounds which has been used for the introduction of macromolecules into cells comprise a carboxyspermine moiety attached to a lipid (see, Behr, et al., (1989) Proceedings of the National Academy of Sciences, USA 86:6982-6986 and EPO 0 394 111). Examples of compounds of this type include dipalmitoylphosphatidylethanolamine 5-carboxyspermylamide (DPPES) and 5-carboxyspermylglycine dioctadecylamide (DOGS). DOGS is commercially available from Promega, Madison, Wis. under the trade name of TRANSFECTAM™.

A cationic derivative of cholesterol (3β-[N-(N',N'-dimethylaminoethane)-carbamoyl] cholesterol, DC-Chol) has been synthesized and formulated into liposomes with DOPE (see Gao, et al., (1991) BBRC 179(1):280-285.) and used to introduce DNA into cells. The liposomes thus formulated were reported to efficiently introduce DNA into the cells with a low level of cellular toxicity. Lipopolylysine, formed by conjugating polylysine to DOPE (see Zhou, et al., (1991) BBA 1065:8-14), has been reported to be effective at introducing nucleic acids into cells in the presence of serum.

Other types of cationic lipids that have been used to introduce nucleic acids into cells include highly packed polycationic ammonium, sulfonium and phosphonium lipids such as those described in U.S. Pat. Nos. 5,674,908 and 5,834,439, and international application no. PCT/US99/26825, published as WO 00/27795. One particularly preferred though non-limiting transfection reagent for delivery of macromolecules in accordance with the present invention is LIPOFECTAMINE 2000™ which is available from Life technologies (see U.S. international application no. PCT/US99/26825, published as WO 00/27795). Another preferred though non-limiting transfection reagent suitable for delivery of macromolecules to a cell is EXPIFECTAMINE™. Other suitable transfection reagents include LIOFECTAMINE™ RNAiMAX, LIPOFECTAMINE™ LTX, OLIGOFECTAMINE™, Cellfectin™ INVIVOFECTAMINE™, INVIVOFECTAMINE™ 2.0, and any of the lipid reagents or formulations disclosed in U.S. Patent Appl. Pub. No. 2012/0136073, by Yang et al. (incorporated herein by reference thereto). A variety of other transfection reagents are known to the skilled artisan and may be evaluated for the suitability thereof to the transient transfection systems and methods described herein.

The present invention provides improved reagents and compositions that are suitable for the transfection of cells. In particular, the present invention provides compositions and reagents that enhance the transfection efficiency of all cells, including those cell types that are considered to typically be difficult to transfect. The compositions and reagents of the present invention, when used in accordance with the methods described herein as well as with the general knowledge and expertise within the purview of one having ordinary skill level in the art can typically increase the transfection efficiency of such cells by up to 10%, up to 15%, 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 100% or in excess of 100%. The invention accomplishes this by providing novel peptides comprising a cell/membrane penetrating peptide sequence used in combination with one or more transfection lipids for the delivery of a cargo molecule, in particular but not limited to a nucleic acid molecule such as a DNA molecule or an RNA molecule, to the interior or cytoplasmic compartment of a cell in culture or a cell or tissue in vivo, in particular but not limited to a cell that in considered "difficult to transfect", as described in greater detail below.

Membrane/Cell-Penetrating Peptides

The present invention is directed to non-naturally occurring, synthetic peptides that are used in combination with transfection reagents, which transfections reagents may preferably include though are not limited to, lipid-based transfection reagents, particularly cationic lipid-based transfection reagents, the inclusion of which in a transfection complex improve the transfection efficiency of cells in part by enhancing the transport of a cargo molecule, e.g., a nucleic acid molecule or any other suitable cargo molecule such as will be readily apparent to one skilled in the art, across the cell membrane such that the cargo molecule is delivered to the cytosolic compartment of a cell in culture or in a tissue in vivo.

Ideally, the non-naturally occurring peptides of the present invention will be used to form a multi-component complex with a lipid aggregate composition and the cargo molecule such that the complex enhances the delivery of the cargo molecule to the cytosolic compartment of the cell or tissue.

In one aspect of the invention, non-naturally occurring peptides are contacted with at least one transfection reagent and at least one cargo molecule to form a transfection complex comprising the transfection reagent, the cargo, and the peptide, and being characterized by improving the transfection efficiency (measured as improved transfer of the cargo to the interior of a cell in culture or in a tissue in vivo) of a complex compared to an identical transfection complex that lacks the non-naturally occurring peptide.

The selection of what constitutes an optimal transfection reagent for use with the present invention depends on the identity and nature of the cargo to be delivered, the identity and characteristics of the cells to be transfected, wither the transfection is to take place in isolated cells in culture or in a tissue in an animal or a human in vivo, and the identity of the non-naturally occurring peptide. All these characteristics are well-known to the practitioner having ordinary skill level in the art, and the selection of an optimal transfection reagent in the specific context of specific applications, as well as the way to determine what constitutes of optimal concentrations and formulation of the components is readily apparent to such a person without undue experimentation and without departing from the spirit and scope of the invention.

In certain preferred though non-limiting embodiments, the transfection reagent selected for use in the formation of a transfection complex in accordance with the embodiments set forth herein may be a cationic lipid, in particular a cationic lipid capable of forming lipid aggregates.

In some embodiments, a transfection complex may include a lipid aggregate composition, the lipid aggregate composition comprising at least one cationic lipid, optionally more than one cationic lipid, optionally in the presence of at least one helper lipid, contacted with a cargo molecule and a least one non-naturally occurring peptides having the general structure:

A-L-B, or

B-L-A;

Where A is membrane penetrating peptide (MPP), L is either a covalent bond linking A to B or a linker peptide, and where B is either a cationic polypeptide, a cationic moiety, or a cationic peptide covalently linked to a cationic moiety, where the non-naturally occurring peptide is characterized in that the presence of non-naturally occurring peptide as a component of a transfection complex increases the transfection efficiency of the transfection complex is enhanced or improved up to 10%, up to 15%, 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 100%, up to 150%, up to 200%, up to 250%, up to 300%, up to 350%, up to 400%, up to 500% or in excess of 500% above that of an identical transfection complex that lacks the non-naturally occurring peptide.

A may be any peptide, without limitation and independent of the mechanism by which the peptide carries out its function, that is known or can be demonstrated to enhance or to promote the transfer of a molecule, such as a cargo molecule as defined above, in particular a nucleic acid molecule such as a DNA or an RNA molecule, from an extracellular compartment, such as, e.g., a cell culture medium or an interstitial or body fluid, across a cell membrane such that the cargo molecule is conveyed to the cytoplasmic compartment of the cell where it can effect at least one measurable biological response or function. The determination of what constitutes "enhancement" of transfer across a cell membrane is well within the skill level of a practitioner having ordinary skill level in the art, and the identification of a suitable peptide or variant of a known peptide that functions to enhance or promote the transfer of a cargo molecule in such a manner is readily apparent to such a person using a wide variety of known techniques.

In some non-limiting embodiments, the peptide sequence of A may be between about 5 to about 75 amino acids, between about 5 to about 60 amino acids, between about 5 to about 50 amino acids, between about 5 to about 40 amino acids, between about 5 to about 30 amino acids, between about 5 to about 20 amino acids or between about 5 to about 15 amino acids, between about 10 to about 75 amino acids, between about 10 to about 60 amino acids, between about 10 to about 50 amino acids, between about 10 to about 40 amino acids, between about 10 to about 30 amino acids, between about 10 to about 20 amino acids, or between about 10 to about 15 amino acids, and where A is characterized in that the presence of non-naturally occurring peptide as a component of a transfection complex enhances the transfection efficiency of the transfection complex up to 10%, up to 15%, 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 100%, up to 150%, up to 200%, up to 250%, up to 300%, up to 350%, up to 400%, up to 500% or in excess of 500% above that of an identical transfection complex that lacks the non-naturally occurring peptide.

A variety of peptide sequences suitable for use as an MPP (i.e., region A of the structure A-L-B or B-L-A shown above) in the non-naturally occurring peptides as described herein are known in the art, any of which may be used in the practice of the present invention without limitation. A representative though non-limiting set of peptides that are known to function as an MPP is shown on Table 1.

In some non-limiting embodiments, A is a peptide comprising a peptide sequence selected from any one of SEQ ID NO. 1-68, or a variant thereof having at least 50%, at least 55%, at least 60%, at least 65%, at least 70%, at least 75%, at least 80%, at least 85%, at least 90% or at least 95% sequence similarity to any one of SEQ ID NO: 1-68 and retaining at least 50% at least 55%, at least 60%, at least 65%, at least 70%, at least 75%, at least 80%, at least 85%, at least 90% or at least 95%, at least 155%, greater that 100%, up to 115%, up to 120%, up to 130%, up to 140%, up to 150%, up to 160%, up to 170%, up to 180% of the function thereof to enhance the delivery of a cargo molecule to the interior of a cell.

In some embodiments, L may be a covalent bond linking A and B.

In some embodiments, L may comprise a dipeptide of neutral (uncharged at physiologic pH) amino acids in which optionally one of the two amino acids in the dipeptide comprises at least one polar side chain. In an embodiment, L may comprise a dipeptide comprising at least one polar side chain or at least one hydrophobic side chain, wherein said polar or hydrophobic side chain preferably is not a bulky side chain. In an embodiment L may comprise a dipeptide comprising at least one glycine, at least one, valine, at least one alanine, at least one serine or at least one threonine. In some embodiments, L may comprise a dipeptide selected from the list consisting of GG, AA, GA, AG, AS, AY, GS, GT, GV, AV, SV, TV, VG, VA, and VT.

In some embodiments, L may be linker peptide having between about 3 to about 50, about 45, about 40, about 35, about 30, about 25, about 20, about 15, about 14, about 13, about 12, about 11, about 10, about 9, about 8, about 7, about 6, about 5, about 4 amino acids, where at least about 50%, at least about 60%, at least about 70%, at least about 80%, at least about 90% or greater than about 90% of the amino acids are neutral.

In some embodiments, L may be linker peptide having between about 3 to about 50, about 5 to about 25, about 6 to about 20, about 8 to about 15 amino acids, or about 4, 5, 6, 7, 8, 9, 10, 11, 12, 13, 14, 15, 16, 17, 18, 19, 20, 21, 22, 23, 24, 25, 26, 27, 28, 29, or 30 amino acids, where up to about 35% of the amino acids contain a neutral polar side chain, and/or at least 35% of the amino acids contain a hydrophobic side chain, where the polar and hydrophobic side chains are not bulky side chains.

In some embodiments, L may be linker peptide having between about 3 to about 50, about 5 to about 25, about 6 to about 20, about 8 to about 15 amino acids, or about 4, 5, 6, 7, 8, 9, 10, 11, 12, 13, 14, 15, 16, 17, 18, 19, 20, 21, 22, 23, 24, 25, 26, 27, 28, 29, or 30 amino acids, where up to about 35% of the amino acids are selected from serine, threonine, valine, isoleucine, and leucine.

In some embodiments, L may be linker peptide having between about 3 to about 50, about 5 to about 25, about 6 to about 20, about 8 to about 15 amino acids, or about 4, 5, 6, 7, 8, 9, 10, 11, 12, 13, 14, 15, 16, 17, 18, 19, 20, 21, 22, 23, 24, 25, 26, 27, 28, 29, or 30 amino acids, where at least about 50%, at least about 55%, at least about 60%, at least about 65%, at least about 70%, at least about 75%, at least about 80% or more of the amino acids are glycine or alanine.

In some embodiments, L may be linker peptide having the structure:

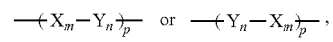

$$-(X_m-Y_n)_p- \quad \text{or} \quad -(Y_n-X_m)_p-,$$

where each X is independently neutral amino acid with a non-polar side chain, where each Y is independently a neutral amino acid with a polar side chain, and where m is an integer from 3 to 10, where n is an integer from 1 to 5, and where when L is not a bond, p is an integer from 1 to 20. In an embodiment, m>n. In some embodiments, m is 2 and n is 1, or m is 3 and n is 1 or 2. In some embodiments, each X is independently glycine, alanine, valine, leucine or isoleucine. In some embodiments, each Y is independently serine or threonine.

A variety of peptide sequences suitable for use as a Linker (i.e., region L of the structure A-L-B or B-L-A shown above) in the non-naturally occurring peptides as described herein may be used in the practice of the present invention, any of which may be used in the practice of the present invention without limitation. A representative though non-limiting set of Linker peptides that are contemplated for use with the embodiments described herein are set forth in Table 2.

In some non-limiting embodiments, L is a peptide comprising a peptide sequence selected from any one of SEQ ID NO. 69-81, or a variant thereof having at least 50%, at least 55%, at least 60%, at least 65%, at least 70%, at least 75%, at least 80%, at least 85%, at least 90% or at least 95% sequence similarity to any one of SEQ ID NO. 69-81 and retaining at least 50% at least 55%, at least 60%, at least 65%, at least 70%, at least 75%, at least 80%, at least 85%, at least 90% or at least 95%, at least 155%, greater that 100%, up to 115%, up to 120%, up to 130%, up to 140%, up to 150%, up to 160%, up to 170%, up to 180% of the function thereof to enhance the delivery of a cargo molecule to the interior of a cell.

In some embodiments, B may be either a cationic polypeptide, a cationic moiety, or a cationic peptide covalently linked to a cationic moiety. Any cationic moiety known in the art to impart a cationic charge to a molecule, in particular a peptide, may be selected for use in the present invention, without limitation. Preferred though non-limiting examples of cationic moieties suitable for use in the present invention include polyamines, such as, for example, one or more of putrescine, cadaverine, spermine, spermidine. Additional cationic moieties may include poly-L-Lysine.

In some embodiments, B may be a peptide having a peptide sequence between about 3 to about 50 amino acids, about 5 to about 25, about 6 to about 20, about 8 to about 15 amino acids, or about 4, 5, 6, 7, 8, 9, 10, 11, 12, 13, 14, 15, 16, 17, 18, 19, 20, 21, 22, 23, 24, 25, 26, 27, 28, 29, or 30 amino acids, where at least 50%, at least 55%, at least 60%, at least 65%, at least 70%, at least 75%, at least 80%, at least 85%, at least 90%, or at least 95% of the amino acids are positively charged at physiologic pH.

A variety of peptide sequences suitable for use as a Cationic region (i.e., region B of the structure A-L-B or B-L-A shown above) in the non-naturally occurring peptides as described herein may be used in the practice of the present invention, any of which may be used in the practice of the present invention without limitation. A representative though non-limiting set of Linker peptides that are contemplated for use with the embodiments described herein are set forth in Table 3.

TABLE 1

Exemplary Membrane Penetrating Peptide (MPP) sequences

| Name | Peptide Sequence | SEQ ID NO: |
|---|---|---|
| DPV10/6 | SRRARRSPRESGKKRKRKR | 1 |
| DPV15b | CGAYDLRRRERQSRLRRRERQSR | 2 |
| YM-3 | GYGRKKRRGRRRTHRLP | 3 |
| Penetration | IGCRH | 4 |
| Tat(46-57) | CYGRKKRRQRRR | 5 |
| LR11 | RILQQLLFIHF | 6 |
| C45D18 | DTWAGVEAIIRILQQLLFIHFR | 7 |
| Lyp-1 | CGNKRTRGC | 8 |
| Lyp-2 | CAGRRSAYC | 9 |
| (42-38)(9-1) Crot | GSGKKGGKKHCQKY | 10 |
| (1-9)(38-42) Crot | YKQCHKKGGKKGSG | 11 |
| BMV GAG | KMTRAQRRAAARRNRWTARGC | 12 |
| hPER1-PTD (830-845)NLS | GRRHHCRSKAKRSRHH | 13 |
| hLF1 | KCFQWQRNMRKVRGPPVSCIKR | 14 |
| hLF2 | KCFQWQRNVRKVRGPPVSCIKR | 15 |
| hLF3 | KCFQWQRNIRKVRGPPVSCIKR | 16 |
| hLF4 | KCFQWQRNXRKVRGPPVSCIKR, whereby X is norvaline | 17 |

TABLE 1-continued

Exemplary Membrane Penetrating Peptide (MPP) sequences

| Name | Peptide Sequence | SEQ ID NO: |
|---|---|---|
| hLF5 | KCFQWQRNLRKVRGPPVSCIKR | 18 |
| hLF6 | KCFQWQRNXRKVRGPPVSCIKR, whereby X is norleucine | 19 |
| hLF7 | CFQWQRNVRKVRGPPVSC | 20 |
| hLF8 | CFQWQRNIRKVRGPPVSC | 21 |
| hLF9 | CFQWQRNXRKVRGPPVSC, whereby X is norvaline | 22 |
| hLF10 | CFQWQRNLRKVRGPPVSC | 23 |
| hLF11 | CFQWQRNXRKVRGPPVSC, whereby X is norleucine | 24 |
| hLF12 | FQWQRNVRKVRGPPVS | 25 |
| hLF13 | FQWQRNIRKVRGPPVS | 26 |
| hLF14 | FQWQRNVRKVRGPPVS, whereby X is norvaline | 27 |
| hLF15 | FQWQRNLRKVRGPPVS | 28 |
| hLF16 | FQWQRNXRKVRGPPVS, whereby X is norleucine | 29 |
| hLF17 | FQWQRNVRKVR | 30 |
| hLF18 | FQWQRNIRKVR | 31 |
| hLF19 | FQWQRNXRKVR, whereby X is norvaline | 32 |
| hLF20 | FQWQRNLRKVR | 33 |
| hLF21 | FQWQRNXRKVR, whereby X is norleucine | 34 |
| hLF22 | CFQWQRNMRKVRGPPVSC | 35 |
| C45D18 | DTWAGVEAIIRILQQLLFIHFRIGCRH | 36 |
| LR20 | RILQQLLFIHFRIGCRHSRI | 37 |
| LR17 | RILQQLLFIHFRIGCRH | 38 |
| LR15 | RILQQLLFIHFRIGC | 39 |
| LR15DL | RIFIHFRIGC | 40 |
| LR8DHF | RIFIRIGC | 41 |
| LR8DHFRI | RIFIGC | 42 |
| LR8DRIHF | FIRIGC | 43 |
| Tat | YGRKKRRQRRR | 44 |
| ΔNTat | RKKRRQRRR | 45 |
| Antp | RQIKIWFQNRRMKWKK | 46 |
| bLF | PEWFKCRRWQWRMKKLGA | 47 |
| bLF2 | KCRRWQWRMKKLGAPSITCVRR | 48 |
| bLF3 | CRRWQWRMKKLGAPSITC | 49 |
| LF1 | FQWQRNMRKVRGPPVS | 50 |

TABLE 1-continued

Exemplary Membrane Penetrating Peptide (MPP) sequences

| Name | Peptide Sequence | SEQ ID NO: |
|---|---|---|
| LF2 | FQWQRNMRKVR | 51 |
| SynB1 | RGGRLSYSRRRFSTSTGR | 52 |
| Penetratin PTD | RQIKWFQNRRMKWKK | 53 |
| PTD-4 | PIRRRKKLRRLK | 54 |
| PTD-5 | RRQRRTSKLMKR | 55 |
| FHV Coat-(35-49) | RRRRNRTRRNRRRVR | 56 |
| BMV Gag-(7-25) | KMTRAQRRAAARRNRWTAR | 57 |
| HTLV-II Rex-(4-16) | TRRQRTRRARRNR | 58 |
| D-Tat | GRKKRRQRRRPPQ | 59 |
| R9-Tat | GRRRRRRRRRPPQ | 60 |
| Transportan | GWTLNSAGYLLGKINLKALAALAKKIL | 61 |
| MAP | KLALKLALKLALALKLA | 62 |
| SBP | MGLGLHLLVLAAALQGAWSQPKKKRKV | 63 |
| FBP | GALFLGWLGAAGSTMGAWSQPKKKRKV | 64 |
| MPG | GALFLGFLGAAGSTMGAWSQPKKKRKV | 65 |
| MPG(ΔNLS) | GALFLGFLGAAGSTMGAWSQPKSKRKV | 66 |
| Pep-1 | KETWWETWWTEWSQPKKKRKV | 67 |
| Pep-2 | KETWFETWFTEWSQPKKKRKV | 68 |

TABLE 2

Exemplary Linker (L) peptide sequences

| Name | Peptide Sequence | SEQ ID NO: |
|---|---|---|
| Linker 1 | GGGSGGGSGGGS | 69 |
| Linker 2 | GGSGGSGGSGGS | 70 |
| Linker 3 | GGGGGGGGGGGG | 71 |
| Linker 4 | GGGSGGGSGGGSGGGS | 72 |
| Linker 5 | GGGAGGGAGGGAGGGA | 73 |
| Linker 6 | GGGAGGGSGGGAGGGS | 74 |
| Linker 7 | AAAAAAAAAA | 75 |
| Linker 8 | AAASAAASAAAS | 76 |
| Linker 9 | AAASAAASAAASAAAS | 77 |
| Linker 10 | AAGSAAGSAAGS | 78 |
| Linker 11 | AGGSAGGSAGGS | 79 |
| Linker 12 | GGGTGGGTGGGT | 80 |
| Linker 13 | AAATAAATAAAT | 81 |

TABLE 3

Exemplary cationic polypeptide (CP) sequences

| Name | Peptide Sequence | SEQ ID NO: |
|---|---|---|
| CP1 | RRRRRRRRRR | 82 |
| CP2 | RRRRRRRRRRRRRRR | 83 |
| CP3 | RRRRRRRRRRRRRRRRRRRR | 84 |
| CP4 | KKKKKKKKKK | 85 |
| CP5 | RRRRHRRRRHRRRRH | 86 |
| CP6 | RRRRKRRRRKRRRRK | 87 |
| CP7 | KKKKRKKKKRKKKKR | 88 |

Table 4 set forth various peptide sequences that can be used in the practice of the present invention, though it will be understood by one of ordinary skill level in the art that the list of peptide sequences in Table 4 is provided by way of example only, and is not meant to limit the scope of the invention solely to those sequences explicitly spelled. On the contrary, it will be readily apparent to such a person that, based on the teachings set forth above with regard to the A, L and B regions of the inventive peptides, a large number of peptides that are potentially useful in the practice of the invention set forth in herein is possible. Moreover, it is well within the purview of the skilled artisan to determine whether a given peptide sequence falls within the scope of the invention using standard techniques in the art, without requiring undue experimentation. Moreover, it will be appreciated that various variants of the peptide sequences appearing in Table 4 also fall within the scope of the invention, as long as such variants satisfy the structural and functional characteristics set forth above. Variants of the peptide sequences appearing in Table 4, or of any other candidate peptides not explicitly recited in Table 4 but satisfying the structural and functional requirements set forth above can include deletions, insertion, substitutions with naturally occurring or non-proteinogenic amino acids.

TABLE 4

Exemplary Non-Naturally Occurring Peptides

| Name | Peptide Sequence | SEQ ID NO: |
|---|---|---|
| Peptide 1 | SRRARRSPRESGKKRKRKRGGGS GGGSGGGSRRRRRRRRRR | 89 |
| Peptide 2 | CGAYDLRRRERQSRLRRRERQSR GGGSGGGSGGGSRRRRRRRRRRRR | 90 |
| Peptide 3 | GYGRKKRRGRRRTHRLPGGGSGG GSGGGSRRRRRRRRRRRR | 91 |

TABLE 4-continued

Exemplary Non-Naturally Occurring Peptides

| Name | Peptide Sequence | SEQ ID NO: |
|---|---|---|
| Peptide 4 | IGCRHGGGSGGGSGGGSRRRRRRRRRR | 92 |
| Peptide 5 | CGNKRTRGCGGGSGGGSGGGSRRRRRRRRRR | 93 |
| Peptide 6 | CAGRRSAYCGGGSGGGSGGGSRRRRRRRRRR | 94 |
| Peptide 7 | GSGKKGGKKHCQKYGGGSGGGSGGGSRRRRRRRRRRR | 95 |
| Peptide 8 | YKQCHKKGGKKGSGGGSGGGSGGGSRRRRRRRRRRR | 96 |
| Peptide 9 | KMTRAQRRAAARRNRWTARGCGGGSGGGSGGGSRRRRRRRRRRR | 97 |
| Peptide 10 | RRHHCRSKAKRSRHHGGGSGGGSGGGSRRRRRRRRRRR | 98 |
| Peptide 11 | KCFQWQRNMRKVRGPPVSCIKRGGGSGGGSGGGSRRRRRRRRRRR | 99 |
| Peptide 12 | PEWFKCRRWQWRMKKLGAGGSGGSGGSGGSKKKKKKKKKK | 100 |
| Peptide 13 | KCFQWQRNVRKVRGPPVSCIKRAAGSAAGSAAGSKKKKRKKKKRKKKKR | 102 |
| Peptide 14 | GRRHHCRSKAKRSRHHGGGSGGGSGGGSRRRRRRRRRR | 103 |
| Peptide 15 | CGNKRTRGCGGGGGGGGGRRRRKRRRRKRRRRK | 104 |
| Peptide 16 | KCRRWQWRMKKLGAPSITCVRR | 105 |
| Peptide 17 | CYGRKKRRQRRRRRRRRRRRRRRRRRRRRR | 106 |
| Peptide 18 | RQIKWFQNRRMKWKKAAASAAASAAASRRRKKKRRRKKK | 107 |

In some embodiments, the peptide sequence of A is between 5 to about 50 amino acids, and A is characterized in that it improves delivery of a molecule into a cell in the presence of a cationic lipid-based transfection reagent by at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more.

In some embodiments, A is at least 50%, at least 55%, at least 60%, at least 65%, at least 70%, at least 75%, at least 80%, at least 85%, at least 90%, at least 95% similar to any one of the peptide sequences set forth in Table 1, and A is characterized in that it improves delivery of a molecule into a cell by at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more.

In some embodiments, A may comprise any one or more of the peptide sequences set forth in SEQ ID NO. 1-68, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In some embodiments, A may comprise any one or more of the peptide sequences set forth in SEQ ID NO. 14-35, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In some embodiments, A may comprise any one or more of the peptide sequences set forth in SEQ ID NO. 37-43, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In some embodiments, A may comprise any one or more of the peptide sequences set forth in SEQ ID NO. 44, 45, 46, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In some embodiments, A may comprise any one or more of the peptide sequences set forth in SEQ ID NO. 52-68, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In some embodiments, A may comprise any one or more of the peptide sequences set forth in SEQ ID NO. 1, SEQ ID NO. 3, SEQ ID NO. 4, SEQ. ID. NO. 5, SEQ ID NO. 13, and SEQ ID NO. 14, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In one aspect of the invention, the non-naturally occurring peptide A may comprise any one or more of the peptide sequences set forth in Table 4, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In one aspect of the invention, the non-naturally occurring peptide A may comprise any one or more of the peptide sequences set forth in SEQ. ID. NO. 89-107, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In one aspect of the invention, the non-naturally occurring peptide A may comprise any one or more of the peptide sequences set forth in SEQ. ID. NO. 89-96, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

In one aspect of the invention, the non-naturally occurring peptide A may comprise any one or more of the peptide sequences set forth in SEQ. ID. NO. 89, 92, 98, 103 or 106, or a variant thereof being at least 50%, at least 55%, at least 60%, at least 65%, at least 70%, at least 75%, at least 80%, at least 85%, at least 90%, at least 95% similar thereto and having at least 10% or more, at least 15% or more, at least 20% or more, at least 25% or more, at least 30% or more, at least 35% or more, at least 40% or more, at least 45% or more, at least 50% or more, at least 55% or more, at least 60% or more, at least 65% or more, at least 70% or more, at least 75% or more, at least 80% or more, at least 85% or more, at least 90% or more, at least 95% or more, at least 100%, at least 200% or more, at least 250% or more, at least 300% or more, at least 350% or more, at least 400% or more, at least 500% or more, at least 600% or more, at least 700% or more, at least 800% or more, at least 900% or more, at least 1000% or more at least 1500% or more or at least 2000% or more of the activity thereof.

Transfection Enhancing Agents

The complexes formed between the non-naturally occurring peptide, the nucleic acid and the transfection agent may be further enhanced by inclusion of moieties such as proteins or peptides that function for nuclear or other subcellular localization, function for transport or trafficking, are receptor ligands, comprise cell-adhesive signals, cell-targeting signals, cell-internalization signals or endocytosis signals as well as peptides or functional portions thereof of viral fusogenic proteins of enveloped viruses, of viral nuclear localization signals, of receptor-ligands, of cell adhesion signals, of cell-targeting signals or of internalization- or endocytosis-triggering signals.

The complex may also optionally contain a transfection enhancing agent, such as a nuclear localization protein or peptide, a fusogenic peptide or protein, receptor-ligand peptide or protein, a transport peptide or protein, or a viral peptide or protein that is distinct in amino acid sequence from the non-naturally occurring peptides of the present invention. The suitable viral peptide may be derived from a virus such as an influenza virus, a vesicular stomatitis virus, an adenovirus, an alphavirus, a Semliki Forest Virus, a hepatitis virus, a herpes virus, an HIV virus, or a simian virus. The transfection enhancing agent may also be, for example, insulin, a transferrin, a epidermal growth factor, a fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a histone protein, an arginine rich cell permeability protein, a high mobility group protein, and invasin protein, and internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bacteriacidal-permability-increasing protein, a nisin, a buforin, or fragments thereof. The transfection enhancing agent may be chloroquine, a lysosomotrophic compound or any derivatives, variants, or combinations thereof. The transfection agent may contain multimers of the same or different peptides or proteins.

Any proteins or peptides (or fragments or portions thereof) of the invention may be used in accordance with this invention, either singly or in combination with other proteins or peptides. In a preferred aspect, two or more, three or more, four or more, five or more, six or more, etc. proteins and/or peptides are used in the invention. Additionally, such single or multiple proteins and/or peptides may be used in combination with one or more, two or more, three or more, four or more, five or more, six or more, etc. transfection agents. In another preferred aspect, at least two peptides and/or proteins are used in combination with a transfection agent, preferably at least two transfection agents such as lipids, and/or polycations such as dendrimers or PEI.

Further embodiments of the present invention are directed to transfection complexes containing the non-naturally occurring peptides described above in combination with one or more transfection reagents, which transfection reagents may include one or more cationic lipids, and optionally one or more helper lipids. In some embodiments, a transfection complex may include a cargo to be delivered to the interior of a cell, or optionally may be administered to an animal or to a human patient who would benefit from the administration thereof. Preferred though non-limiting cargo molecules suitable for use with the present invention include nucleic acid molecules such as DNA molecules or RNA molecules. Suitable DNA molecules may include a DNA molecule having an expressible nucleic acid sequence, such as an expression vector or a cDNA molecule comprising an open reading frame encoding a protein. Other suitable molecules that may function as suitable cargo in the practice of the present invention include RNA molecules, such as an mRNA molecule or an RNAi molecule.

Methods of Making Peptides:

The non-naturally occurring peptides of the present invention can be produced by any previously known peptide synthesis methods known to those possessing ordinary skill level in the art, without limitation, including recombinant methods or peptide synthesis chemistry, such as, e.g., sold phase peptide synthesis. The solid phase synthesis method (Marrifield, J. Am. Chem. Soc., 85, 2149-2154, 1963) can be noted as merely an example of such a peptide synthesis method. At present the peptide can be produced simply and in a relatively short period of time using an automated, general purpose peptide synthesizer based on those principles. Additionally, the peptide can be produced using well-known recombinant protein production techniques, which techniques are widely known to the skilled artisan.

Transfection Reagents

The present invention also provides a transfection complex comprising, in non-covalent association, a non-naturally occurring peptide according to the present invention as described above and incorporated herein, at least one cargo molecule as defined above and incorporated herein, at least one transfection reagent as defined above and incorporated herein.

In certain preferred though non-limiting embodiments, a transfection reagent selected for use in the practice of the present invention may include one or more cationic lipids. In some embodiments, the one or more cationic lipids may optionally include at least one, optionally more than one neutral lipid or helper lipid.

In some embodiments, a transfection reagent may include one or more lipids of which one or more can be cationic lipids. In some embodiments, the transfection reagent may include a mixture of neutral and cationic lipids. In some embodiments, the transfection reagent may include one or more peptides and/or proteins which are distinct from the non-naturally occurring peptide of the present invention and which can be provided alone or in admixture with one or more lipids. By way of non-limiting example, one such peptide may include a reagent such as, e.g., PLUS™ Reagent (Life Technologies, Carlsbad, CA). In some preferred embodiments, the transfection reagent forms a non-covalent complex with the macromolecule/cargo to be delivered to the interior of the cell, the non-naturally occurring peptides of the present invention, and optionally the one or more helper or neutral lipids. In preferred embodiments, transfection complexes made in accordance with the methods described herein may have a net positive charge, thereby facilitating the interaction of the transfection complex with the cell membrane.

In some embodiments, a transfection reagent suitable for use in accordance with the present invention may be any material, formulation or composition known to those of skill in the art that facilitates the entry of a macromolecule into a cell. In some embodiments, the transfection reagent can be any compound and/or composition that increases the uptake of one or more nucleic acids or other cargo molecules into one or more target cells.

A variety of transfection reagents are known to those skilled in the art. Suitable transfection reagents can include, but are not limited to, one or more compounds and/or compositions comprising cationic polymers such as polyethyleneimine (PEI), polymers of positively charged amino acids such as polylysine and polyarginine, positively charged dendrimers and fractured dendrimers, cationic β-cyclodextrin containing polymers (CD-polymers), DEAE-dextran and the like. In some embodiments, a reagent for the introduction of macromolecules into cells can comprise one or more lipids which can be cationic lipids and/or neutral lipids. Preferred lipids include, but are not limited to, N-[1-(2,3-dioleyloxy)propyl]-N,N,N-trimethylamonium chloride (DOTMA), dioleoylphosphatidylcholine (DOPE), 1,2-Bis(oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC), cholesteryl (4'-trimethylammonio) butanoate (ChoTB), cetyltrimethylammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dimyristyloxypropyl-3-dimethyl-hydroxyethyl ammonium bromide (DMRIE), O,O'-didodecyl-N-[p(2-trimethylammonioethyloxy)benzoyl]-N,N,N-trimethylam-monium chloride, spermine conjugated to one or more lipids (for example, 5-carboxyspermylglycine dioctadecylamide (DOGS), $N,N^{I},N^{II}$, $N^{III}$-tetramethyl-N,$N^{I}$,$N^{II}$,$N^{III}$-tet-rapalmitylspermine (TM-TPS) and dipalmitoylphasphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trilysyl-alanyl-TRIS mono-, di-, and tri-palmitate, (3β-[N-(N',N'-dimethylaminoethane)-carbamoyl] cholesterol (DC-Chol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido)ethyl]-N,N-dimethyl-1-propanamin-iniumtrifluoroacetate (DOSPA) and combinations thereof.

Those skilled in the art will appreciate that certain combinations of the above mentioned lipids have been shown to be particularly suited for the introduction of nucleic acids into cells for example a 3:1 (w/w) combination of DOSPA and DOPE is available from Life Technologies Corporation, Carlsbad, Calif. under the trade name LIPOFECTAMINE™, a 1:1 (w/w) combination of DOTMA and DOPE is available from Life Technologies Corporation, Carlsbad, Calif. under the trade name LIPOFECTIN®, a 1:1 (M/M) combination of DMRIE and cholesterol is available from Life Technologies Corporation, Carlsbad, Calif. under the trade name DMRIE-C reagent, a 1:1.5 (M/M) combination of TM-TPS and DOPE is available from Life Technologies Corporation, Carlsbad, Calif. under the trade name CELLFECTIN® and a 1:2.5 (w/w) combination of DDAB and DOPE is available from Life Technologies Corporation, Carlsbad, Calif. under the trade name LIPOFECTACE®. In addition to the above-mentioned lipid combinations, other formulations comprising lipids in admixture with other compounds, in particular, in admixture with peptides and proteins comprising nuclear localization sequences, are known to those skilled in the art. For example, see international application no. PCT/US99/26825, published as WO 00/27795, both of which are incorporated by reference herein.

Lipid aggregates such as liposomes have been found to be useful as agents for the delivery of macromolecules into cells. In particular, lipid aggregates comprising one or more cationic lipids have been demonstrated to be extremely efficient at the delivery of anionic macromolecules (for example, nucleic acids) into cells. One commonly used cationic lipid is N-[1-(2,3-dioleoyloxy)propyl]-N,N,N-trimethylammonium chloride (DOTMA). Liposomes comprising DOTMA alone or as a 1:1 mixture with dioleoylphosphatidylethanolamine (DOPE) have been used to introduce nucleic acids into cells. A 1:1 mixture of DOTMA:DOPE is commercially available from Life Technologies Corporation, Carlsbad, Calif. under the trade name of LIPOFECTIN™. Another cationic lipid that has been used to introduce nucleic acids into cells is 1,2-bis(oleoyl-oxy)-3-3-(trimethylammonia) propane (DOTAP). DOTAP differs from DOTMA in that the oleoyl moieties are linked to the propylamine backbone via ether bonds in DOTAP whereas they are linked via ester bonds in DOTMA. DOTAP is believed to be more readily degraded by the target cells. A structurally related group of compounds wherein one of the methyl groups of the trimethylammonium moiety is replaced with a hydroxyethyl group are similar in structure to the Rosenthal inhibitor (RI) of phospholipase A (see Rosenthal, et al., (1960) J. Biol. Chem. 233:2202-2206.). The RI has stearoyl esters linked to the propylamine core. The dioleoyl analogs of RI are commonly abbreviated DOR1-ether and DOR1-ester, depending upon the linkage of the lipid moiety to the propylamine core. The hydroxyl group of the hydroxyethyl moiety can be further derivatized, for example, by esterification to carboxyspermine.

Another class of compounds which has been used for the introduction of macromolecules into cells comprise a carboxyspermine moiety attached to a lipid (see, Behr, et al., (1989) Proceedings of the National Academy of Sciences, USA 86:6982-6986 and EPO 0 394 111). Examples of compounds of this type include dipalmitoylphosphatidylethanolamine 5-carboxyspermylamide (DPPES) and 5-carboxyspermylglycine dioctadecylamide (DOGS). DOGS is commercially available from PROMEGA™, Madison, Wis. under the trade name of TRANSFECTAM™.

A cationic derivative of cholesterol (3β-[N-(N',N'-dimethylaminoethane)-carbamoyl] cholesterol, DC-Chol) has been synthesized and formulated into liposomes with DOPE (see Gao, et al., (1991) BBRC 179(1):280-285.) and used to introduce DNA into cells. The liposomes thus formulated were reported to efficiently introduce DNA into the cells with a low level of cellular toxicity. Lipopolylysine, formed by conjugating polylysine to DOPE (see Zhou, et al., (1991) BBA 1065:8-14), has been reported to be effective at introducing nucleic acids into cells in the presence of serum.

Other types of cationic lipids that have been used to introduce nucleic acids into cells include highly packed polycationic ammonium, sulfonium and phosphonium lipids such as those described in U.S. Pat. Nos. 5,674,908 and 5,834,439, and international application no. PCT/US99/26825, published as WO 00/27795.

One non-limiting transfection reagent for delivery of macromolecules in accordance with the present invention is LIPOFECTAMINE 2000™ or derivatives thereof which is available from Life technologies (see U.S. international application no. PCT/US99/26825, published as WO 00/27795).

Another preferred though non-limiting transfection reagent suitable for delivery of macromolecules to a cell is EXPIFECTAMINE™ or derivatives thereof.

Other suitable transfection reagents include LIPOFECTAMINE® RNAiMAX, LIPOFECTAMINE® LTX, OLIGOFECTAMINE® CELLFECTIN™, INVIVOFECTAMINE®, INVIVOFECTAMINE® 2.0, and any of the lipid reagents or formulations disclosed in U.S. Patent Appl. Pub. No. 2012/0136073, by Yang et al. (incorporated herein by reference thereto). A variety of other transfection reagents are known to the skilled artisan and may be evaluated for the suitability thereof to the transient transfection systems and methods described herein.

Various preferred though non-limiting cationic lipids and transfection reagent suitable for use with the present invention will now be described in greater detail below. It should be noted however, that the explicit disclosure of one or more specific cationic lipids, or one or more genera of cationic lipids, is not meant to preclude the use of other reagents or lipids that are capable of being used in conjunction with the non-naturally occurring peptides of the present invention, and that the selection of alternative cationic lipids or transfections reagents, and the use thereof in the context of the present invention, is well within the purview of the skilled art, and that such a person may readily use such a reagent without departing from the spirit and scope of the present invention.

Some embodiments of the present invention provide lipid aggregates comprising one or more non-naturally occurring peptides described above in combination with one or more cationic lipids. Without being limited to or bound by any theory or mechanistic explanation for the performance of the composition forming the basis of the present invention, and solely in the interest of providing complete disclosure thereof, it is believed that the non-naturally occurring peptides of the present invention, when used in combination with one or more transfection reagents, in particular with one or more cationic transfection lipids, improve ability of a transfection complex comprising a lipid aggregate and the cargo molecule to be delivered to the interior of a cell. The use of cationic lipids, optionally in conjunction with one or more helper lipids or one or more neutral lipids, may allow for greater encapsulation of the cargo molecule by the lipid aggregate and further may assist with the fusion of the liposomal lipid aggregate with the target cell membrane, thereby improving enhancing the delivery of the cargo molecule.

Cationic lipids useful for use in the formation of transfection complexes of the present invention can be either monovalent or polyvalent cationic lipids or a mixture of cationic lipids. Of particular interest are cationic lipids recognized in the art as useful in transfection methods, including, but not limited to, DOTMA, DOTAP, DDAB, DMRIE, DOSPA, DOSPER, TMTPS, DHMS, DHDMS and their analogs or homologs. Optionally, the lipid aggregate may further comprise at least one additional helper lipid. Helper lipids are known in the art and include, but are not limited to, neutral lipids, preferably selected from the group consisting of DOPE, DOPC and cholesterol. Optionally, transfection complexes of the present invention may include commercially available transfection reagents containing cationic lipids such as Lipofectin®, LIPOFECTAMINE™ RNAiMAX and LIPOFECTAMINE™2000, LIPOFECTAMINE® 3000, LIPOFECTAMINE® LTX (Life Technologies Corporation, Carlsbad, CA).

A further embodiment of the invention provides a cationic lipid aggregate, comprising one or more cationic lipids, optionally one or more helper lipids, and one or more cargo molecules complexed with one or more of the non-naturally occurring peptides described above. The cargo molecule may be any substance that is to be conveyed to the interior of a cell, either in culture in a laboratory or in a tissue in an animal or a human. The cargo may, depending on the application, be a macromolecule such as a nucleic acid, a protein, or a peptide, or may be a drug or other organic small molecule. In some embodiments, the preferred cargo for forming a transfection complex is a nucleic acid such as, e.g., deoxyribonucleic acid (DNA) and ribonucleic acid (RNA). In some embodiments, the preferred cargo may be a DNA molecule. The DNA can be either linear DNA or circular DNA, such as DNA in the form of a circular plasmid, an episome or an expression vector. In certain preferred though non-limiting embodiments, the term macromolecule refers to complementary DNA (cDNA) have an expressible nucleic acid sequence, including at least one open reading frame operably linked to one or more nucleic acid sequence required for the transcription of an mRNA from the expressible nucleic acid sequence. In other embodiments, a preferred cargo may be an RNA molecule. The RNA molecule may be any type of RNA molecule, without limitation, including but not limited to an mRNA, an siRNA, an miRNA, an antisense RNA, a ribozyme, or any other type or species of RNA molecule familiar to those skilled in the art without limitation, that would be sought to be delivered to the interior of a cell.

Preferably the transfection complex of the present invention may include a non-naturally occurring peptide as described above, at least one cargo, at least on cationic lipid, and optionally at least one helper lipid. The transfection complex, one formed, is stable in aqueous solution and can either be contacted with a cell or a tissue in a human or an animal immediately after being formed, or can be stored for a period prior to being contacted with the cell or tissue. The transfection complex is stable and can be stored for a time period of at least 30 minutes, at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year. It is understood, that the storage period can be between any of these time periods, for example between 31 minutes and 1 hour or between 1 hour and 24 hours.

Generally, the transfection complexes of this invention can comprise any cationic lipid, either monovalent or polyvalent, including those in known transfection reagents (see Table 5). Cationic lipids include saturated and unsaturated alkyl and alicyclic ethers and esters of amines, amides or derivatives thereof. Straight-chain and branched alkyl and alkene groups of cationic lipids can contain from 1 to about 25 carbon atoms. Preferred straight-chain or branched alkyl or alkene groups have six or more carbon atoms. More preferred straight-chain or branched alkyl or alkene groups have eight to about twenty carbon atoms. Alicyclic groups can contain from about 6 to 30 carbon atoms, and more preferably eight to twenty carbon atoms. Preferred alicyclic groups include cholesterol and other steroid groups. Cationic lipids can be prepared with a variety of counter ions (anions) including among others: Cl—, Br—, I—, F—, acetate, trifluoroacetate, sulfate, nitrite, triflate, and nitrate.

In the lipid aggregates of this invention, cationic lipids can optionally be combined with non-cationic lipids, preferably neutral lipids, to form lipid aggregates that bind to the modified-peptide-nucleic acid complex. Neutral lipids useful in this invention as helper lipids include, among many others: lecithins (and derivatives thereof); phosphotidylethanolamine (and derivatives thereof); phosphatidylethanolamines, such as DOPE (dioleoylphosphatidylethanolamine), DphPE (diphytanoylphosphatidylethanolamine), DPPE (dipalmitoylphosphatidylethanolamine), dipalmiteoylphosphatidyl-ethanolamine, POPE (palmitoyloleoylphosphatidylethanolamine) and distearoyl-phosphatidylethanolamine; phosphotidylcholine; phosphatidylcholines, such as DOPC (dioleoylphosphidylcholine), DPPC (dipalmitoylphosphatidylcholine) POPC (palmitoyloleoylphosphatidylcholine) and distearoylphosphatidylcholine; phosphatidyl-glycerol; phosphatidylglycerols, such as DOPG (dioleoylphosphatidylglycerol), DPPG (dipalmitoylphosphatidylglycerol), and distearoylphosphatidylglycerol; phosphatidyl-serine (and derivatives thereof); phosphatidylserines, such as dioleoyl- or dipalmitoylphosphatidylserine; diphosphatidylglycerols; fatty acid esters; glycerol esters; sphingolipids; cardolipin; cerebrosides; and ceramides; and mixtures thereof. Neutral lipids also include cholesterol and other 3130H-sterols as well as derivatives thereof.

The following patent documents, patent applications, or references are incorporated by reference herein in their entirety and in particular for their disclosure of transfection agents containing cationic and neutral (helper) lipids which may be used to comprise the lipid aggregates of the present invention in conjunction with the cationic lipids: U.S. Pat. Nos. 6,075,012; 6,020,202; 5,578,475; 5,736,392; 6,051,429; 6,376,248; 5,334,761; 5,316,948; 5,674,908; 5,834,439; 6,110,916; 6,399,663; 6,716,882; 5,627,159; PCT/US/2004/000430, published as WO 04063342 A2; PCT/US/9926825, published as WO 0027795 A1; PCT/US/04016406, published as WO 04105697; and PCT/US2006/019356, published as WO 07130073 A2. Table 5 also lists transfection agents comprising cationic lipids and neutral lipids which may be used to comprise the lipid aggregates of the present invention in conjunction with the cationic lipids.

TABLE 5

| Transfection Agent | Description | Patents and/or Citations | available from |
|---|---|---|---|
| Non-limiting Examples of Transfection Reagents | | | |
| BMOP | N-(2-bromoethyl)-N,N-dimethyl-2,3-bis(9-octadecenyloxy)-propanaminium bromide) | | |
| BMOP:DOPE | 1:1 (wt/wt) formulation of N-(2-bromoethyl)-N,N-dimethyl-2,3-bis(9-octadecenyloxy)-propanaminium bromide) (BMOP) and DOPE | Walzem et al., Poult Sci. 76: 882-886, 1997. Transfection of avian LMH-2A hepatoma cells with cationic lipids. | |
| Cationic polysaccharides | Cationic polysaccharides | Published U.S. patent application 2002/0146826 | |
| CellFECTIN ® | 1:1.5 (M/M) formulation of N, NI, NII, NIII-tetramethyl-N, NI, NII, NIII-tetrapalmitylspermine (TM-TPS) and dioleoyl phosphatidylethanolamine (DOPE) | U.S. Pat. Nos. 5,674,908, 5,834,439 and 6,110,916 | Invitrogen |
| CTAB:DOPE | formulation of cetyltrimethyl-ammonium bromide (CATB) and dioleoylphosphatidylethanol-amine (DOPE) | | |
| Cytofectin GSV | 2:1 (M/M) formulation of cytofectin GS* and dioleoyl phosphatidyl-ethanolamine (DOPE) | | (*Cytofectin GS corresponds to Gilead Sciences' GS 3815) |
| DC-Cholesterol (DC-Chol) | 3,β-N,(N',N'-dimethylaminoethane)-carbamo-yl]cholesterol | | |
| DC-Chol:DOPE | formulation of 3,β-N,(N',N'-dimethylaminoethane)-carbamo-yl]cholesterol (DC-Chol) and dioleoyl phosphatidyl-ethanolamine (DOPE) | Gao et al., Biochim. Biophys. Res. Comm. 179: 280-285, 1991 | |
| DC-6-14 | O,O'-Ditetradecanoyl-N-(alpha-trimethylammonioacetyl) diethan olamine chloride | Kikuchi et al., Hum Gene Ther 10: 947-955, 1999. Development of novel cationic liposomes for efficient gene transfer into peritoneal disseminated tumor. | |
| DCPE | Dicaproylphosphtidylethanol-amine | | |

TABLE 5-continued

Non-limiting Examples of Transfection Reagents

| Transfection Agent | Description | Patents and/or Citations | available from |
|---|---|---|---|
| DDPES | Dipalmitoylphosphatidyl-ethanolamine 5-carboxyspermylamide | Behr et al., *Proc. Natl. Acad. Sci. USA* 86: 6982-6986, 1989. Efficient gene transfer into mammalian primary endocrine cells with lipopolyamine-coated DNA; EPO published patent application 0 394 111 | |
| DDAB | didoceyl methylammonium bromide | | |
| Dextran and dextran derivatives or conjugates | DEAE-Dextran; Dextran sulfate | Mai et al., *J Biol Chem*. 277: 30208-30218, 2002. Efficiency of protein transduction is cell type-dependent and is enhanced by dextran sulfate. | |
| Diquaternary ammonium salts | (examples☺ N'N'-dioleyl-N,N'N"N'-tetramethyl-1,2-ethanediamine (TmedEce), N'N'-dioleyl-N,N'N"N'-tetramethyl-1,3-propanediamine (PropEce), N'N'-dioleyl-N,N'N"N'-tetramethyl-1,6-hexanediamine (HexEce), and their corresponding N'N'-dicetyl saturated analogues (TmedAce, PropAce and HexAce) | Rosenzweig et al., *Bioconjug Chem* 12: 258-263, 2001. Diquaternary ammonium compounds as transfection agents; U.S. Pat. No. 5,994,317 | Vical |
| DLRIE | dilauryl oxypropyl-3-dimethylhydroxy ethylammonium bromide | Felgner et al., *Ann NY Acad Sci* 772: 126-139, 1995. Improved cationic lipid formulations for in vivo gene therapy. | Vical |
| DMAP | 4-dimethylaminopyridine | | |
| DMPE | Dimyristoylphospatidyl-ethanol-amine | | |
| DMRIE | N-[1-(2,3 dimyristyloxy)propyl]-N,N-dimethyl-N-(2-hydroxyethyl) ammonium bromide | Konopka et al., *Biochim Biophys Acta* 1312: 186-96, 1996. Huma53mmuneno-deficiency virus type-1 (HIV-1) infection increases the sensitivity of macrophages and THP-1 cells to cytotoxicity by cationic liposomes. | |
| DMRIE-C | 1:1 formulation of N-[1-(2,3-dimyristyloxy)propyl]-N,N-dimethyl-N-(2-hydroxyethyl) ammonium bromide (DMRIE) and cholesterol | U.S. Pat. Nos. 5,459,127 and 5,264,618, to Felgner, et al. (Vical) | Invitrogen |
| DMRIE:DOPE | formulation of 1,2-dimyristyloxypropyl-3-dimethyl-hydroxyethyl ammonium bromide and dioleoyl phosphatidyl-ethanolamine (DOPE) | San et al., *Hum Gene Ther* 4: 781-788, 1993. Safety and short-term toxicity of a novel cationic lipid formulation for human gene therapy. | |

TABLE 5-continued

Non-limiting Examples of Transfection Reagents

| Transfection Agent | Description | Patents and/or Citations | available from |
|---|---|---|---|
| DOEPC | Dioleoylethyl-phosphocholine | | |
| DOHME | N-[1-(2,3-dioleoyloxy)propyl]-N-[1-(2-hydroxyethyl)]-N,N-dimethylammonium iodide | | |
| DOPC | Dioleoylphosphatidylcholine | | |
| DOPC:DOPS | 1:1 (wt %) formulation of DOPC (dioleoylphosphatidylcholine) and DOPS | | Avanti |
| DOSPA | 2,3-dioleoyloxy-N-[2-(sperminecarboxamidoethyl]-N,N-di-met-hyl-1-propanaminium trifluoroacetate | | |
| DOSPA:DOPE | Formulation of 2,3-dioleoyloxy-N-[2-(sperminecarboxamidoethyl]-N,N-di-met-hyl-1-propanaminium trifluoroacetate (DOSPA) and dioleoyl phosphatidyl-ethanolamine (DOPE) | Baccaglini et al., *J Gene Med* 3: 82-90, 2001. Cationic liposome-mediated gene transfer to rat salivary epithelial cells in vitro and in vivo. | |
| DOSPER | 1,3-Di-Oleoyloxy-2-(6-Carboxy-spermyl)-propylamid | Buchberger et al., *Biochemica* 2: 7-10, 1996. DOSPER liposomal transfection reagent: a reagent with unique transfection properties. | Roche |
| DOTAP | N-[1-(2,3-dioleoyloxy)propyl]-N,N,N-trimethyl-ammonium methylsulfate | | |
| DOTMA | N-[1-(2,3-dioleoyloxy)propyl]-n,n,n-trimethylammoniumchloride | | |
| DPEPC | Dipalmitoylethylphosphatidyl-choline | | |
| Effectene | (non-liposomal lipid formulation used in conjunction with a special DNA-condensing enhancer and optimized buffer) | Zellmer et al., *Histochem Cell Biol* 115: 41-47, 2001. Long-term expression of foreign genes in normal human epidermal keratinocytes after transfection with lipid/DNA complexes. | Qiagen |
| FuGENE ® 6 | | Wiesenhofer et al., *J Neurosci Methods* 92: 145-152, 1999. Improved lipid-mediated gene transfer in C6 glioma cells and primary glial cells using FuGene. | Roche |
| GAP-DLRIE:DOPE | N-(3-aminopropyl)-N,N-dimethyl-2,3-bis(dodecyloxy)-1-propaniminium bromide/dioleyl phosphatidylethanolamine | Stephan et al., *Hum Gene Ther* 7: 1803-1812, 1996. A new cationic liposome DNA complex enhances the efficiency of arterial gene transfer in vivo. | |

TABLE 5-continued

Non-limiting Examples of Transfection Reagents

| Transfection Agent | Description | Patents and/or Citations | available from |
|---|---|---|---|
| GS 2888 cytofectin | | Lewis et al., *Proc Natl Acad Sci USA* 93: 3176-3181, 1996. A serum-resistant cytofectin for cellular delivery of antisense oligodeoxynucleotides and plasmid DNA. | Gilead Sciences |
| Lipofectin ® | 1:1 (w/w) formulation of N-(1-2,3-dioleyloxypropyl)-N,N,N-triethylammonium (DOTMA) and dioleylphosphatidyl-ethanolamine (DOPE) | U.S. Pat. Nos. 4,897,355; 5,208,066; and 5,550,289. | Invitrogen |
| LipofectACE ™ | 1:2.5 (w/w) formulation of dimethyl dioctadecylammonium bromide (DDAB) and dioleoyl phosphatidylethanolamine (DOPE) | | Invitrogen |
| LIPOFECTAMINE ® LTX | | U.S. Pat. No. 7,915,230 | Invitrogen |
| LIPOFECTAMINE ™ | 3:1 (w/w) formulation of 2,3-dioleyloxy-N-[2(sperminecarbox-amido)ethyl]-N,N-dimethyl-1-propanaminium trifluoroacetate (DOSPA) and dioleoyl phosphatidylethanolamine (DOPE) | U.S. Pat. Nos. 5,334,761; and U.S. Pat. Nos. 5,459,127 and 5,264,618, to Felgner, et al. (Vical) | Invitrogen |
| LIPOFECTAMINE ™ 2000 | | | Invitrogen |
| LipofectAMINE PLUS ™ | | U.S. Pat. Nos. 5,736,392 and 6,051,429 | Invitrogen |
| LIPOFECTAMINE ® 3000 | | | Invitrogen |
| LipoTAXI ® | | | Stratagene |
| monocationic transfection lipids | (examples:) 1-deoxy-1-[dihexadecyl(meth-yl)ammonio]-D-xylitol; 1-deoxy-1-[methyl(di-tetradecyl)ammonio]-D-arabinitol; 1-deoxy-1-[dihexadecyl(meth-yl)ammonio]-D-arabinitol; 1-deoxy-1-[methyl(di-octadecyl)ammonio]-D-arabinitol | Banerjee et al., *J Med Chem* 44: 4176-4185, 2001. Design, synthesis, and transfection biology of novel cationic glycolipids for use in liposomal gene delivery. | |
| O-Chol | 3 beta[1-ornithinamide-carbamoyl] cholesterol | Lee et al., *Gene Ther* 9: 859-866, 2002. Intraperitoneal gene delivery mediated by a novel cationic liposome in a peritoneal disseminated ovarian cancer model. | |
| OliogfectAMINE ™ | | | Invitrogen |
| Piperazine based amphilic cationic lipids | Piperazine based amphilic cationic lipids | U.S. Pat. Nos. 5,861,397 and 6,022,874 | Vical |
| PolyFect | (activated-dendrimer molecules with a defined spherical architecture) | | Qiagen |
| Protamine | Protamine mixture prepared from, e.g., salmon, salt herring, etc.; can be supplied as, e.g., a sulfate or phosphate. | Sorgi et al., *Gene Ther* 4: 961-968, 1997. Protamine sulfate enhances lipid-mediated gene transfer. | Sigma |

TABLE 5-continued

| Transfection Agent | Description | Patents and/or Citations | available from |
|---|---|---|---|
| SuperFect | (activated-dendrimer molecules with a defined spherical architecture) | Tang et al., Bioconjugate Chem. 7: 703, 1996. In vitro gene delivery by degraded polyamidoamine dendrimers.; published PCT applications WO 93/19768 and WO 95/02397 | Qiagen |
| Tfx ™ | N,N,N',N'-tetramethyl-N,N'-bis(2-hydroxyethyl)-2,3-di(oleoyloxy)-1,4-butanediammonium iodide] and DOPE | | Promega |
| TransFast ™ | N,N [bis (2-hydroxyethyl)-N-methyl-N-[2,3-di(tetradecanoyloxy) propyl] ammonium iodide and DOPE | | Promega |
| TransfectAce | | | Invitrogen |
| TRANSFECTAM ™ | 5-carboxylspermylglycine dioctadecylamide (DOGS) | Behr et al., Proc. Natl. Acad. Sci. USA 86: 6982-6986, 1989; EPO Publication 0 394 111 | Promega |
| TransMessenger | (lipid-based formulation that is used in conjunction with a specific RNA-condensing enhancer and an optimized buffer; particularly useful for mRNA transfection) | | Qiagen |
| Vectamidine | 3-tetradecylamino-N-tert-butyl-N'-tetradecylpropionamidine (a.k.a. diC14-amidine) | Ouahabi et al., FEBS Lett 414: 187-92, 1997. The role of endosome destabilizing activity in the gene transfer process mediated by cationic lipids. | |
| X-tremeGENE ™ | | | Roche |

In some preferred though non-limiting embodiments, lipid aggregates can include at least a first cationic lipid and optionally at least a first neutral lipid, wherein said lipid aggregate is suitable for forming a cationic complex with a nucleic acid under aqueous conditions, wherein said the cationic lipids have the structure:

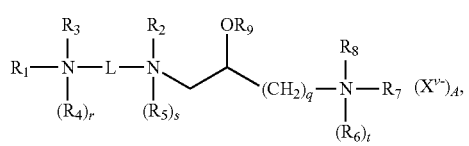

(Formula (I))

and salts thereof;
where:
  $R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where $R_1$ is $(CH_2)_q N(R_6)_t R_7 R_8$;

$R_3$ and $R_4$, independently, are hydrogens, or alkyl, alkenyl or alkynyl groups having from 8 to 30 carbon atoms and optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

q is an integer ranging from 1 to 6, inclusive;

$X^{v-}$ is an anion, where v is the valency of the anion and A is the number of anions;

L is a divalent organic radical capable of covalently linking the two nitrogens selected from: $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{—(CH_2)_k—Y—(CH_2)_m\}_p$, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups.

The synthesis of these compounds and methods for the preparation of lipid aggregates incorporating same may be achieved by any means known to those skilled in the art without limitation. Exemplary though non-limiting methods to synthesize such compounds, and methods for the formation of lipid aggregates incorporating same, may be found in, for example, U.S. Pat. No. 7,166,745 and PCT Publication No. WO 00/27795, both of which are expressly incorporated by reference in their entirety as though fully set forth herein.

In some embodiments, the lipid aggregates that form the basis of the present invention may further optionally include one, optionally more than one additional cationic lipid selected from the list consisting of TMTPS, DOGS, DPPES, DOTMA, DOTAP, DDAB, DMRIE, DOSPA, and DOSPER.

In some embodiments of the present lipid aggregates, a particularly preferred though non-limiting cationic lipid used in the formation of the inventive transfection complexes may be dihydroxyl-dimyristylspermine tetrahydrochloride (hereinafter referred to as "DHDMS") having the structure:

In some embodiments of the present lipid aggregates, a particularly preferred though non-limiting cationic lipid used in the formation of the inventive transfection complexes may be hydroxyl-dimyristylspermine tetrahydrochloride (hereinafter referred to as "HDMS") having the structure:

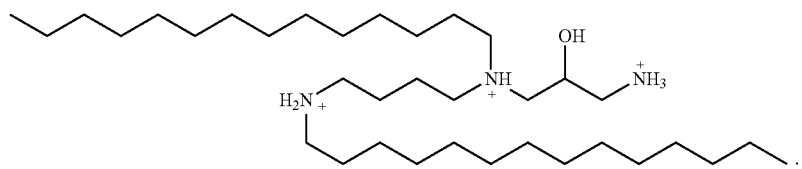 [SMILES: CCCCCCCCCCCCCCNCCCCN(CCCCCCCCCCCCCC)CC(O)CN]

In some embodiments, the neutral lipids may be selected from the following; DOPE, cholesterol or DOPC. In one embodiment, a neutral lipid may be one of cholesterol, DOPE or DOPC. In an embodiment, the a lipid is cholesterol. In an embodiment, a neutral lipid is DOPE. In an embodiment, a lipid is DOPC.

In one embodiment, the optional second neutral lipid may be one of cholesterol, DOPE or DOPC, except that the second neutral lipid and the first neutral lipid described above are not the same. In an embodiment, the optional second neutral lipid is cholesterol. In an embodiment, the optional second neutral lipid is DOPE. In an embodiment, the optional second neutral lipid is DOPC.

In some embodiments, the molar ratio of the cationic lipid in the lipid aggregate may be in the range of about 0.1 to about 0.8. In some embodiments, the molar ratio of the cationic lipid in the lipid aggregate may be between 0.1 to about 0.2, about 0.15 to about 0.25, about 0.2 to about 0.3, about 0.25 to about 0.35, about 0.3 to about 0.4, about 0.35 to about 0.45, about 0.4 to about 0.5, about 0.45 to about 0.55, about 0.5 to about 0.6, about 0.55 to about 0.65, about 0.6 to about 0.7, about 0.65 to about 0.75, about 0.7 to about 0.8, or about 0.75 to about 0.85.

In some embodiments, the molar ratio of DHDMS in the lipid aggregate may be in the range of about 0.1 to about 0.7. In some embodiments, the molar ratio of the cationic lipid in the lipid aggregate may be about 0.1, about 0.2, about 0.25, about 0.3 or about 0.4, or any range falling therebetween.

In some embodiments, the molar ratio of DHDMS is about 0.1 to about 0.4. In some embodiments, the molar ratio of DHDMS is about 0.1, about 0.2, about 0.25, about 0.3, about 0.4, or any range falling therebetween.

In some embodiments, the molar ratio of HDMS in the lipid aggregate may be in the range of about 0.1 to about 0.4. In some embodiments, the molar ratio of the second cationic lipid in the lipid aggregate may be about 0.1, about 0.2, about 0.25, about 0.3 or about 0.4, or any range falling therebetween.

In some embodiments, the molar ratio of HDMS is about 0.1 to about 0.4. In some embodiments, the molar ratio of HDMS is about 0.1, about 0.2, about 0.25, about 0.3, about 0.4, or any range falling therebetween.

In some embodiments, the molar ratio of the neutral lipid in the lipid aggregate may be in the range of about 0.1 to about 0.8. In some embodiments, the molar ratio of the cationic lipid in the lipid aggregate may be between 0.1 to about 0.2, about 0.15 to about 0.25, about 0.2 to about 0.3, about 0.25 to about 0.35, about 0.3 to about 0.4, about 0.35 to about 0.45, about 0.4 to about 0.5, about 0.45 to about 0.55, about 0.5 to about 0.6, about 0.55 to about 0.65, about 0.6 to about 0.7, about 0.65 to about 0.75, about 0.7 to about 0.8, or about 0.75 to about 0.85, or any range falling therebetween.

In some embodiments, the molar ratio of cholesterol is about 0.1 to about 0.8. In some embodiments, the molar ratio of the cationic lipid in the lipid aggregate may be between 0.1 to about 0.2, about 0.15 to about 0.25, about 0.2 to about 0.3, about 0.25 to about 0.35, about 0.3 to about 0.4, about 0.35 to about 0.45, about 0.4 to about 0.5, about 0.45 to about 0.55, about 0.5 to about 0.6, about 0.55 to about 0.65, about 0.6 to about 0.7, about 0.65 to about 0.75, about 0.7 to about 0.8, or about 0.75 to about 0.85, or any range falling therebetween.

In some embodiments, the molar ratio of DOPE is about 0.1 to about 0.8. In some embodiments, the molar ratio of the cationic lipid in the lipid aggregate may be between 0.1 to about 0.2, about 0.15 to about 0.25, about 0.2 to about 0.3, about 0.25 to about 0.35, about 0.3 to about 0.4, about 0.35 to about 0.45, about 0.4 to about 0.5, about 0.45 to about 0.55, about 0.5 to about 0.6, about 0.55 to about 0.65, about 0.6 to about 0.7, about 0.65 to about 0.75, about 0.7 to about 0.8, or about 0.75 to about 0.85, or any range falling therebetween.

In some embodiments, the molar ratio of DOPC is about 0.1 to about 0.4. In some embodiments, the molar ratio of DOPC is about 0.1, about 0.2, about 0.25, about 0.3, about 0.4, or any range falling therebetween.

In some embodiments, the molar ratio of cholesterol is about 0.2 to about 0.8. In some embodiments, the molar ratio of cholesterol is about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of DOPE is about 0.2 to about 0.8. In some embodiments, the molar ratio of DOPE is about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of DOPC is about 0.2 to about 0.8. In some embodiments, the molar ratio of DOPC is about 0.1, about 0.2, about 0.25, about 0.3, about 0.35, about 0.4, about 0.45, about 0.5, about 0.55, about 0.6, about 0.65, about 0.7, about 0.75, about 0.8, or any range falling therebetween.

In some embodiments, the molar ratio of DHDMS is about 0.1, 0.2, 0.25, 0.3, 0.4, or 0.5 and molar ratio of the neutral lipid is about 0.1, 0.2, 0.25, 0.3, 0.4, or 0.5.

In some embodiments, the molar ratio of HDMS is about 0.1, 0.2, 0.25, 0.3, 0.4, or 0.5 and molar ratio of neutral lipid is about 0.1, 0.2, 0.25, 0.3, 0.4, or 0.5.

The composition of a variety of lipid formulations in accordance with several non-limiting embodiments of the invention are provided in Table I. The provision of these exemplary embodiments is in no way meant to limit the scope of the invention solely to those formulations disclosed. On the contrary, it is merely meant to provide a variety of possible lipid aggregate formulations that can be used in the practice of the present invention. Nevertheless, it will be apparent to one skilled in the art that the formulations may be changed or altered, and additional components (such as, e.g., additional cationic or neutral lipids, peptide targeting moieties, and the like) may be added, or one of the recited neutral lipids set forth in Table I may optionally be removed, and the resulting formulations will be within the spirit and scope of the invention as described herein.

Preparation and Use of Complexes Containing Non-Naturally Occurring Peptides

Another embodiment of the present invention provides a method for delivering a polyanion such as a nucleic acid molecule into a cell or cells, wherein the method comprises forming a lipid aggregate, preferably a liposome, comprising one or more cationic lipids and one or more neutral lipids, contacting the lipid aggregate with the polyanion that has already been complexed with the non-naturally occurring peptide of the present invention by virtue of the presence of the cationic region B therein, thereby forming a neutral or positively charged polyanion-peptide-lipid aggregate complex, and incubating a cell or cells with the complex. Useful anions include proteins, peptides and nucleic acids, preferably DNA or RNA. Preferably, the lipid aggregate further comprises at least one additional helper lipid. Optionally, the polyanion-lipid aggregate complex is stored for a period prior to being contacted with the cell or cells. The polyanion-lipid aggregate complex is stable and can be stored for a time period of at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year, or for a time period between any of these time periods. This invention is particularly useful to deliver RNAi, including siRNA, short hairpin RNA (shRNA), and small temporally regulated RNA (stRNA), which optionally are chemically modified.

The methods of the present invention involve contacting any cell, preferably a eukaryotic cell, with a transfection complex comprising at least a non-naturally occurring peptide, a transfection agent and a nucleic acid as described above. The complex optionally may also contain one or more additional peptides or proteins, such as a fusogenic, membrane-permeabilizing, transport or trafficking sub-cellular-localization, or receptor-ligand peptide or protein. These additional peptides or proteins optionally may be conjugated to a nucleic acid-binding group, or optionally conjugated to the transfection agent (lipid or polycationic polymer) where the peptide or protein or modified peptide or protein is non-covalently associated with the nucleic acid. Without being bound by any theory, applicants believe that the complexes of the present invention are lipid aggregates that typically contain liposomal or lipid aggregate structures, although the precise nature of these structures is not presently known. Accordingly, in certain illustrative examples, complexes of the present invention are liposomal complexes. The entire complex, or a portion of the complex, such as a lipid portion, for example a lipid of Formula I, can be formulated into liposomes, for example using the method of reverse evaporation, which is well known in the art. Alternatively the lipid portion of the complex or the entire complex, can be formulated by other well-known methods for liposome formation such as sonication or microfluidization. These liposome formulations are effective for transfecting DNA into cultured cells.

In one embodiment, a complex containing the non-naturally occurring peptide- or protein of the invention and the nucleic acid (where the non-naturally occurring peptide or protein can optionally be conjugated to a nucleic-acid binding group) is first formed and then combined with a cationic lipid, such as a lipid of Formula I, for transfection. In a related embodiment, a peptide- or protein-lipid conjugate is combined optionally with other lipids, including any appropriate cationic lipid, and then combined with nucleic acid for transfection. In another related embodiment, a nucleic acid-lipid complex is formed and then combined with a non-naturally occurring peptide or protein for transfection. As discussed above, the lipid-containing complexes of any of these embodiments can be liposomal or non-liposomal formulations. Furthermore, any of the complexes formed in these embodiments can be stored, for example, for 5 minutes to 1 year, or for 15 minutes to 6 months, or for 1 hour to 3 months, before transfecting cells. In the case of a peptide or protein-lipid conjugate, such a conjugate can be stored for example, for 5 minutes to 1 year, or for 15 minutes to 6 months, or for 1 hour to 3 months, before combining with nucleic acid.

In another embodiment, a complex containing the non-naturally occurring peptide or protein and the nucleic acid (where the non-naturally occurring peptide or protein can be conjugated to a nucleic-acid binding group) is formed and then combined with a polycationic polymer for transfection. In a related embodiment, a peptide-polycationic polymer conjugate is combined optionally with another polycationic polymer and then combined with nucleic acid for transfection. In another related embodiment, a nucleic acid-polycationic polymer complex is formed and then combined with a peptide or protein for transfection. A polycationic polymer and/or peptide-conjugated polycationic polymer can be combined with cationic lipids and cationic lipid composition to obtain improved nucleic acid transfection compositions. In accordance with the invention, multiple peptides and/or proteins may be added to accomplish transfection.

Transfection compositions of this invention comprising peptide- or protein-lipid conjugates and nucleic acids can further include other non-peptide or non-protein agents that are known to further enhance transfection.

Transfection compositions of this invention comprising peptide- or protein-polycationic polymer conjugates and nucleic acid can further include other non-peptide agents that are known to further enhance polycationic polymer transfection, for example polycationic polymer transfection can be enhanced by addition of DEAE-dextran and/or chloroquine.

In one preferred though non-limiting embodiment, the non-naturally occurring peptide of the present invention may be first bound by non-covalent association to a nucleic acid or other cargo to be introduced into a cell. The peptide-nucleic acid complexes are then admixed with a transfection agent (or mixture of agents) and the resulting mixture is employed to transfect cells. Preferred transfection agents are cationic lipid compositions, such as but not limited to those containing a lipid of Formula (I), particularly monovalent and polyvalent cationic lipid compositions, more particularly cationic lipid compositions composed of a 1:1 to 4:1 mixtures of cationic lipid and DOPE and a 1:1 to 4:1 mixtures of cationic lipid and cholesterol, as well as a 1:1 to 4:1 mixtures of cationic lipid and DOPC, more particularly cationic lipid compositions composed of a 1:1 to 4:1 mixtures of dihydroxyl-dimyristylspermine tetrahydrochloride and DOPE and a 1:1 to 4:1 mixtures of dihydroxyl-dimyristylspermine tetrahydrochloride and cholesterol, as well as a 1:1 to 4:1 mixtures of dihydroxyl-dimyristylspermine tetrahydrochloride and DOPC as well as a 1:1 to 4:1 mixtures of hydroxyl-dimyristylspermine tetrahydrochloride and DOPE and a 1:1 to 4:1 mixture of hydroxyl-dimyristylspermine tetrahydrochloride and cholesterol, as well as a:1 to 4:1 mixtures of hydroxyl-dimyristylspermine tetrahydrochloride and DOPC.

In another optional embodiment, a mixture of one or more transfection-enhancing peptides, proteins, or protein fragments, including fusogenic peptides or proteins, transport or trafficking peptides or proteins, receptor-ligand peptides or proteins, or nuclear localization peptides or proteins and/or their modified analogs (e.g., spermine modified peptides or proteins) may be complexed with nucleic acid at the same time or immediately after complexation of the nucleic acid with the non-naturally occurring peptide of the present invention to be introduced into a cell. The peptide-nucleic acid complexes are then admixed with transfection agent and the resulting mixture is employed to transfect cells. In certain embodiments, the mixture of the transfection enhancing peptide, protein, or protein fragment is stored before it is complexed with nucleic acid.

In another optional embodiment, a component of a transfection agent (lipids, neutral lipids, helper lipids, cationic lipids, dendrimers, or PEI) may be covalently conjugated to selected peptides, proteins, or protein fragments directly or via a linking or spacer group. Of particular interest in this embodiment are peptides or proteins that are non-naturally occurring fusogenic proteins from non-enveloped viruses such as are known in the art.

Exemplary Uses of the Complexes Containing Non-Naturally Occurring Peptides of Non-Enveloped Viruses The delivery methods employing the lipid aggregates of the present invention or mixtures thereof can be applied to cells in vitro, ex vivo, and in vivo, particularly for transfection of eukaryotic cells or tissues including animal cells, human cells, non-human animal cells, insect cells, plant cells, avian cells, fish cells, mammalian cells and the like. The polyanion that is to be delivered into the cell is contacted with lipid aggregates in the presence of a non-naturally occurring peptide as described above to form a polyanion-lipid-polypeptide aggregate complex. The target cell or cells are then incubated with the complex, or, for in vivo applications, the complex is administered to the organism so that the complex contacts the target cells or tissue. The compounds of the present invention may also be conjugated to or mixed with or used in conjunction with a variety of useful molecules and substances, also referred to as transfection helpers, such as proteins, peptides, growth factors and the like to enhance cell-targeting, uptake, internalization, nuclear targeting and expression.

The complexes and methods of the present invention, especially those involving transfection compositions that include complexes provided herein, can be used for in vitro and in vivo transfection of cells, particularly of eukaryotic cells, and more particularly to transfection of higher eukaryotic cells, including animal cells. The methods of this invention can be used to generate transfected cells which express useful gene products. The methods of this invention can also be employed as a step in the production of transgenic animals. The methods of this invention can be useful as a step in any therapeutic method requiring introduction of nucleic acids into cells including methods of gene therapy and viral inhibition and for introduction of antisense or antigene nucleic acids, ribozymes, RNA regulatory sequences, siRNA, RNAi, Stealth® RNAi (Invitrogen Corporation, Carlsbad Calif.) or related inhibitory or regulatory nucleic acids into cells. In particular, these methods may be useful in cancer treatment, in in vivo and ex vivo gene therapy, and in diagnostic methods.

The transfection compositions and methods of this invention comprising peptides, proteins, peptide or protein fragments or modified peptides or modified proteins, can also be employed as research agents in any transfection of eukaryotic cells done for research purposes.

Accordingly, provided herein is a method of introducing a macromolecule into a cell, that includes forming a transfection composition that includes a nucleic acid and a complex comprising a transfection agent and a fusion agent, wherein the fusion agent includes a fusion promoting amino acid sequence derived from a fusion protein of a non-enveloped virus; and contacting a eukaryotic cell with the transfection composition. Provided in the Examples section herein are illustrative protocols for using compositions of the present invention to transfect eukaryotic cells. As disclosed herein, the fusion agent in illustrative examples is a membrane fusion peptide (MPP), advantageously a fusion peptide that is between 5 and 50 amino acids in length where at least 5 contiguous amino acids of the fusion peptide are at least 50, 55, 60, 65, 70, 75, 80, 85, 90, 95 or 100% similar to any of the peptides set forth in Table 1.

A further embodiment provides a method of transfecting a cell or tissue with a nucleic acid in vivo wherein the method comprises forming a lipid aggregate, preferably a liposome, comprising one or more cationic lipids, optionally one or more neutral lipids and optionally one or more helper lipids, contacting the lipid aggregate with the nucleic acid-peptide complex formed by contacting the nucleic acid to a non-naturally occurring peptide of the present invention under conditions sufficient to promote the stable non-covalent interaction between the peptide and the nucleic acid, thereby forming a neutral or positively charged lipid aggregate-nucleic acid complex, and administering the lipid aggregate-nucleic acid complex to the organism so that the complex contacts the target cells or tissue.

Administration of the lipid aggregate-peptide-nucleic acid complex can be achieved orally, intravenously, or by subcutaneous or intramuscular injection or applied topically to the tissue or to cells in culture in a laboratory setting.

Optionally, the polyanion-peptide-lipid aggregate complex is stored for a period prior to being contacted with the cell or cells for transfection. The polyanion-peptide-lipid aggregate complex is stable and can be stored for a time period of at least 30 minutes, at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year, or for a time period between any of these time periods.

In another embodiment, lipid aggregates of the present invention (approximately between 1 µl and 2000 µl) are provided in the wells of a multiwell plate. Target polyanion molecules to be delivered into target cells are selected and added to the wells to form polyanion-peptide-lipid aggregate complexes, which are subsequently contacted with the target cells. The lipid aggregates can have the same composition and concentration in each well, or the lipid aggregate composition and/or concentration can vary from well to well. Where the polyanions are nucleic acids such as DNA or RNA, the nucleic acids can be added to the wells and optionally stored before contacting with the target cells.

The methods of this invention optionally comprise the step of contacting the one or more cationic lipids with one or more helper or neutral lipids before or at the same time as contacting the nucleic acid-peptide complex with the one or more cationic lipids to form lipid aggregates encapsulating the nucleic acid-peptide. The methods also optionally comprise forming the lipid aggregates into liposomes prior to contact with the nucleic acid. In further embodiments, the liposomes are formed by microfluidization, extrusion or other means known in the art. The nucleic acids are preferably DNA or RNA that inhibit expression of a target gene. Preferably the nucleic acid associates with a transcript of the gene to effect inhibition. Preferably, the nucleic acid is RNAi, siRNA, shRNA, or stRNA, and is optionally chemically modified.

Volumes and concentrations of nucleic acid or other macromolecule, volume and concentration of the transfection complexes provided herein, volumes and compositions of diluents, and volume and concentration of cells, can be determined using standard experimental approaches for such optimization and titration, including, for example, methods that utilize cytotoxicity assays and/or methods that employ transfection using nucleic acid expression vectors that express reporter genes, such as beta galactosidase, luciferase, and/or fluorescent proteins. Furthermore, cell densities can be optimized using standard methods, and cell densities for transfections using the transfection complexes provided herein can range, for example, from high density>75% to low density<50%

Exemplary diluents for complexation reactions, for example, include reduced-serum, or serum-free media, such as D-MEM and RPMI 1640 and OptiPro™, Opti-MEM® (Invitrogen Corporation). Incubation times for forming complexes can be determined using routine methods, although typical incubation times are between 5 and 240 minutes. In addition, it will be understood that media for culturing of cells before and after transfection can be chosen based on the cell line to be transfected and based on the particular application of the method. For example, for the production of proteins in suspension cells, in illustrative embodiments, reduced serum, or advantageously serum-free, medium can be used. In certain illustrative embodiments, animal origin-free medium is employed, such as, but not limited to, 293 Expression Medium (Invitrogen Corporation) and CD-CHO Medium (Invitrogen Corporation). In certain aspects depending on the cell type to be transfected, antibiotics can be excluded from post-transfection media. Incubation times for post-transfection culturing of cells varies depending on the cell type and the desired outcome of the transfection, but typically ranges from 2 hours to 7 days. For large-scale protein production, cells can be incubated, as a non-limiting example, for between 1 day and 7 days.

It will be understood that a wide range of concentrations of transfection agent and a fusion agent can be used in the complexes, compositions and methods provided herein. For example, in an illustrative non-limiting example of a composition that includes a complex of a cationic lipid and a non-naturally occurring peptide, the total exemplary, non-limiting combined concentration of cationic lipid and non-naturally occurring peptide in the composition can be between 1 mg/ml and 4 mg/ml. The range of peptide added to the lipid at 1 mg/ml can between 100 µg/ml and 3 mg/ml. The ratio of the cationic lipid to helper lipid can between 0.5/1.0 (molar) and pure compound.

Cells that can be transfected according to the present invention include, for example, virtually any eukaryotic cell including primary cells, cells in culture, and cells in cultured tissue, particularly cell that are considered difficult to transfect. The cells can be attached cells or cells in suspensions. In certain illustrative aspects, the cells are suspension CHO—S cells and suspension 293-F cells. Suspension cell cultures are particularly well-suited for protein production methods provided herein. Other cells that can be transfected using the agents and methods of the invention include, but are not limited to, 293, such as GripTite 293 MSR (Invitrogen Corporation), CHO, Cos7, NIH3T3, Hela, primary fibroblast, A549, Be2C, SW480, Caco2, primary neurons, Jurkat, C6, THP1, IMR90, HeLa, ChoKl, GT293, MCF7, HT1080, LnCap, HepG2, PC12, SKBR3, and K562 cells, or any cells listed in Table 6.

In certain embodiments provided herein, a transfection enhancing agent is included in the complex that is used to transfect cells. For example the transfection enhancing agent can be a nuclear localization peptide. In one example, the transfection enhancing agent is the PLUS™ Reagent (Invitrogen Corporation). It has been shown that the addition of PLUS™ reagent enhances protein expression when used together with transfection compositions as provided herein. Cytotoxicity was not affected by the use of the PLUS™ Reagent.

In another embodiment, provided herein is a method for producing a protein comprising, transfecting a cell with a nucleic acid molecule encoding the protein, incubating the cell to produce the protein, and collecting the protein, wherein the transfecting is performed by contacting the cell with a transfection composition including a non-naturally occurring peptide of the present invention. The composition for transfecting the cell can be any compositions as provided herein. Exemplary compositions include the nucleic acid molecule encoding the protein of interest, complexed with a non-naturally occurring peptide of the present invention, optionally a fusion agent, and a transfection agent.

In illustrative embodiments the encoded protein is an antibody molecule, or an antigen binding fragment or derivative portion thereof, for example a single chain Fv fragment. In these embodiments, the method can further include isolating the protein, for example, by using affinity purification on an antibody-binding column. In certain examples, nucleic acids encoding both chains of an antibody are transfected into cells using a transfection composition provided herein.

It will be understood that the nucleic acid encoding the protein can be an expression vector. The expression vector typically has a promoter operatively linked to one or more nucleic acid sequences encoding one or more protein chains. Where the protein produced is a pharmaceutical product, the protein can be formulated accordingly, for example in an appropriate choice of physiologic medium.

The transfection composition provided herein can also be used to introduce peptides and proteins and the like into cells using methods that are known in the art. Methods of using cationic lipids for peptide and protein delivery previously have been described. In addition, the transfection compositions can be used to deliver nucleic acids, peptides and proteins and the like into tissues in vivo. Methods of using lipids for delivering compounds to tissue in vivo previously have been described. The transfection compositions can, with appropriate choice of physiologic medium, be employed in therapeutic and diagnostic applications.

Reagent Kits:

The invention is further directed to kits containing, in at least a first suitable container, at least one non-naturally occurring peptide in accordance with the present invention. The kits of the present invention can further comprise one or more containers comprising a reagent that facilitates the introduction of at least one macromolecule, e.g., a cationic transfection reagent, optionally one or more helper lipids or neutral lipids, and may optionally be provided with a cargo, such as, e.g., a nucleic acid or other cargo as defined above. Preferred transfection reagents include, but are not limited to, cationic lipids and the like.

Components of the transfection compositions of this invention can be provided in a reagent kit. The kit may contain a transfection agent and a non-naturally occurring peptide of the present invention. This kit can also optionally include a transfection enhancing agent such as a transfection-enhancing peptide, protein or fragment thereof or a transfection enhancing compound. The transfection agent, the non-naturally occurring peptide, and the optional transfection enhancing agent, when present, can each be included as a mixture (i.e. in a single container, typically a tube and/or vial), or can be included as separate portions (i.e. in separate containers, for example separate vials and/or tubes). The kits of the present invention, as will be understood, typically include vessels, such as vials and/or tubes, which are packaged together, for example in a cardboard box or other packaging. The kits can be shipped from a supplier to a customer. For example, in one example provided herein is a kit that includes a vial that includes a liposomal formulation that includes a transfection agent and a transfection enhancing peptide. The kit can also include, for example, a separate vessel that includes a transfection enhancing agent, such as a transfection enhancing peptide, for example Plus Reagent™ (Invitrogen Corp., Carlsbad, Calif.). The kit can also include in separate containers, cells, cell culture medium, and a reporter nucleic acid sequence, such as a plasmid that expresses a reporter gene. In certain examples, the culture medium can be reduced-serum medium and/or protein expression medium.

In one embodiment, a kit comprises individual portions of, or a mixture of, cationic lipid, such as but not limited to a lipid of Formula I, optionally in combination with one or more helper lipids and/or one or more neutrallipids, and peptide, protein or fragment thereof or modified peptide, protein or fragment thereof of the present invention. In another embodiment, a kit comprises individual portions of, or a mixture of, polycationic polymers and peptide, protein or fragments thereof or modified peptide, protein or fragments thereof of the present invention. Cationic lipid transfection kits can optionally include neutral lipid as well as other transfection-enhancing agents or other additives, and the relative amounts of components in the kit may be adjusted to facilitate preparation of transfection compositions. Kit components can include appropriate medium or solvents for other kit components.

Cationic lipid transfection kits comprising a monocationic or polycationic lipid composition, such as but not limited to a lipid of Formula I, and further including a neutral lipid and a peptide or protein of the present invention are preferred.

Dendrimer transfection kits can optionally include other transfection enhancing agents, such as DEAE-dextran and/or chloroquine, as well as other additives and the relative amounts of components in the kit may be adjusted to facilitate preparation of transfection compositions.

Kits provided by this invention include those comprising an individual portion of a polycationic lipid composition comprising DOSPA and DOPE or a monocationic lipid composition comprising DOTMA and DOPE and a portion of modified peptide, optionally a spermine- or spermidine-modified peptide. Kits provided by this invention include those comprising an individual portion of a polycationic polymer and a portion of a spermine-modified peptide.

In related embodiments, kits of this invention can comprise a peptide- or protein-lipid conjugate or a peptide- or protein-polycationic polymer conjugate in combination with non-conjugated lipids, non-conjugated polycationic polymer and other agents to facilitate transfection.

Kits of this invention can include those useful in diagnostic methods, e.g., diagnostic kits which in addition to transfection agent and transfection-enhancing agents (e.g., proteins, peptides, and fragments and modifications of peptides and proteins) can contain a diagnostic nucleic acid. A diagnostic nucleic acid is a general term for any nucleic acid which can be employed to detect the presence of another substance (most generally an analyte) in a cell. For example, when transfected into a cell a diagnostic nucleic acid may increase or decrease expression of a gene therein in response to the presence of another substance in the cell (e.g., a protein, small molecule, steroid, hormone, or another nucleic acid). Diagnostic nucleic acids also include those nucleic acids that carry some label or otherwise detectable marker to a particular target cell or target tissue for detection of the target cell or tissue or for detection of a substance in the target cell or tissue.

Nucleic acids that can be transfected by the methods of this invention include DNA and RNA of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays (e.g., diagnostic nucleic acids). Therapeutic nucleic acids include those nucleic acids that encode or can express therapeutically useful proteins, peptides or polypeptides in cells, those which inhibit undesired expression of nucleic acids in cells, and those which inhibit undesired enzymatic activity or activate desired enzymes in cells.

The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

The lipids of Formula I can be used as the cationic lipid(s) of the kits described above, and may independently be provided in a reagent kit. In general, the kit contains a lipid of Formula (I) in a suitable container. The lipid may be, for example, in a solution of an organic solvent, such as ethanol, in a buffer, or in a solvent/buffer mixture In addition, the kit may include, but is not limited to, a lipid of Formula (I), and an amino acid sequence from a non-naturally occurring protein that enhances or promotes membrane fusion of a liposome carrier with a cell membrane in a suitable solvent or buffer.

In one embodiment, a kit may comprise individual portions of, or a mixture of, e.g., lipids of Formula (I) or other cationic lipids and peptide, protein or fragment thereof or modified peptide, protein or fragment thereof. Kits which include lipids of Formula (I) or other cationic lipids can optionally include neutral lipid as well as other transfection-enhancing agents or other additives, and the relative amounts of components in the kit may be adjusted to facilitate preparation of transfection compositions. Kit components can include appropriate medium or solvents for other kit components.

Kits which include lipids of Formula (I) or other cationic lipids, a neutral lipid and a modified peptide or protein are preferred. Kits provided by this invention include those composition comprising an individual portion of a lipid of Formula (I), DOPE and a portion of peptide, particularly a spermine-modified peptide. Kits provided by this invention include those comprising an individual portion of a lipid of Formula (I), and a portion of a modified peptide containing a stretch of basic amino acids such lysine, ornithine, or arginine.

Methods for Selling

Also provided is a method for selling a non-naturally occurring peptide, lipid, transfection complex, transfection composition, and/or kit provided herein, comprising presenting to a customer an identifier that identifies the non-naturally occurring peptide, lipid, complex and/or transfection composition, and/or a kit provided herein, and providing access to the customer to a purchase function for purchasing the non-naturally occurring peptide, lipid, transfection complex, transfection composition, and/or kit provided herein using the identifier. The identifier is typically presented to the customer as part of an ordering system. The ordering system can include an input function for identifying a desired product, and a purchasing function for purchasing a desired product that is identified. The ordering system is typically under the direct or indirect control of a provider. A customer as used herein, refers to any individual, institution, corporation, university, or organization seeking to obtain biological research products and services. A provider as used herein, refers to any individual, institution, corporation, university, or organization seeking to provide biological research products and services.

The present invention also provides a method for selling a non-naturally occurring peptide, lipid, transfection complex, transfection composition, and/or kit provided herein, comprising: presenting to a customer an input function of a telephonic ordering system, and/or presenting to a customer a data entry field or selectable list of entries as part of a computer system, wherein the non-naturally occurring peptide, lipid, transfection complex, transfection composition and/or kit is identified using the input function. Where the input function is part of a computer system, such as displayed on one or more pages of an Internet site, the customer is typically presented with an on-line purchasing function, such as an online shopping cart, wherein the purchasing function is used by the customer to purchase the identified non-naturally occurring peptide, lipid, transfection complex, transfection composition, and/or kit. In one aspect, a plurality of identifiers are provided to a customer, each identifying a different non-naturally occurring peptide, lipid, complex and/or transfection composition, and/or a kit provided herein, or a different volume or weight of the non-naturally occurring peptide, lipid, complex and/or transfection composition, and/or a kit provided herein. The method may further comprise activating the purchasing function to purchase the lipid, transfection complex, transfection composition, and/or kit provided hererin. The method may still further comprise shipping the purchased non-naturally occurring peptide, lipid, transfection complex, transfection composition, and/or kit provided herein to the customer. The non-naturally occurring peptide, lipid, transfection complex, transfection composition, and/or kit can be shipped by a provider to the customer. The provider typically controls the input function, and can control the web site accessed to access the input function to purchase a non-naturally occurring peptide, lipid, complex and/or transfection composition, and/or a kit provided herein.

Pharmaceutical Compositions

Transfection agents and transfection-enhancing agents of this invention can be provided in a variety of pharmaceutical compositions and dosage forms for therapeutic applications. For example, injectable formulations, intranasal formulations and formulations for intravenous and/or intralesional administration containing these complexes can be used therapy.

In general the pharmaceutical compositions of this invention should contain sufficient transfection agent and any enhancing agents (peptide, protein, etc.) to provide for introduction of a sufficiently high enough level of nucleic acid into the target cell or target tissue such that the nucleic acid has the desired therapeutic effect therein. The level of nucleic acid in the target cell or tissue that will be therapeutically effective will depend on the efficiency of inhibition or other biological function and on the number of sites the nucleic acid must affect.

The dosage of transfection compositions described herein administered to a patient will depend on a number of other factors including the method and site of administration, patient age, weight and condition. Those of ordinary skill in the art can readily adjust dosages for a given type of administration, a given patient and for a given therapeutic application.

It will be appreciated by those of ordinary skill in the art that the transfection composition should contain minimal amounts of inhibitory components, such as serum or high salt levels, which may inhibit introduction of nucleic acid into the cell, or otherwise interfere with transfection or nucleic acid complexation. It will also be appreciated that any pharmaceutical or therapeutic compositions, dependent upon the particular application, should contain minimal amounts of components that might cause detrimental side-effects in a patient.

The transfection compositions described herein may be formulated into compositions which include a pharmaceutically active agent and a pharmaceutically acceptable diluents, excipients or carriers therefor. Such compositions may be in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in Remington's Pharmaceutical Sciences, (Gennaro, ed., Mack Publishing Co., Easton Pa., 1990, herein incorporated by reference).

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. When the carrier serves as a diluent, it may be a solid, semi-solid or liquid material which acts as a vehicle, excipient or medium for the active ingredient. In the case of injections, it is possible to prepare solutions or liposomes of one or more lipids of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, and the like.

EXAMPLES

The following Examples are provided to illustrate certain aspects of the disclosure and to aid those of skill in the art in practicing the disclosure. These Examples are in no way to be considered to limit the scope of the disclosure in any manner.

Example 1. Preparation of Lipid Aggregate/Polypeptide Complexes and Transfection of Cultured Cells All cells were cultured under standard culture conditions recommended for each cell line by the American Type Culture Collection (ATCC). Approximately 24 hrs prior to transfections, cells were seeded so that they would be 70-90% confluent on the day of transfection. The following guidelines are generally applicable, though minor variations exist as will be readily appreciated by one skilled in the art, and depending on the identity of the cell line, its growth characteristics and needs, and its morphology in adherent culture. Generally, for a 96-well plate, between 1-4×10$^4$ cells per well were seeded, for a 24-well plate 0.5-2×10$^5$ cells per well were seeded, for a 6-well plate 0.25-1×10$^6$ cells were seeded.

Transfection complexes for transfecting DNA into cells in culture were prepared according to manufacturer protocol. LIPOFECTAMINE® 2000 and LIPIFECTAMINE® LTX were purchased from Life Technologies Corp. (Carlsbad, CA), FUGENE® HD was purchased from Promega Corp. (Fitchburg, WI), and X-TREMEGENE™ HP was purchased from Roche Diagnostics (Basel, Switzerland).

To prepare transfection complexes containing the non-naturally occurring peptides described above, Peptide 1 having the following sequence SRRARR-SPRESGKKRKRKRGGGSGGGSGGGSRRRRRRRRRRR (SEQ ID NO. 89) was synthesized and provided as a dry powder. The dry powder was reconstituted in sterile ultra-pure water to a final concentration of 4.35 mg/ml and allowed to fully dissolve. This stock peptide solution was set aside for use in the next step.

To prepare the lipid aggregate-DNA-peptide complexes, LIPOFECTAMINE® 3000 reagent (Life Technologies Corp., Carlsbad, CA) was obtained. For each well of a 96-, 24- or 6-well plate of cells to be transfected a 5 µl, 25 µl, and 125 µl, aliquot of Gibco® Opti-MEM® medium was placed in separate disposable plastic Eppendorf tube. Between 0.1 µl to 0.6 µl for a 96-well plate, 0.5 µl to 3.0 µl for a 24-well plate, or 2.0 µl to 15 µl for a 6-well plate of LIPO-FECTAMINE® 3000 reagent was added to the aliquoted Opti-MEM®, mixed well and incubated at room temperature.

In a separate Eppendorf tube, 5 µl (for each well of a 96-well plate), 25 µl (for each well of a 24-well plate), or 125 µl (for each well of a 6-well plate) of Gibco® Opti-MEM® medium was aliquoted into a tube for each well of cultured cells to be transfected, into which was mixed 0.1 µg of pcDNAEF1a/emGFP or GST-STAT expression vector DNA for each well of a 96-well plate, 0.5 µg of pcDNAEF1a/emGFP or GST-STAT expression vector DNA for each well of a 24-well plate, and 2.5 µg of pcDNAEF1a/emGFP or GST-STAT expression vector DNA for each well of a 6-well plate.

Into the diluted DNA mixture was added 0.2 µl of the stock peptide for each well of a 96-well plate, 1 µl of stock peptide for each well of a 24-well plate, and 5 µl of the stock peptide solution for each well of a 6-well plate, and the peptide/DNA mixture was mixed well and incubated for approximately 1 minute at room temperature.

For each well of a 96-well plate, 5 µl of the diluted DNA/peptide mixture was mixed with 5 µl of the diluted LIPOFECTAMINE® 3000 reagent, for each well of a 24-well plate, 25 µl of the diluted DNA/peptide mixture was mixed with 25 µl of the diluted LIPOFECTAMINE® 3000 reagent, and for each well of a 6-well plate, 125 µl of the diluted DNA/peptide mixture was mixed with 125 µl of the diluted LIPOFECTAMINE® 3000 reagent, and lipid-peptide-DNA complexes were allowed to form by incubating the resulting mixture for approximately 5 minutes at room temperature.

Following the incubation, the lipid-peptide-DNA complexes were added to cells that were seeded the previous day with fresh growth medium; for 96-well plates, 10 µl of the lipid-peptide-DNA was added to the cells, for 24-well plates, 50 µl of the lipid-peptide-DNA mixture was added to the cells, for 6-well plates, 250 µl of the lipid-peptide-DNA was added to the cells. The cells were incubated in the presence of the lipid-peptide-DNA for approximately 24-48 hrs, and analyzed.

Example 2. Transfection of Various Cell Lines

A panel of 10 difficult-to-transfect cancer cell lines (HepG2, Hepa1-6, Hep3B, HUH7, MCF-7, MDA-MB-23, SKBR3, LNCaP, Bend3, and T986), two difficult to transfect neuronal cell lines (PC12 and Neuro2A), two difficult to transfect myoblast cell lines (H9C2 and C2C12) and a difficult to transfect kidney fibroblast cell line (Vero) were transfected with pcDNAEF1a/emGFP, an expression vector encoding GFP, according to the methods set forth in Example 1. After 24 hrs in the presence of the transfection complexes, the cells were visualized using fluorescence microscopy at the appropriate wavelength.

Expression of GFP in the cancer cell lines is shown in FIG. 1A, in neuronal cells is shown in FIG. 1B, in Myoblast cells is shown in FIG. 1C, and in kidney fibroblast cells is shown in FIG. 1D.

Example 3. Comparison of Various Transfection Reagents

Figure 2:
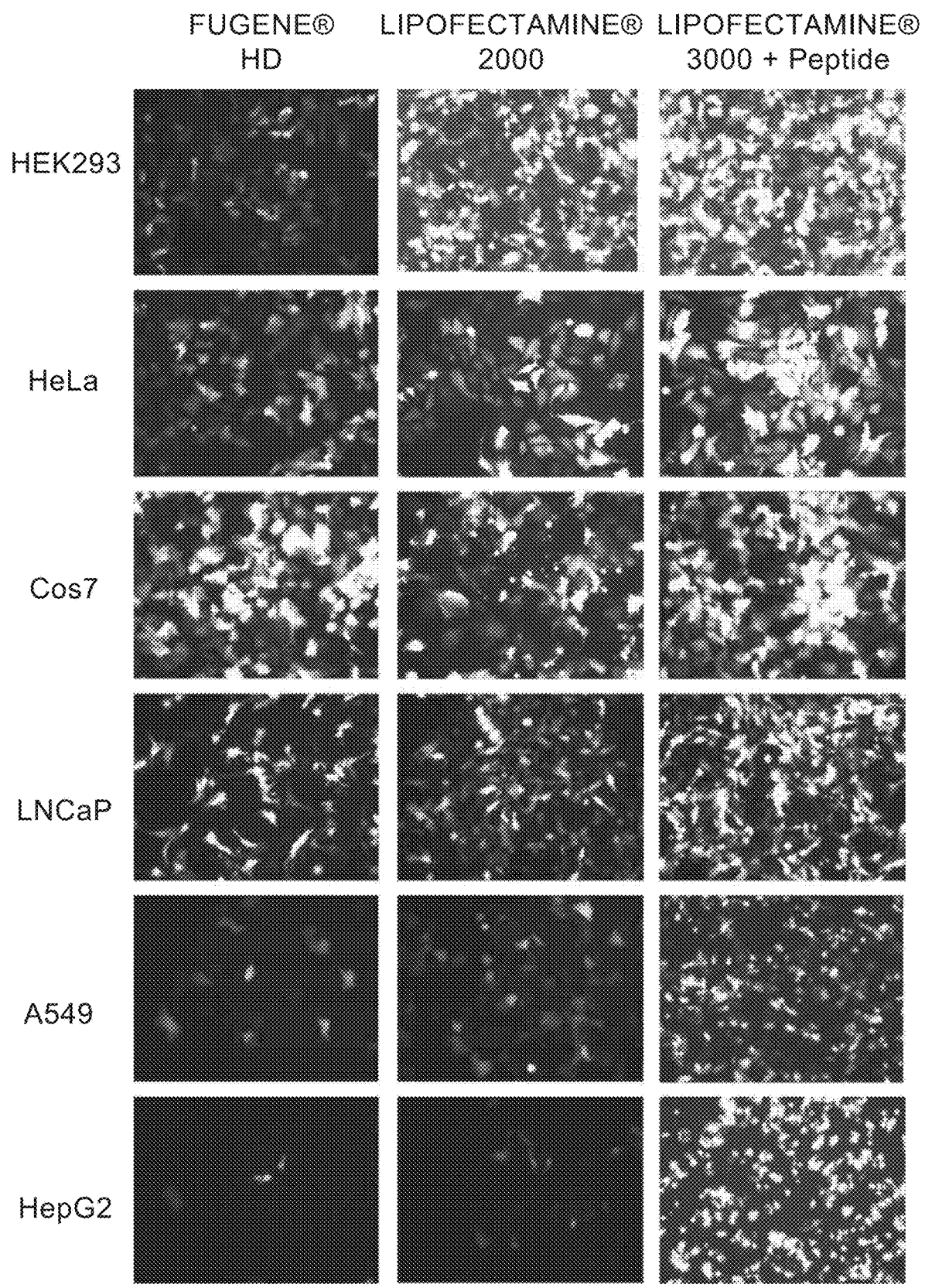
FIG. 2 shows a panel of six different cell lines expressing GFP that were transfected with an expression vector encoding GFP using a the indicated commercially available transfection reagent; FUGENE® HD (first column), LIPOFECTAMINE® 2000 (center column); and LIPOFECTAMINE® 3000 in combination with a peptide according to one embodiment (last column)

A panel of six different cell lines (HEK293, HeLa, COS-7, LNCaP, A549 and HepG2) were transfected with pcDNAEF1a/emGFP using FUGENE® HD, LIPO-FECTAMINE® 2000, or LIPOFECTAMINE® 3000 in combination with Peptide 1 as described in Example 1. The cells were allowed to transfect for 48 hrs. The results shown in FIG. 2 show that, while both FUGENE® HD and LIPO-FECTAMINR® 2000 were able to transfect a small portion of each of the cells (FIG. 2, first two columns), the presence of Peptide 1 in the transfection complex improved transfection efficiency substantially (FIG. 2, last column).

To extend this study, a panel of 61 different cell lines were transfected as above using either LIPOFECTAMINE® 2000 or LIPOFECTAMINE® 3000 in combination with Peptide 1 as described in Example 1. Approximately 48 hours after transfection, transfected cells were examined by fluorescence microscopy to determine relative transfection efficiency, and cellular extracts were prepared and analyzed using a FL600 Fluorescence Microplate Reader to measure fold improvement in GFP expression of LIPO-FECTAMINE® 3000 with Peptide 1 over LIPO-FECTAMINE® 2000. The results are shown in Table 6. As can be seen, use LIPOFECTAMINE® 3000 reagent in combination with Peptide 1 yields higher transfection efficiencies and protein expression than LIPOFECTAMINE® 2000 reagent when tested in a variety of cell lines.

TABLE 6

Performance of LIPOFECTAMINE ® 3000 and Peptide 1 lipid aggregate formulations in vitro in various cell lines as measured by relative transfection efficiency and fold improvement of transfection efficiency compared to LIPOFECTAMINE ® 2000 transfection.

| Cell line | Cell/Tissue lineage | Relative transfection efficiency (%) | Fold improvement of protein expression over LIPOFECTAMINE ® 2000 |
|---|---|---|---|
| 3T3 | Mouse embryonic fibroblast, immortalized | 51-79% | 11 |
| 4T1 | Mouse breast tumor, epithelial | 51-79% | 2 |
| A431 | Human epidermoid carcinoma, epithelial | <30% | 4 |
| A549 | Human lung carcinoma, epithelial | 51-79% | 3 |
| ACHN | Human metastatic kidney cell, adenocarcinoma | 30-50% | 2 |
| bEnd.3 | Mouse brain endothelioma, viral transformed | <30% | 9 |
| BJ | Human foreskin, immortalized epithelial | <30% | 3 |
| BT-549 | Human breast carcinoma, epithelial | 51-79% | 4 |
| C2C12 | Mouse myoblast, immortalized | 51-79% | 14 |
| C6 | Rat glioma | 30-50% | 5 |
| Caco-2 | Human colorectal carcinoma, epithelial | 51-79% | 2 |
| Caki-1 | Human kidney carcinoma, epithelial | <30% | 4 |
| CHO-K1 | Chinese hamster ovary, immortalized epithelial | 51-79% | 1 |
| CHO-S | Chinese hamster ovary, suspension adapted | <30% | 1 |
| COLO 205 | Human colorectal carcinoma, epithelial | <30% | 4 |
| COS-7 | African green monkey kidney fibroblast, virus transformed | 51-79% | 4 |
| DU 145 | Human metastatic prostate tumor, epithelial | 30-50% | 2 |
| H460 | Human lung carcinoma, large cell, epithelial | 51-79% | 3 |
| H9c2 | Rat embryonic myoblast (heart) | 51-79% | 3 |
| HCC1937 | Human mammary tumor, epithelial | <30% | 5 |
| HCT116 | human colon carcinoma, epithelial | >80% | 1 |
| HEK 293 | Human embryonic kidney fibroblasts, immortalized | >80% | 2 |
| HeLa | Human cervical carcinoma, epithelial | >80% | 3 |
| Hep-3B | Human hepatocellular carcinoma, epithelial | 51-79% | 2 |
| Hepa 1-6 | Mouse hepatocellular carcinoma, epithelial | 51-79% | 6 |
| HepG2 | Human hepatocellular carcinoma, epithelial | >80% | 16 |
| Hs 578T | Human breast carcinoma, epithelial | >80% | 3 |
| cHT29 | human colon carcinoma, epithelial | <30% | 1 |
| Huh-7 | Human hepatocellular carcinoma, epithelial | 51-79% | 4 |
| Jurkat | Human T cell, immortalized | <30% | 1 |
| K-562 | Human myelogenous leukemia | 30-50% | 2 |
| L6 | Rat myoblast | 30-50% | 8 |
| L929 | Mouse fibrosarcoma | Up to 30% | 2 |
| LNCaP | Human prostate adenocarcinoma | >80% | 10 |
| MCF 10A | Human breast carcinoma, epithelial | 30-50% | 5 |
| MCF7 | Human breast carcinoma, epithelial | 30-50% | 2 |
| MDA-MB-231 | Human breast carcinoma, epithelial | 51-79% | 3 |
| MDA-MB-435 | Human breast carcinoma, epithelial | 51-79% | 3 |

TABLE 6-continued

Performance of LIPOFECTAMINE ® 3000 and Peptide 1 lipid aggregate formulations in vitro in various cell lines as measured by relative transfection efficiency and fold improvement of transfection efficiency compared to LIPOFECTAMINE ® 2000 transfection.

| Cell line | Cell/Tissue lineage | Relative transfection efficiency (%) | Fold improvement of protein expression over LIPOFECTAMINE ® 2000 |
|---|---|---|---|
| MDA-MB-468 | Human breast carcinoma, epithelial | <30% | 9 |
| MDCK | Canine kidney, immortalized | <30% | 1 |
| Neuro-2a | Mouse neuroblastoma | >80% | 1 |
| NCI-H23 | Human lung adenocarcinoma | 51-79% | 2 |
| NCI-H460 | Human lung carcinoma, large cell | <30% | 17 |
| P19 | Mouse embryonal carcinoma/teratocarcinoma | 30-50% | 1 |
| PANC-1 | Human pancreatic carcinoma, epithelial | 51-79% | 3 |
| PC12 | Rat pheochromocytoma | 51-79% | 2 |
| RAW264.7 | Mouse macrophage, virus transformed | <30% | 4 |
| RBL-2H3 | Rat basophil leukemia | <30% | 2 |
| RD | Human rhabdomyosarcoma | 51-79% | 4 |
| Saos-2 | Human osteosarcoma | 51-79% | 4 |
| SH-SY5Y | Human neuroblastoma | <30% | 1 |
| SK-BR-3 | Human breast carcinoma, epithelial | 51-79% | 4 |
| SK-MEL-28 | Human melanoma | 51-79% | 2 |
| SK-N-SH | Neuroblastoma cell line | 30-50% | 6 |
| SK-OV-3 | Human ovarian carcinoma | 30-50% | 3 |
| SW480 | Human colorectal adenocarcinoma | 51-79% | 2 |
| SW620 | Human colorectal adenocarcinoma | <30% | 5 |
| T98G | Human glioblastoma | 51-79% | 4 |
| U2OS | Human osteosarcoma | >80% | 3 |
| U937 | Human histiocytic leukemia | <30% | 2 |
| Vero | African green monkey kidney, epithelial | 30-50% | 8 |

Example 4. Effect of Transfection Reagent Dosage on Transfection Efficiency and Protein Expression HeLa cells were plated in 96-well plates and transfected with pcDNAEF1a/emGFP using 0.1 µl, 0.2 µl, 0.3 µl or 0.4 µl of LIPOFECTAMINE® 2000, LIPOFECTAMINE® LTX, or LIPOFECTAMINE® 3000 reagent in combination with Peptide 1 as described in Example 1. Transfection efficiency and relative protein expression as measured by relative luminescence was determine for each condition. The results are shown in FIG. 3.

Figure 3A:
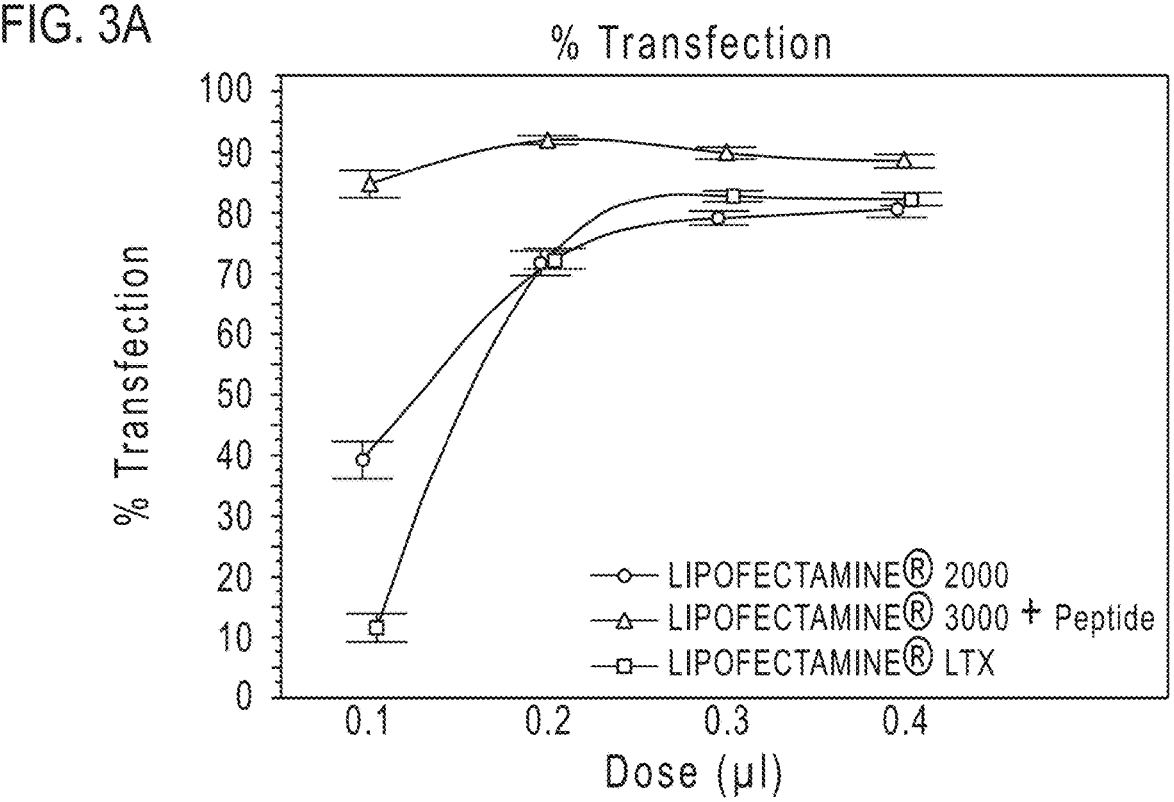
FIG. 3A is a graph comparing the relative transfection efficiency for an expression vector encoding GFP transfected into cultured HeLa cells using increasing dosages of three different commercially available lipid aggregate formulations, LIPOFECTAMINE® 2000 (open circles), LIPOFECTAMINE® LTX (open squares), and LIPOFECTAMINE® 3000 in combination with a peptide according to an embodiment (open triangles)

FIG. 3A is a graph comparing the relative transfection efficiency for an expression vector encoding GFP transfected into cultured HeLa cells using increasing dosages of three different commercially available lipid aggregate formulations, LIPOFECTAMINE® 2000 (open circles), LIPOFECTAMINE® LTX (open squares), and LIPOFECTAMINE® 3000 in combination with a peptide according to an embodiment (open triangles). The presence of Peptide 1 in the transfection complex improves transfection efficiency of the cells over the entire range of transfection reagent dosages tested. The improvement to transfection efficiency is particular pronounce at the lowest tested dosage.

Figure 3B:
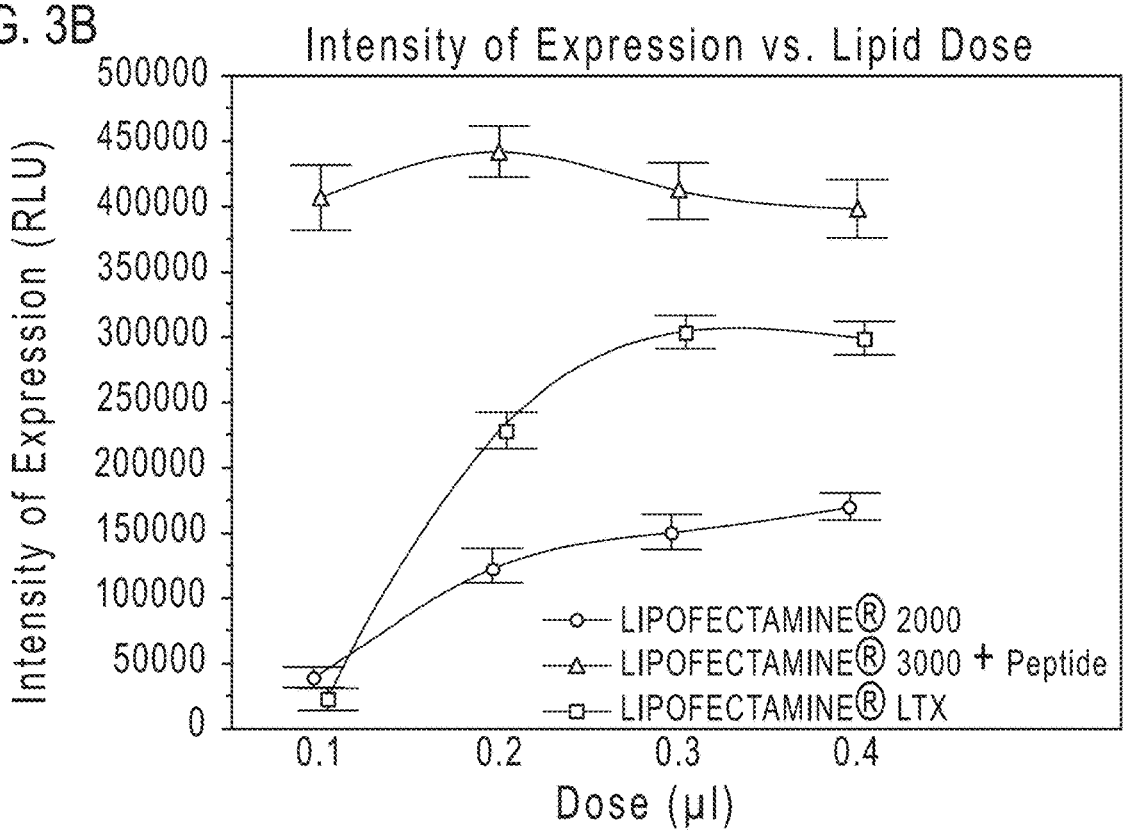
FIG. 3B is a graph comparing the intensity of GFP expression in HeLa cells transfected with an expression vector encoding GFP using increasing dosage of three different commercially available lipid aggregate formulations, LIPOFECTAMINE® 2000 (open circles), LIPOFECTAMINE® LTX (open squares), and LIPOFECTAMINE® 3000 in combination with a peptide according to an embodiment (open triangles)

FIG. 3B is a graph comparing the intensity of GFP expression in HeLa cells transfected with an expression vector encoding GFP using increasing dosage of three different commercially available lipid aggregate formulations, LIPOFECTAMINE® 2000 (open circles), LIPOFECTAMINE® LTX (open squares), and LIPOFECTAMINE® 3000 in combination with a peptide according to an embodiment (open triangles). The presence of Peptide 1 in the transfection complex improves relative expression of GFP in the cells over the entire range of transfection reagent dosages tested. The improvement in protein expression is particular pronounce at the lowest tested dosage.

Example 5. Improvement in Protein Expression Compared to Three Commercially Available Transfection Reagents HepG2 cells were transfected in 24-well plates with an expression vector encoding a GST-STAT fusion protein using LIPOFECTAMINE® 2000, FUGENE® HD, X-TREMEGENE™ HP or LIPOFECTAMINE® 3000 in combination with Peptide 1 as described in Example 1. Approximately 24 hrs after transfection, cell lysates were prepared using NOVEX® Cell Extraction Buffer (Life Technologies, Carlsbad, CA) and the lysates were resolved by SDS-PAGE electrophoresis, transferred to PVDF membranes, immunoblotted with an anti-GST HRP-labeled polyclonal antibody, and detected with Pierce™ ECL Western Blotting Substrate (Pierce Biotechnology, Rockford, IL).

Figure 4:
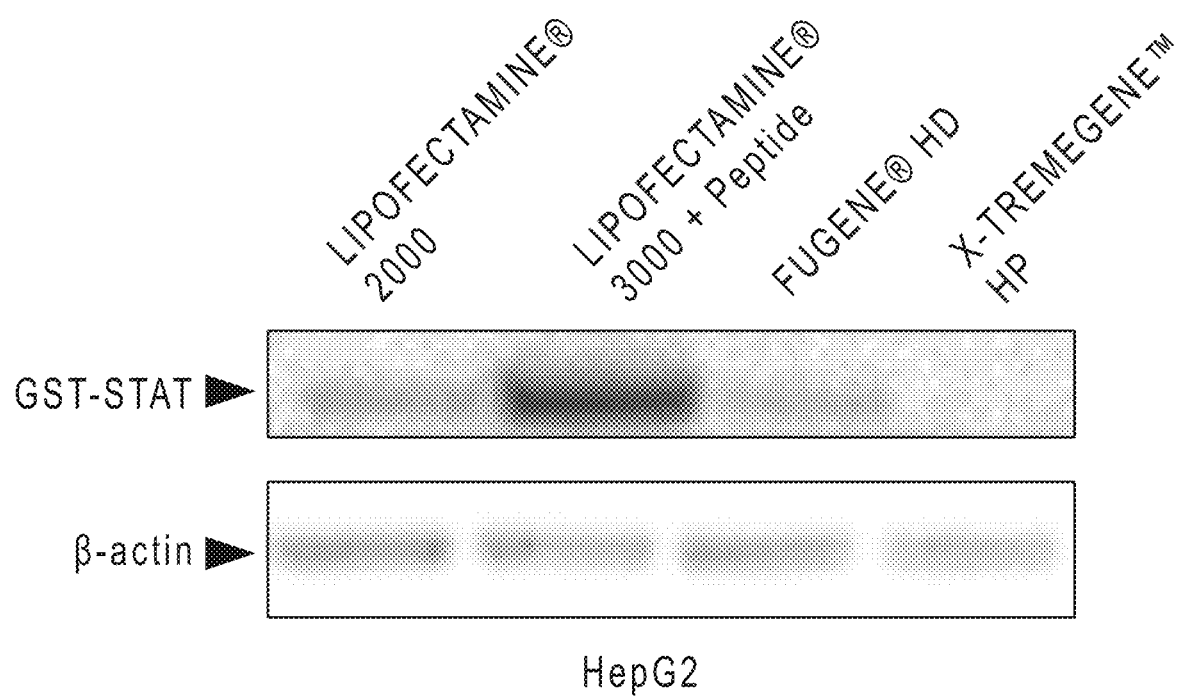
FIG. 4 is a Western blot comparing the relative expression levels of a GST-STAT fusion protein (upper panel) in HepG2 cells transfected with an expression vector encoding a GST-STAT fusion protein using the following commercially available lipid aggregate formulations: LIPOFECTAMINE® 2000 (first lane), LIPOFECTAMINE® 3000 in combination with a peptide according to one embodiment (second lane), FUGENE® HD (third lane), and X-TREMEGENE™ HP (last lane). The bottom panel shows a western blot of endogenous β-actin to confirm equal loading of cytosolic extract in each lane.

FIG. 4 is a Western blot comparing the relative expression levels of a GST-STAT fusion protein (upper panel) in HepG2 cells transfected with an expression vector encoding a GST-STAT fusion protein using the following commercially available lipid aggregate formulations: LIPOFECTAMINE® 2000 (first lane), LIPOFECTAMINE®

3000 in combination with a peptide according to one embodiment (second lane), FUGENE® HD (third lane), and X-TREMEGENE™ HP (last lane). The bottom panel shows a western blot of endogenous β-actin to confirm equal loading of cytosolic extract in each lane.

Example 6. Transfection of H9 Human Embryonic Stem Cell Line

H9 Human embryonic stem cell line were seeded at a density of 37500 cells/well in each well of a 96-well plate and transfected with 50 µg, 100 m or 200 m of pcDNAEF1a/emGFP using 0.1 µl to 0.6 µl per well of either LIPOFECTAMINE® 2000 or LIPOFECTAMINE® 3000 in combination with Peptide 1 as described in Example 1. After 24 hrs transfection, transfection efficiency was determined.

Figure 5A:
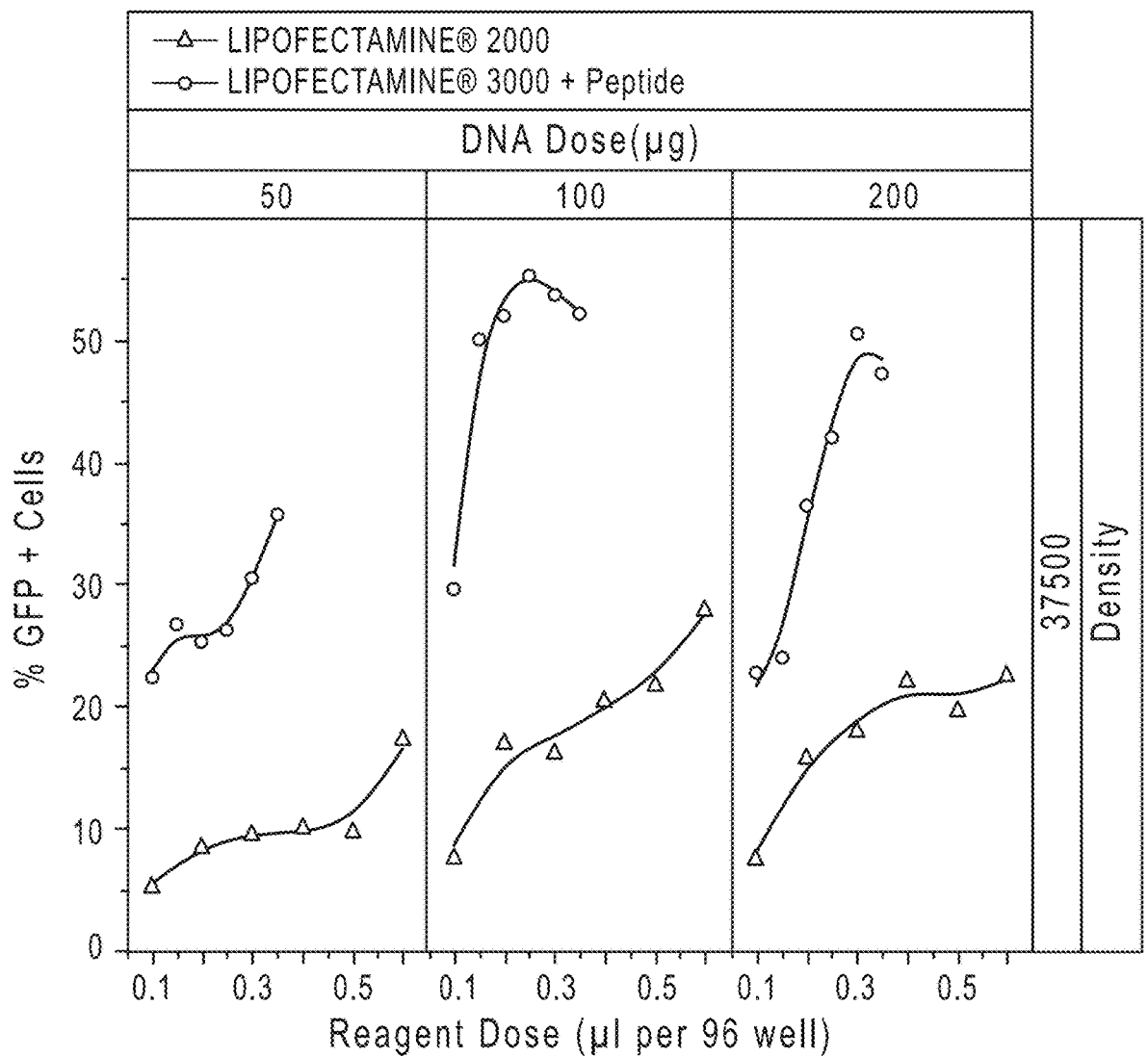
FIG. 5A is a graph comparing relative transfection efficiency of the H9 human embryonic stem cell line (37,500 cells per well of a 96 well plate) transfected with increasing dose of a GFP expression vector (50 µg, left panel; 100 µg center panel, and 200 µg right panel) and using between 0.1 to 0.6 µl per well of either LIPOFECTAMINE® 2000 (open triangles) or LIPOFECTAMINE® 3000 in combination with a peptide according to an embodiment.
Figure 5B:
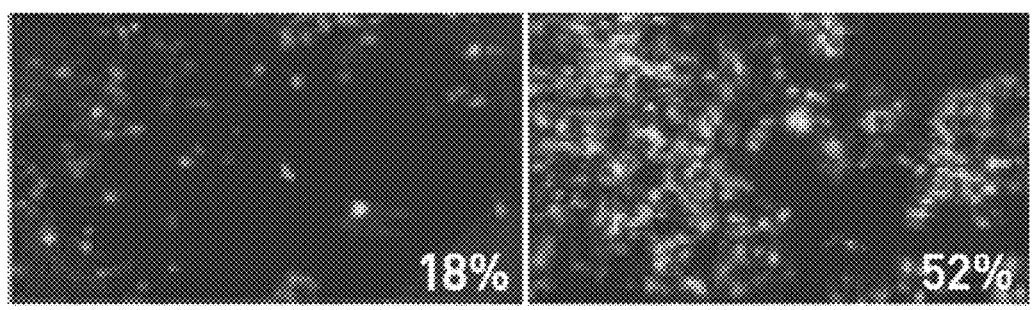
FIG. 5B is a representative fluorescence image of GFP expression in H9 cells cultured in 96 well plates transfected with 100 µg/well using 200 µl of either LIPOFECTAMINE® 2000 (left panel, demonstrating 18% transfection efficiency of H9 cells) or LIPOFECTAMINE® 3000 in combination with a peptide according to an embodiment (right panel)

FIG. 5A is a graph comparing relative transfection efficiency of the H9 human embryonic stem cell line (37,500 cells per well of a 96 well plate) transfected with increasing dose of a GFP expression vector (50 µg, left panel; 100 µg center panel, and 200 µg right panel) and using between 0.1 to 0.6 µl per well of either LIPOFECTAMINE® 2000 (open triangles) or LIPOFECTAMINE® 3000 in combination with a peptide according to an embodiment;

FIG. 5B is a representative fluorescence image of GFP expression in H9 cells cultured in 96 well plates transfected with 100 µg/well using 200 µl of either LIPOFECTAMINE® 2000 (left panel, demonstrating 18% transfection efficiency of H9 cells) or LIPOFECTAMINE® 3000 in combination with a peptide according to an embodiment (right panel, demonstrating 52% transfection efficiency of H9 cells).

Example 7. Genomic Modification of Cells Using CRISPR Nuclease Vector System

Plasmid design and preparation: GENEART® Precision TALs and GENEART® CRISPR Nuclease Vectors were designed using the Life Technologies GENEART® web design tool (lifetechnologies.com/us/en/home/life-science/cloning/gene-synthesis/geneart-precision-tals.html). The forward and reverse TALENs contain the FokI nuclease and target the AAVS1 safe harbor locus. The all-in-one CRISPR vector system contains a Cas9 nuclease expression cassette and a guide RNA cloning cassette that target the AAVS1 safe harbor locus, combined with a downstream orange fluorescent protein (OFP) reporter. A negative control plasmid, PCDNA™ 3.3, was also used throughout the assay. The plasmids were transformed into competent *E. coli* cells. Clones were analyzed and sequenced for specificity and then purified using a PURELINK® HiPure Plasmid Filter Maxiprep Kit to ensure low endotoxin activity and high-quality DNA.

U2OS and HepG2 cells were cultured using GIBCO® DMEM, high-glucose, with GLUTAMAX™ Supplement and 10% fetal bovine serum for 4-5 passages after thawing; cells were dissociated using TRYPLE™ Express dissociation enzyme and seeded in a 12-well plate at $2 \times 10^5$ cells per well in 1 mL complete medium to ensure 70-90% confluence on the day of transfection.

Transfection with LIPOFECTAMINE® 3000 Reagent in combination with Peptide 1 and LIPOFECTAMINE® 2000 Reagent was compared in each cell type. For transfection with LIPOFECTAMINE® 3000 Reagent, in separate tubes, 1.5 µL of LIPOFECTAMINE® 3000 Reagent and 1 µg of plasmid DNA were each diluted in 50 µL OPTI-MEM® Reduced-Serum Medium; then 2 µL Peptide 1 (see Example 1) was added to the diluted DNA. The diluted DNA with Peptide 1 was added to the diluted LIPOFECTAMINE® 3000 Reagent and incubated at room temperature for 5 minutes. Then 100 µL of the resulting complex was added to cells in complete medium. The procedure was the same for LIPOFECTAMINE® 2000 Reagent, except that the amount of transfection reagent was increased to 3 µL and no Peptide 1 was added to the diluted DNA before adding it to the diluted LIPOFECTAMINE® 2000 Reagent. All downstream analysis was performed 72 hours post-transfection.

OFP expression from the CRISPR vector was determined by flow cytometry and microscopy. An EVOS® FL Imaging System was used to acquire images with the RFP filter. Cells were then dissociated 72 hours post-transfection with TRYPLE™ Express enzyme and analyzed using a BD ACCURI™ C6 Flow Cytometer with an FL-2 filter and blue laser.

Figure 6A:
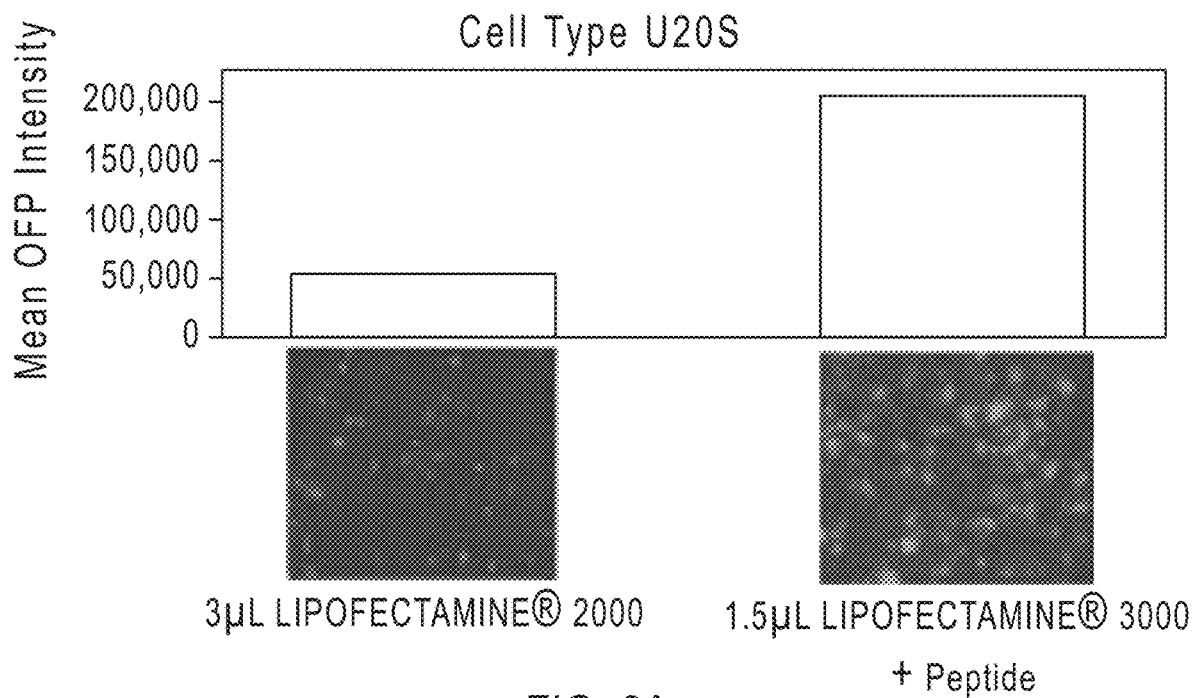
FIG. 6A shows the genomic modification efficiency of U2OS cells using a commercially available system as measured by mean Orange Fluorescent protein (OFP) intensity (bar graph, upper panel) and representative fluorescence images (lower panel) of OFP expression in modified U2OS cells using the indicated about of LIPOFECTAMINE® 2000 or LIPOFECTAMINE® 3000 in combination with a peptide according to an embodiment.
Figure 6B:
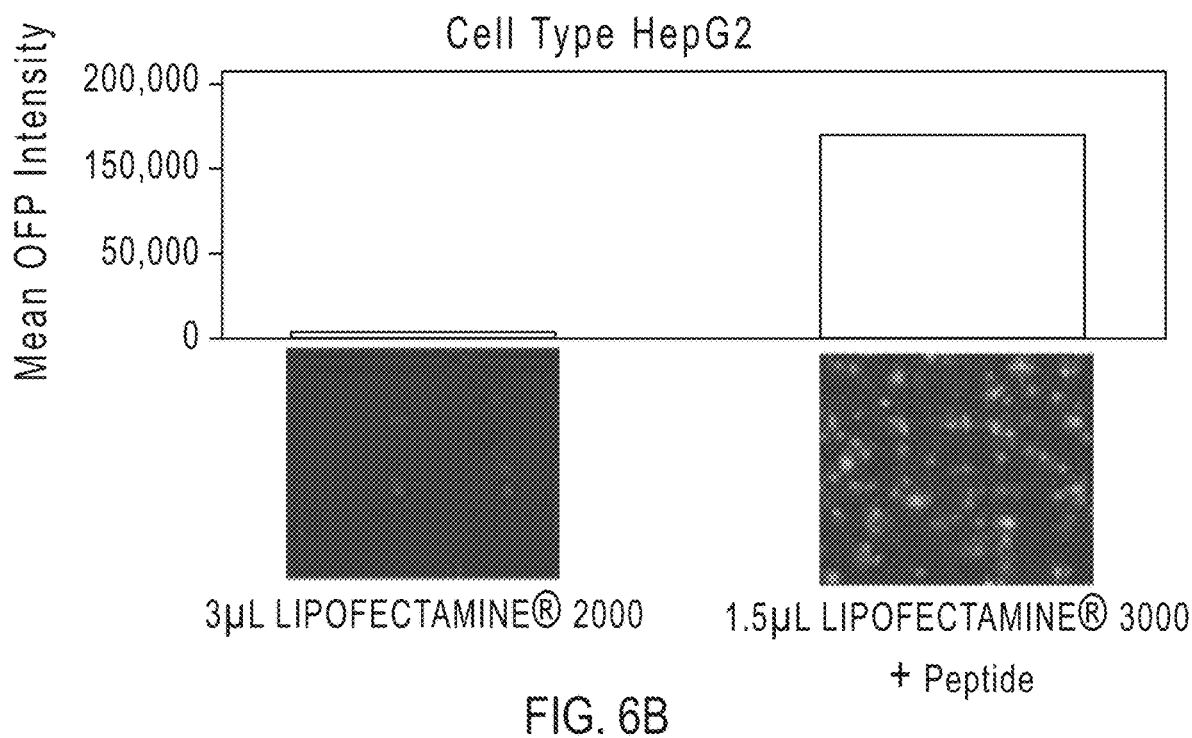
FIG. 6B shows the genomic modification efficiency of HepG2 cells using a commercially available system as measured by mean OFP intensity (bar graph, upper panel) and representative fluorescence images (lower panel) of OFP expression in modified HepG2 cells using the indicated about of LIPOFECTAMINE® 2000 or LIPOFECTAMINE® 3000 in combination with a peptide according to an embodiment.

FIG. 6 shows transfection efficiency and protein expression using a CRISPR vector in U2OS cells (FIG. 6A) and HepG2 cells (FIG. 6B). The vector contained an OFP reporter gene and was transfected with LIPOFECTAMINE® 2000 or LIPOFECTAMINE® 3000 reagent into in combination with Peptide 1. Bar graphs show relative OFP gene expression (measured by fluorescence intensity) and fluorescence images below the bar graphs show quantified fluorescence intensity of corresponding cells expressing OFP.

Genomic cleavage detection: The GENEART® Genomic Cleavage Detection Kit provides a reliable and rapid method for the detection of locus-specific cleavage. Transfected cells were dissociated with TRYPLE™ Express, washed with Dulbecco's phosphate buffered saline, and pelleted by centrifugation. Cells were lysed with the Cell Lysis Buffer and Protein Degrader Mix from the GENEART® Genomic Cleavage Detection Kit. The DNA was extracted and then PCR-amplified with forward and reverse primers. Denaturing and re-annealing reactions were then performed to randomly anneal the mutated and un-mutated PCR fragments. Detection enzyme (1 µL) was added, the mix was incubated for 1 hour at 37° C., and then the entire mix was electrophoresed in an E-Gel® EX 2% agarose gel to determine the percent genome modification. ALPHAVIEW™ Software was used to determine cleavage efficiency using the following formula: cleavage efficiency=$1-[(1-\text{fraction cleaved})^{1/2}]$.

Figure 7A:
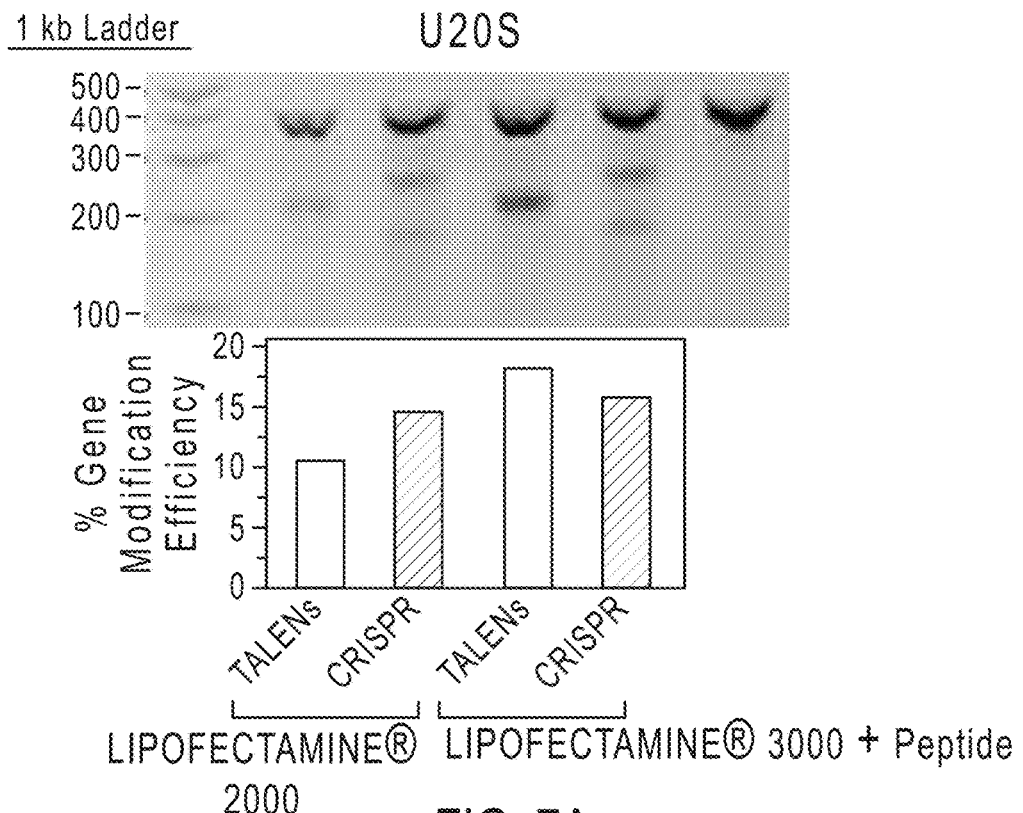
FIG. 7A shows the cleavage efficiency for TALENs and CRISPRs targeting the AAVS1 locus in U2OS cells using either LIPOFECTAMINE® 2000 or LIPOFECTAMINE® 3000 in combination with a peptide according to an embodiment.

FIG. 7A shows the cleavage efficiency for TALENs and CRISPRs targeting the AAVS1 locus in U2OS cells using either LIPOFECTAMINE® 2000 or LIPOFECTAMINE® 3000 in combination with Peptide 1 according to an embodiment.

Figure 7B:
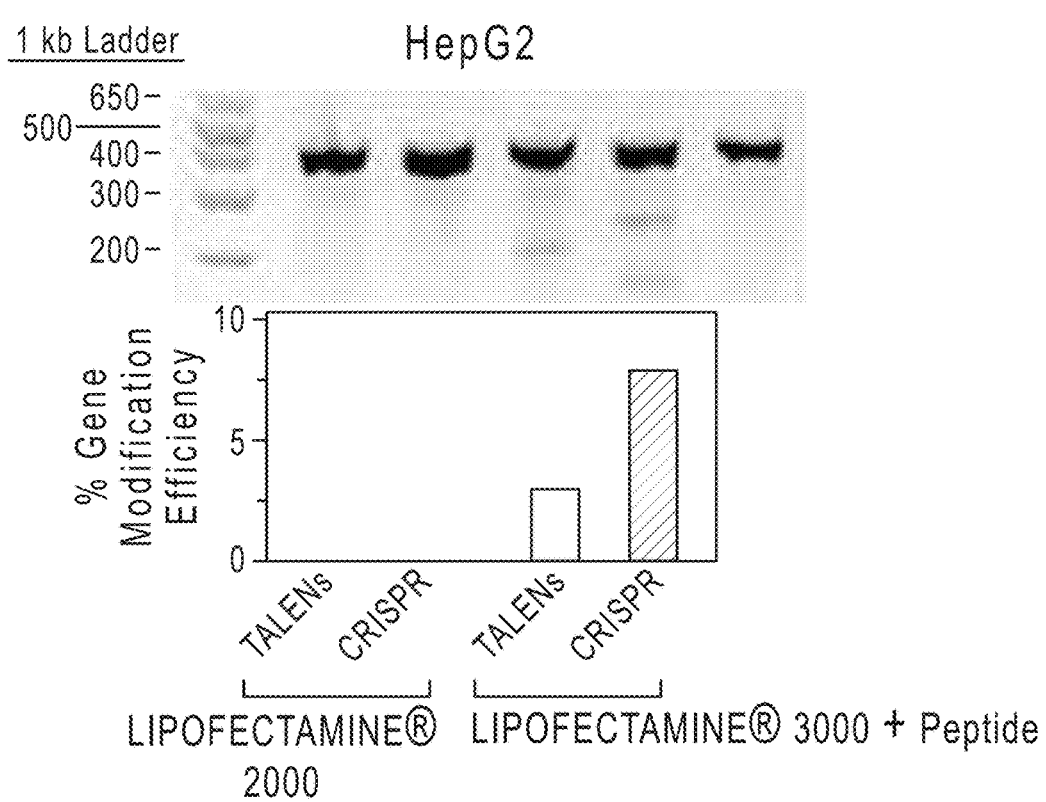
FIG. 7B shows the cleavage efficiency for TALENs and CRISPRs targeting the AAVS1 locus in HepG2 cells using either LIPOFECTAMINE® 2000 or LIPOFECTAMINE® 3000 in combination with a peptide according to an embodiment.

FIG. 7B shows the cleavage efficiency for TALENs and CRISPRs targeting the AAVS1 locus in HepG2 cells using either LIPOFECTAMINE® 2000 or LIPOFECTAMINE® 3000 in combination with Peptide 1 according to an embodiment.

Conclusion: U2OS cells, derived from human bone osteosarcoma, and HepG2 cells, derived from a human hepatocellular carcinoma, were transfected with LIPOFECTAMINE® 3000 and Peptide 1. Both cell lines showed improved transfection efficiency and protein expression compared to LIPOFECTAMINE® 2000-mediated transfection. Transfection efficiency and protein expression were assessed using a CRISPR construct that contains the OFP reporter gene. U2OS cells transfected with LIPOFECTAMINE® 3000 and Peptide 1 had 2-fold improved transfection efficiency (data not shown) and 4-fold improved fluorescence intensity (FIG. 6A). HepG2 cells showed 20-fold improvement in transfection efficiency (data not shown) and 80-fold higher fluorescence intensity (FIG. 6B). Significantly, increased TALEN- and CRISPR-mediated cleavage was seen for the AAVS1 target locus in both cell lines transfected with LIPOFECTAMINE® 3000 and Peptide 1, demonstrating that increasing the transfection efficiency and, by implication, protein expression, will increase the cleavage rate of TALENs and CRISPRs. U2OS cells transfected with LIPOFECTAMINE® 3000 and Peptide 1 showed 1.5-fold improved TALEN cleavage efficiency and slightly improved CRISPR cleavage (FIG. 7A). HepG2 cells had 3-fold higher cleavage efficiency for TALENs and 8-fold higher for CRISPRs (FIG. 7B).

Example 8. Lipid Transfection Reagent and Peptide are Required to Enhance Transfection HeLa cells were seeded onto 96-well plates and transfected for 48 hrs with 0.2 m/well of pcDNAEF1a/emGFP using either 0.05 µl, 0.1 µl, 0.2 µl, 0.3 µl, 0.4 µl, or 0.5 µl of LIPOFECTAMINE® 3000 Reagent alone (LF3K), LIPOFECTAMINE® 2000 (LF2K), Peptide 1 alone (Peptide 1), or LIPOFECTAMINE® 3000 in combination with Peptide 1 as described in Example 1 (LF3K+Peptide 1). Transfection efficiency and protein expression as measured by Fluorescence intensity (FL1-H) were determined. Results are depicted in FIG. 8.

Figure 8:
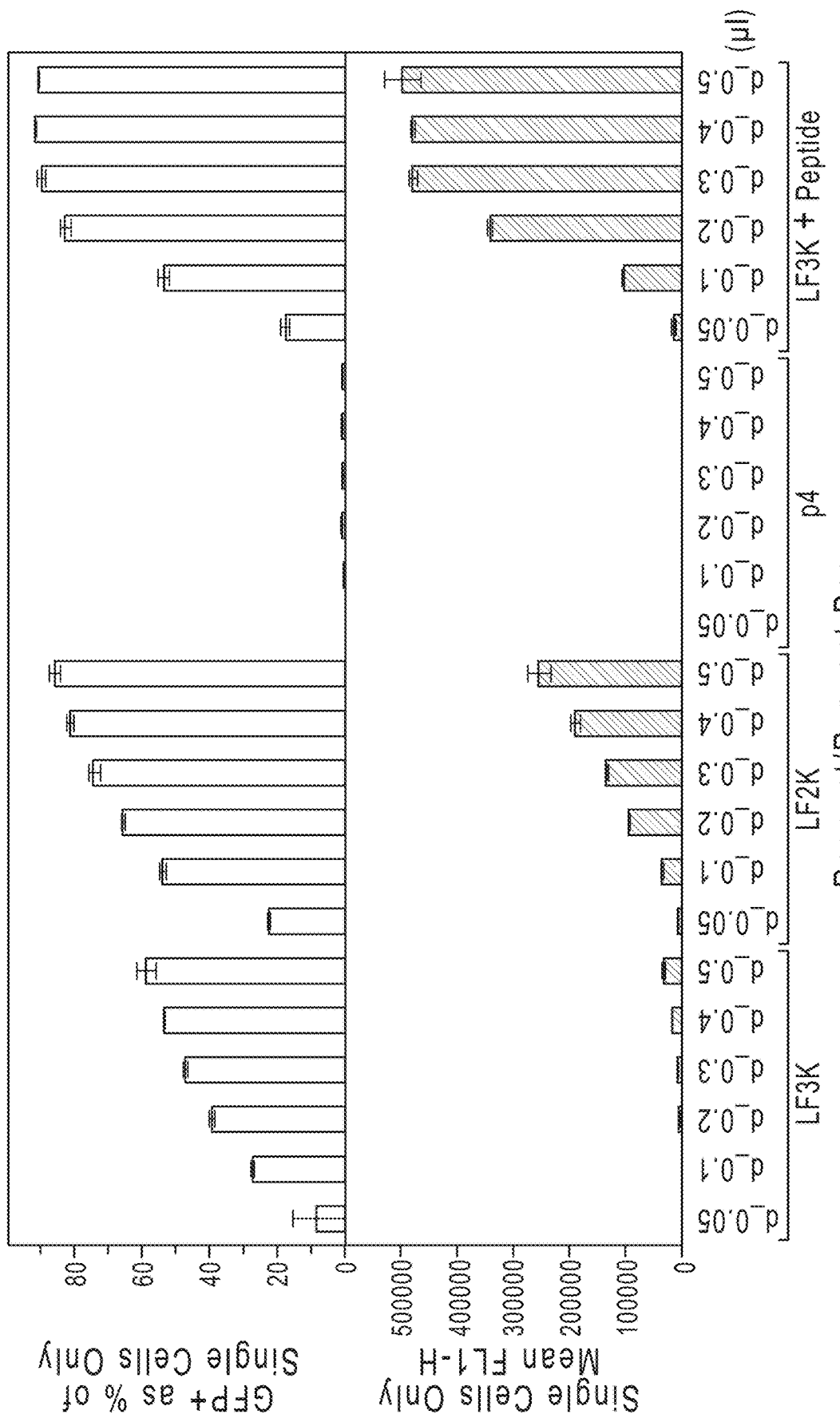
FIG. 8 are bar graphs depicting relative transfection efficiency (upper graph, GFP+ as % of Single Cells Only) or relative expression level per cell (lower graph; Single cells Only Mean FL-1) of HeLa cells transfected with a GFP expression vector using the indicated doses (in μl) of LIPOFECTAMINE® 3000 alone (LF3K), LIPOFECTAMINE® 2000 (LF2K), a peptide according to an embodiment (Peptide 1) or LIPOFECTAMINE® 3000 in combination with a peptide according to an embodiment (LF3K+ Peptide 1)

FIG. 8 shows two bar graphs depicting relative transfection efficiency (upper graph, GFP+ as % of Single Cells Only) or relative GFP expression level per cell (lower graph; Single cells Only Mean FL1-H) of HeLa cells transfected with a GFP expression vector using the indicated doses (in µl) of LIPOFECTAMINE® 3000 alone (LF3K), LIPOFECTAMINE® 2000 (LF2K), a peptide according to an embodiment (p4) or LIPOFECTAMINE® 3000 in combination with a peptide according to an embodiment (LF3K+peptide). The presence of Peptide 1 in the presence of a cationic lipid aggregate formulation (e.g., LIPOFECTAMINE® 3000) significantly enhances transfection efficiency and protein expression.

Example 9. Full-Length Peptides are Required for Optimal Transfection

Figure 9A:
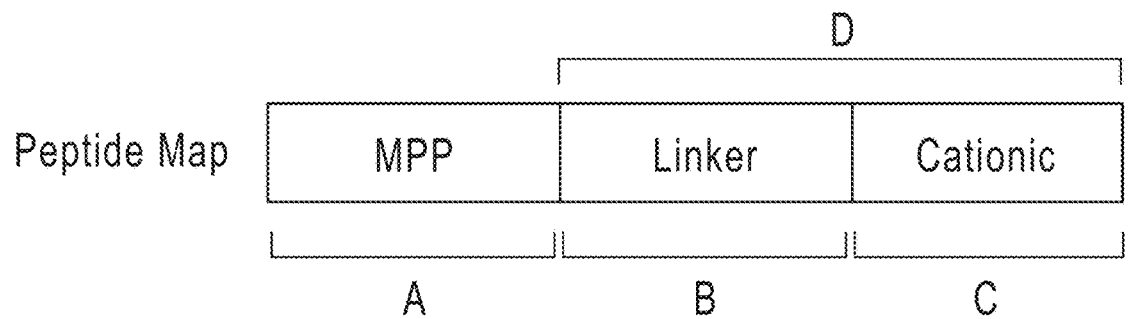
FIG. 9A is a depiction of a peptide map of various peptides or peptide fragments used in the experiments depicted in FIGS. 9B and 9C in HepG2 cells, in which Peptide A is the MPP Peptide alone, Peptide B is the Linker peptide alone, Peptide C is the Cationic peptide alone, Peptide D is the Linker peptide fused to the Cationic peptide, and peptide E is a full length peptide having Peptide A fused Peptide D.
Figure 10A:
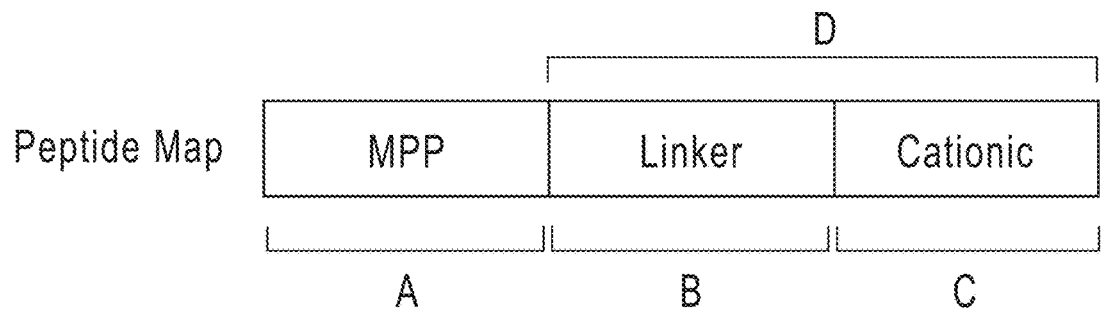
FIG. 10A is a depiction of a peptide map of various peptides or peptide fragments used in the experiments depicted in FIGS. 10B and 10C in A549 cells, in which Peptide A is the MPP Peptide alone, Peptide B is the Linker peptide alone, Peptide C is the Cationic peptide alone, Peptide D is the Linker peptide fused to the Cationic peptide, and peptide E is a full length peptide having Peptide A fused Peptide D.
Figure 11A:
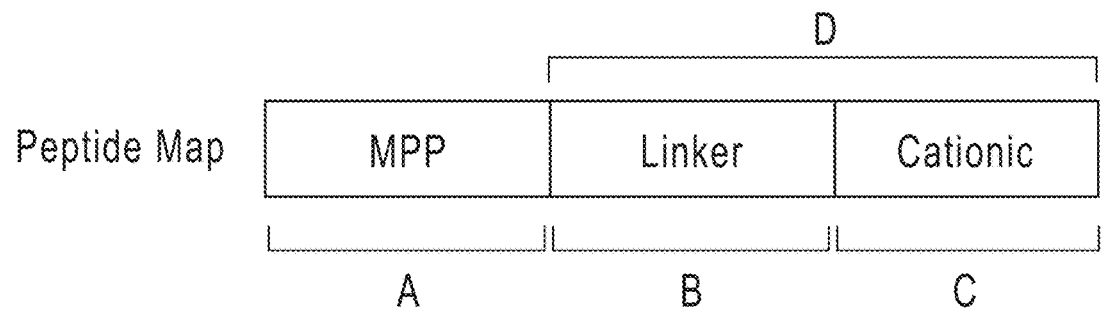
FIG. 11A is a depiction of a peptide map of various peptides or peptide fragments used in the experiments depicted in FIGS. 11B and 11C in MDA-MB-231 cells, in which Peptide A is the MPP Peptide alone, Peptide B is the Linker peptide alone, Peptide C is the Cationic peptide alone, Peptide D is the Linker peptide fused to the Cationic peptide, and peptide E is a full length peptide having Peptide A fused Peptide D.

The following peptides were outlined schematically in FIGS. 9A, 10A and 11A synthesized and dissolved in ultra-pure water as described in Example 1 for Peptide 1. Peptide A (corresponding to the MPP region of the non-naturally occurring peptides of the present invention) and having the peptide sequence SRRARRSPRESGKKRKRKR (SEQ ID NO. 1); Peptide B (corresponding to the Linker region of the non-naturally occurring peptides of the present invention) and having the peptide sequence GGGSGGGSGGGS (SEQ ID NO. 69); Peptide C (corresponding to the Cationic region of the non-naturally occurring peptides of the present invention) and having the peptide sequence of CP1 RRRRRRRRRRR (SEQ ID NO. 82); Peptide D (corresponding to the Linker region fused to the Cationic region of the non-naturally occurring peptides of the present invention) and having the peptide sequence GGGSGGGSGGGSRRRRRRRRRRR (SEQ ID NO. 108); and Peptide E, corresponding to Peptide 1 and having the sequence SRRARRSPRESGKKRKRKRGGGSGGGSGGGSRRRRRRRRRRR (SEQ ID NO. 89).

HepG2, A549 and MDA-MB-231 cells were seeded in 24-well plates and transfected for 48 hrs with 1 µg of pcDNAEF1a/emGFP using either LIPOFECTAMINE® 3000 Reagent in combination with Peptide A, Peptide B, Peptide C, Peptide D, Peptide A and B together, Peptide A and C together, Peptide A and D together, Peptide B and C together or Peptide E or Peptide A, Peptide B, Peptide C, Peptide D, Peptide A and B together, Peptide A and C together, Peptide A and D together, Peptide B and C together or Peptide E alone without a lipid transfection reagent. Cells were visualized using fluorescent microscopy and transfection efficiency as measured by percentage of GFP+cells and protein expression as measured by mean fluorescence per cell was determined as above. Results are summarized in FIGS. 9B, 9C, 10B, 10C, 11B, and 11C.

Figure 9B:
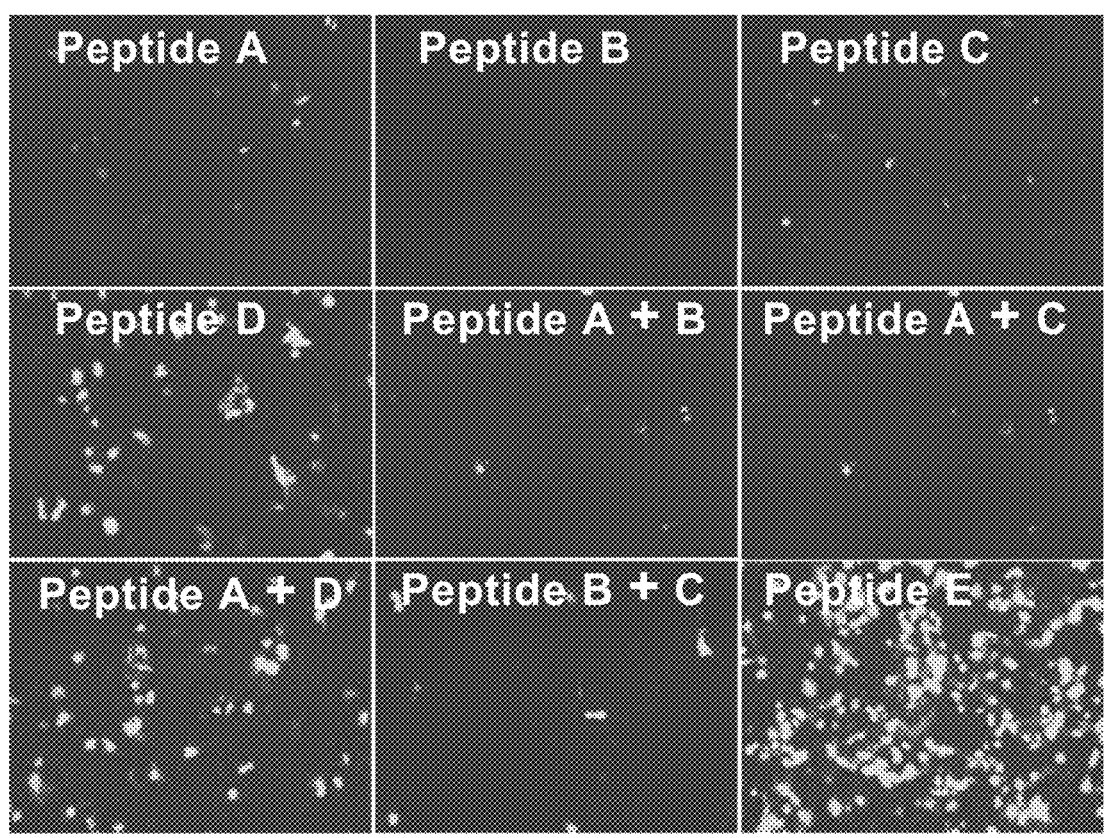
FIG. 9B depicts a series of fluorescence images to detect GFP expression in cultured HepG2 cells transfected with an expression vector encoding GFP using LIPOFECTAMINE® 3000 in the presence of the indicated peptide or combination of peptides (shown in FIG. 9A)

FIG. 9B depicts a series of fluorescence images to detect GFP expression in cultured HepG2 cells transfected with an expression vector encoding GFP using LIPOFECTAMINE® 3000 in the presence of the indicated peptide or combination of peptides (shown in FIG. 9A).

Figure 9C:
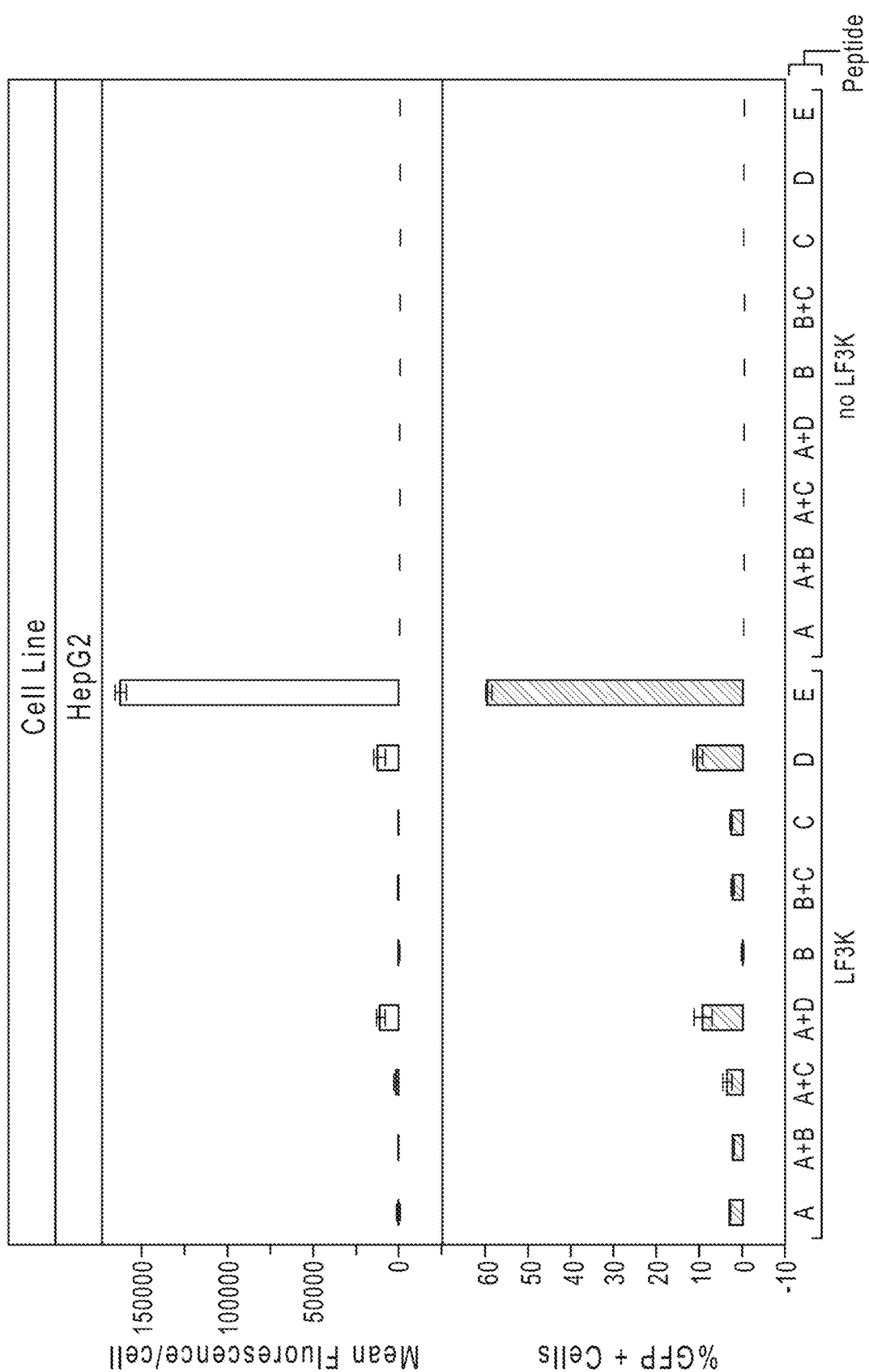
FIG. 9C depicts two bar graphs showing mean fluorescence per cell (upper graph) and transfection efficiency (% GFP+cells) in HepG2 cells transfected with an expression vector encoding GFP using LIPOFECTAMINE® 3000 in the presence of one of the indicated peptides A-E or the indicated combination of peptides (shown in FIG. 9A)

FIG. 9C depicts two bar graphs showing mean fluorescence per cell (upper graph) and transfection efficiency (% GFP+cells) in HepG2 cells transfected with an expression vector encoding GFP using LIPOFECTAMINE® 3000 in the presence of one of the indicated peptides A-E or the indicated combination of peptides (shown in FIG. 9A).

Figure 10B:
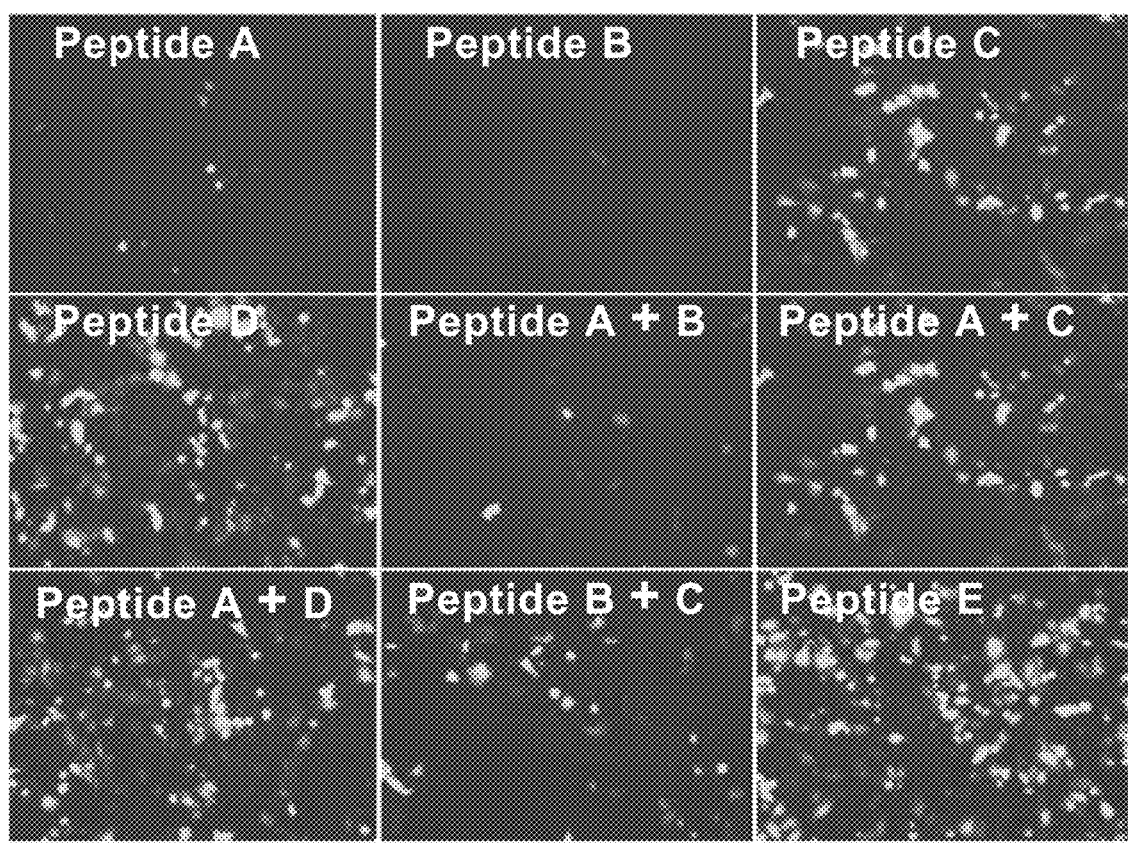
FIG. 10B depicts a series of fluorescence images to detect GFP expression in cultured A549 cells transfected with an expression vector encoding GFP transfected with LIPOFECTAMINE® 3000 in the presence of the indicated peptide or combination of peptides (shown in FIG. 10A)
Figure 10C:
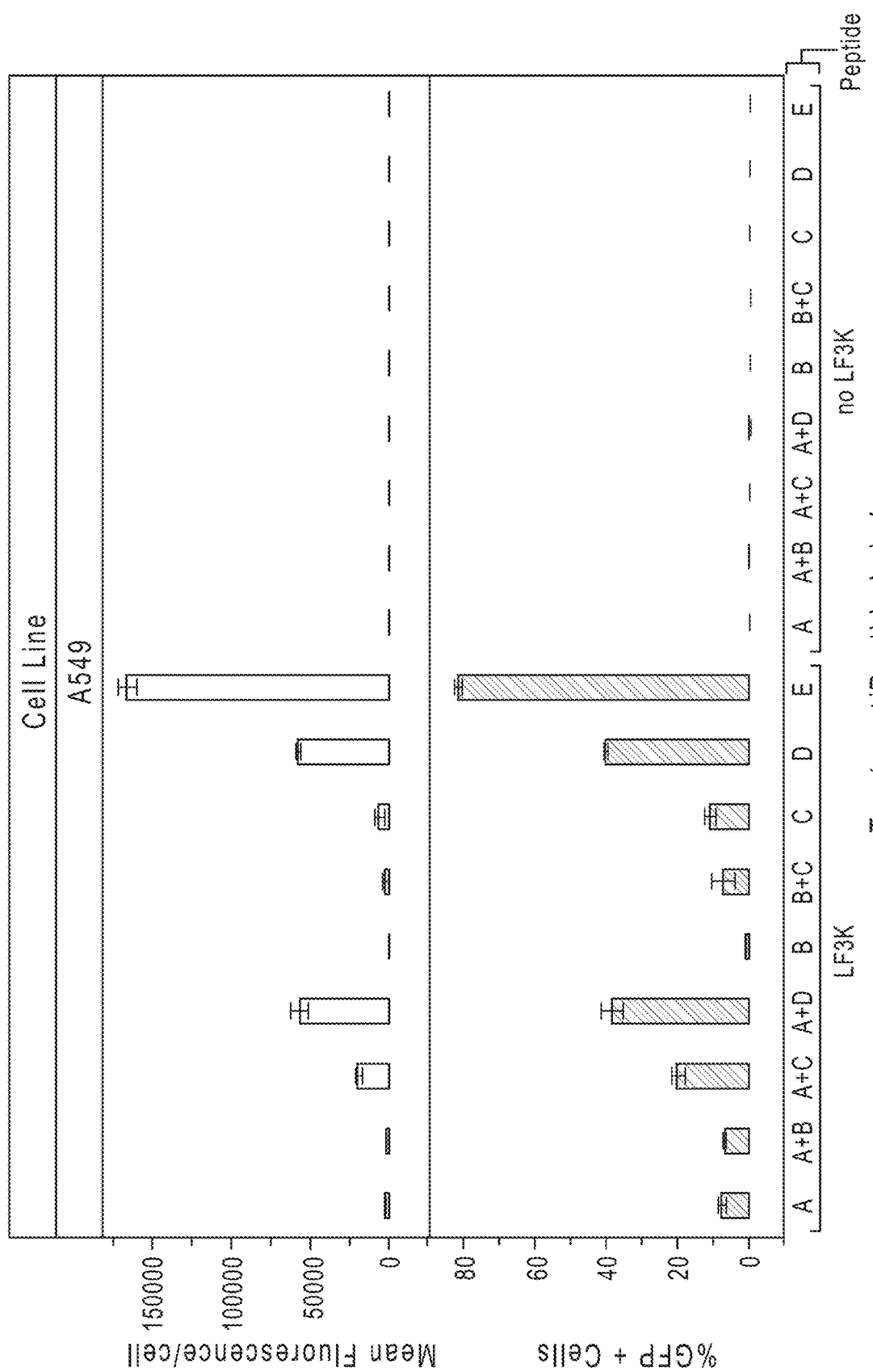
FIG. 10C depicts two bar graphs showing mean fluorescence per cell (upper graph) and transfection efficiency (% GFP+cells) in A549 cells transfected with an expression vector encoding GFP using LIPOFECTAMINE® 3000 in the presence of one of the indicated peptides A-E or the indicated combination of peptides (shown in FIG. 10A)

FIG. 10A is a depiction of a peptide map of various peptides or peptide fragments used in the experiments depicted in FIGS. 10B and 10C in A549 cells, in which Peptide A is the MPP Peptide alone, Peptide B is the Linker peptide alone, Peptide C is the Cationic peptide alone, Peptide D is the Linker peptide fused to the Cationic peptide, and peptide E is a full length peptide having Peptide A fused Peptide D.

FIG. 10B depicts a series of fluorescence images to detect GFP expression in cultured A549 cells transfected with an expression vector encoding GFP transfected with LIPOFECTAMINE® 3000 in the presence of the indicated peptide or combination of peptides (shown in FIG. 10A).

FIG. 10C depicts two bar graphs showing mean fluorescence per cell (upper graph) and transfection efficiency (% GFP+cells) in A549 cells transfected with an expression vector encoding GFP using LIPOFECTAMINE® 3000 in the presence of one of the indicated peptides A-E or the indicated combination of peptides (shown in FIG. 10A).

Figure 11B:
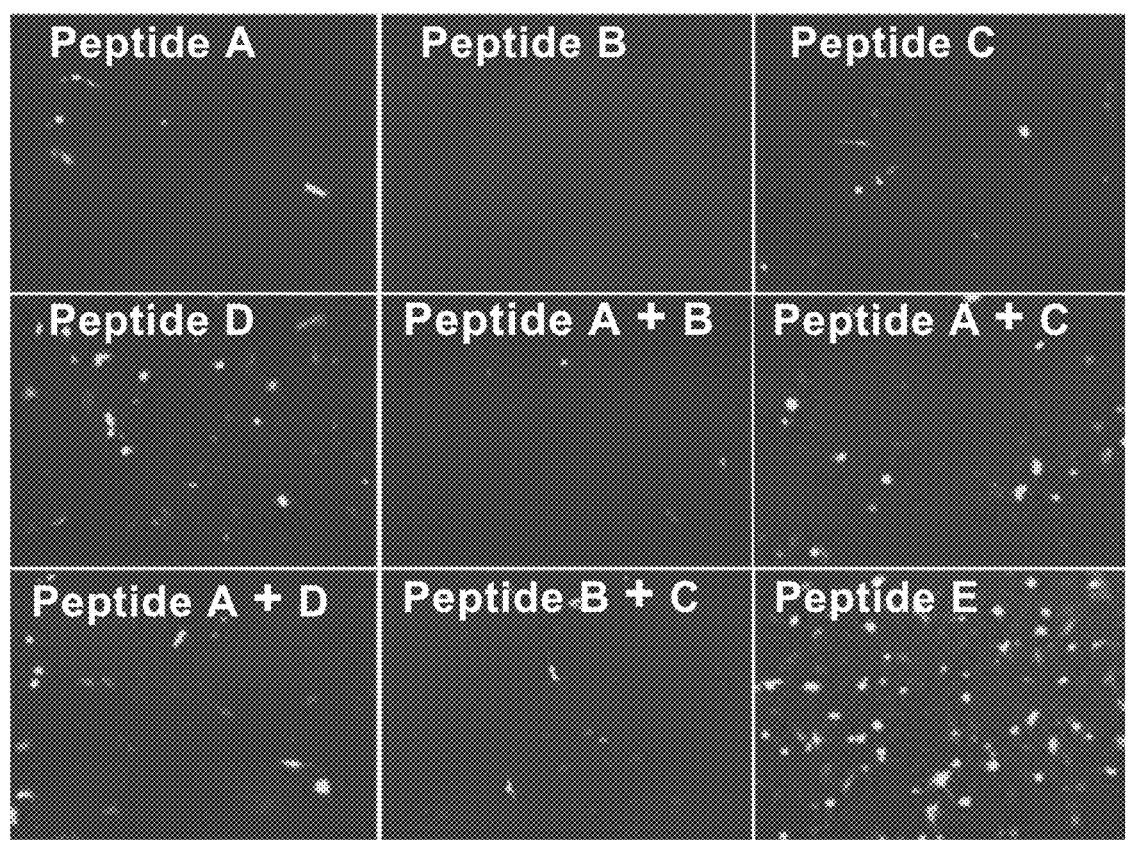
FIG. 11B depicts a series of fluorescence images to detect GFP expression in cultured MDA-MB-231 cells transfected with an expression vector encoding GFP transfected with LIPOFECTAMINE® 3000 in the presence of the indicated peptide or combination of peptides (shown in FIG. 11A)
Figure 11C:
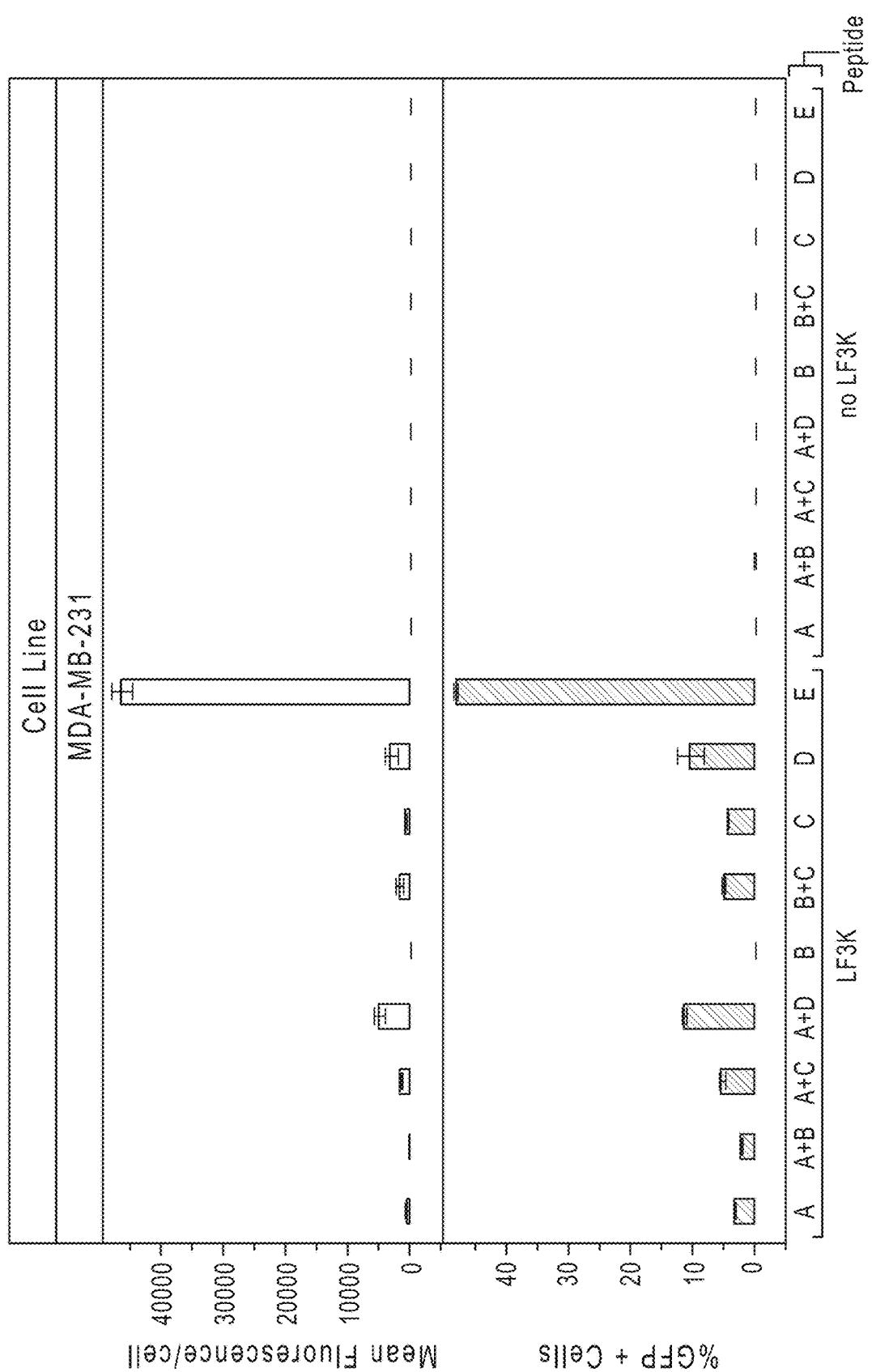
FIG. 11C depicts two bar graphs showing mean fluorescence per cell (upper graph) and transfection efficiency (% GFP+cells) in MDA-MB-231 cells transfected with an expression vector encoding GFP using LIPOFECTAMINE® 3000 in the presence of one of the indicated peptides A-E or the indicated combination of peptides (shown in FIG. 11A).

FIG. 11A is a depiction of a peptide map of various peptides or peptide fragments used in the experiments depicted in FIGS. 11B and 11C in MDA-MB-231 cells, in which Peptide A is the MPP Peptide alone, Peptide B is the Linker peptide alone, Peptide C is the Cationic peptide alone, Peptide D is the Linker peptide fused to the Cationic peptide, and peptide E is a full length peptide having Peptide A fused Peptide D.

FIG. 11B depicts a series of fluorescence images to detect GFP expression in cultured MDA-MB-231 cells transfected with an expression vector encoding GFP transfected with LIPOFECTAMINE® 3000 in the presence of the indicated peptide or combination of peptides (shown in FIG. 11A).

FIG. 11C depicts two bar graphs showing mean fluorescence per cell (upper graph) and transfection efficiency (% GFP+cells) in MDA-MB-231 cells transfected with an expression vector encoding GFP using LIPOFECTAMINE® 3000 in the presence of one of the indicated peptides A-E or the indicated combination of peptides (shown in FIG. 11A).

It will be readily apparent to one of ordinary skill in the relevant arts that other suitable modifications and adaptations to the methods and applications described herein are obvious and can be made without departing from the scope of the invention or any embodiment thereof. Having now described the present invention in detail, the same will be more clearly understood by reference to the following examples, which are included herewith for purposes of illustration only and are not intended to be limiting of the invention.

All publications, patents and patent applications mentioned in this specification are herein incorporated in their entirety by reference into the specification, to the same extent as if each individual publication, patent or patent application was specifically and individually indicated to be incorporated herein by reference. In case of conflict, the specification herein, including definitions, will control. Citation or identification of any reference in this application shall not be construed as an admission that such reference is available as prior art to the present invention.

What is claimed is:

1. A non-naturally occurring polypeptide having the structure:

A-L-B, or

B-L-A;

wherein;

A is membrane penetrating peptide sequence;

L is a linker peptide sequence comprising the structure $$-(X_m-Y_n)_p-\ \text{or}\ -(Y_n-X_m)_p-,$$

where each X is independently a neutral amino acid,
where each Y is independently a neutral polar amino acid,
where m is an integer from 3 to 50,
where n is an integer from 1 to 40, and
where p is an integer from 1 to 20; and B is peptide sequence comprising 5-30 positively charged amino acids.

2. The non-naturally occurring polypeptide according to claim 1, wherein A comprises a peptide sequence selected from any one of SEQ ID NO. 1-68.

3. The non-naturally occurring polypeptide according to claim 1, wherein A is a peptide sequence comprising 5 to about 50 amino acids.

4. The non-naturally occurring polypeptide according to claim 1, wherein A comprises a peptide sequence that is at least 75% similar to any one of SEQ ID NO. 1-68.

5. The non-naturally occurring polypeptide according to claim 1, wherein A comprises a peptide sequence that is at least 90% similar to any one of SEQ ID NO. 1-68.

6. The non-naturally occurring polypeptide according to claim 1, wherein A comprises a peptide sequence that is at least 90% similar to any one of SEQ ID NO. 1, SEQ ID NO. 3, SEQ ID NO. 4, SEQ ID NO. 13, SEQ ID NO. 14, SEQ ID NO. 53, SEQ ID NO. 58, SEQ ID NO. 67 and SEQ ID NO. 68.

7. The non-naturally occurring polypeptide according to claim 1, wherein L comprises a 4 to 50 amino acid sequence characterized in that at least 50% of the amino acids in the sequence are neutral.

8. The non-naturally occurring polypeptide according to claim 1, wherein where m>n.

9. The non-naturally occurring polypeptide according to claim 1, wherein each X is independently glycine, alanine, valine, leucine or isoleucine.

10. The non-naturally occurring polypeptide according to claim 1, wherein B is a peptide sequence having a net positive charge at physiologic pH.

11. The non-naturally occurring polypeptide according to claim 1, wherein B is a peptide sequence comprising 5-20 positively charged amino acids.

12. The non-naturally occurring polypeptide according to claim 1, wherein B comprises 5-20 Arg residues.

13. The non-naturally occurring polypeptide according to claim 1, wherein X is Gly and Y is Ser.

14. A composition comprising the non-naturally occurring peptide according to claim 1 and at least one cationic lipid or at least one cationic polymer.

15. The composition according to claim 14, further comprising at least one neutral lipid.

16. The composition according to claim 14, wherein the cationic lipid is selected from the group consisting of a piperazine-based lipid, N-[I-(2,3-dioleyloxy) propyl]-N,N,N-trimethylamonium chloride (DOTMA), dioleoylphosphatidylcholine (DOPE),1,2-Bis( oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC), dihydroxyl-dimyristylspermine tetrahydrochloride (DHDMS), hydroxyl-dimyristylspermine tetrahydrochloride (HDMD), cholesteryl (4'-trimethylammonio) butanoate (ChoTB), cetyltrimethylammonium bromide (CTAB), 1,2-dioleoyl-3-dimethyl-hydroxyethylammonium bromide (DORI), 1,2-dioleyloxypropyl-3-dimethyl-hydroxyethyl ammoniumbromide (DORIE), 1,2-dimyristyloxypropyl-3-dimethyl-hydroxyethyl ammonium bromide (DMRIE), O,O'-didodecyl-N-[p(2-trimethylammonioethyloxy) benzoyl]-N,N,N-trimethylammoniumchloride, spermine conjugated to one or more lipids (for example, 5-carboxyspermylglycine dioctadecylamide (DOGS), N,NI,NII,NIII-tetramethyl-N,NI,NII,NIIItet-rapalmitylspermine (TM-TPS) and dipalmitoylphosphatidylethanolamine 5-carboxyspermylaminde (DPPES)), lipopolylysine (polylysine conjugated to DOPE), TRIS(Tris(hydroxymethyl)aminomethane, tromethamine) conjugated fatty acids (TFAs) and/or peptides such as trilysyl-alanyl-TRIS mono-, di-, and tri-palmitate, (3ß-[N--(N',N'dimethylaminoethane)-carbamoyl] cholesterol (DC-Chol), N-(a-trimethylammonioacetyl)didodecyl-D-glutamate chloride (TMAG), dimethyl dioctadecylammonium bromide (DDAB), 2,3-dioleyloxy-N-[2(spermine-carboxamido) ethyl]-N,N-dimethyl-1-propanamininiumtrifluoroacetate (DOSPA) and combinations thereof.

17. The composition according to claim 14, further comprising at least one cargo molecule.

18. A non-naturally occurring peptide that has an amino acid sequence at least 75% similar to any one of SEQ ID NO. 89-100 and SEQ ID NO. 102-107.

19. The non-naturally occurring peptide according to claim 18, wherein the amino acid sequence is at least 85% similar any one of SEQ ID NO. 89-100 and SEQ ID NO. 102-107.

20. The non-naturally occurring peptide according to claim 18, wherein the amino acid sequence is selected from any one of SEQ ID NO. 89-100 and SEQ ID NO. 102-107.

* * * * *

```
                        SEQUENCE LISTING

<160> NUMBER OF SEQ ID NOS: 109

<210> SEQ ID NO 1
<211> LENGTH: 19
<212> TYPE: PRT
<213> ORGANISM: Unknown
<220> FEATURE:
<223> OTHER INFORMATION: Description of Unknown: DPV10/6 exemplary
      membrane penetrating peptide

<400> SEQUENCE: 1

Ser Arg Arg Ala Arg Arg Ser Pro Arg Glu Ser Gly Lys Lys Arg Lys
1               5                   10                  15

Arg Lys Arg

<210> SEQ ID NO 2
<211> LENGTH: 23
<212> TYPE: PRT
<213> ORGANISM: Unknown
<220> FEATURE:
<223> OTHER INFORMATION: Description of Unknown: DPV15b exemplary
      membrane penetrating peptide

<400> SEQUENCE: 2

Cys Gly Ala Tyr Asp Leu Arg Arg Arg Glu Arg Gln Ser Arg Leu Arg
1               5                   10                  15

Arg Arg Glu Arg Gln Ser Arg
            20

<210> SEQ ID NO 3
<211> LENGTH: 17
<212> TYPE: PRT
<213> ORGANISM: Unknown
<220> FEATURE:
<223> OTHER INFORMATION: Description of Unknown: YM-3 exemplary
      membrane penetrating peptide

<400> SEQUENCE: 3

Gly Tyr Gly Arg Lys Lys Arg Arg Gly Arg Arg Thr His Arg Leu
1               5                   10                  15

Pro

<210> SEQ ID NO 4
<211> LENGTH: 5
<212> TYPE: PRT
<213> ORGANISM: Unknown
<220> FEATURE:
<223> OTHER INFORMATION: Description of Unknown: Penetration exemplary
      membrane peptide

<400> SEQUENCE: 4

Ile Gly Cys Arg His
1               5

<210> SEQ ID NO 5
<211> LENGTH: 12
```

```
<212> TYPE: PRT
<213> ORGANISM: Human immunodeficiency virus
<220> FEATURE:
<223> OTHER INFORMATION: Tat(46-57) exemplary membrane penetrating
      peptide

<400> SEQUENCE: 5

Cys Tyr Gly Arg Lys Lys Arg Arg Gln Arg Arg Arg
1               5                   10

<210> SEQ ID NO 6
<211> LENGTH: 11
<212> TYPE: PRT
<213> ORGANISM: Unknown
<220> FEATURE:
<223> OTHER INFORMATION: Description of Unknown: LR11 exemplary
      membrane penetrating peptide

<400> SEQUENCE: 6

Arg Ile Leu Gln Gln Leu Leu Phe Ile His Phe
1               5                   10

<210> SEQ ID NO 7
<211> LENGTH: 22
<212> TYPE: PRT
<213> ORGANISM: Unknown
<220> FEATURE:
<223> OTHER INFORMATION: Description of Unknown: C45D18 exemplary
      membrane penetrating peptide

<400> SEQUENCE: 7

Asp Thr Trp Ala Gly Val Glu Ala Ile Ile Arg Ile Leu Gln Gln Leu
1               5                   10                  15

Leu Phe Ile His Phe Arg
            20

<210> SEQ ID NO 8
<211> LENGTH: 9
<212> TYPE: PRT
<213> ORGANISM: Unknown
<220> FEATURE:
<223> OTHER INFORMATION: Description of Unknown: Lyp-1 exemplary
      membrane penetrating peptide

<400> SEQUENCE: 8

Cys Gly Asn Lys Arg Thr Arg Gly Cys
1               5

<210> SEQ ID NO 9
<211> LENGTH: 9
<212> TYPE: PRT
<213> ORGANISM: Unknown
<220> FEATURE:
<223> OTHER INFORMATION: Description of Unknown: Lyp-2 exemplary
      membrane penetrating peptide

<400> SEQUENCE: 9

Cys Ala Gly Arg Arg Ser Ala Tyr Cys
1               5

<210> SEQ ID NO 10
<211> LENGTH: 14
<212> TYPE: PRT
<213> ORGANISM: Unknown
<220> FEATURE:
<223> OTHER INFORMATION: Description of Unknown: (42-38)(9-1)Crot
      exemplary membrane penetrating peptide
```

```
<400> SEQUENCE: 10

Gly Ser Gly Lys Lys Gly Gly Lys Lys His Cys Gln Lys Tyr
1               5                   10

<210> SEQ ID NO 11
<211> LENGTH: 14
<212> TYPE: PRT
<213> ORGANISM: Unknown
<220> FEATURE:
<223> OTHER INFORMATION: Description of Unknown: (1-9)(38-42)Crot
      exemplary membrane penetrating peptide

<400> SEQUENCE: 11

Tyr Lys Gln Cys His Lys Lys Gly Gly Lys Lys Gly Ser Gly
1               5                   10

<210> SEQ ID NO 12
<211> LENGTH: 21
<212> TYPE: PRT
<213> ORGANISM: Unknown
<220> FEATURE:
<223> OTHER INFORMATION: Description of Unknown: BMV GAG exemplary
      membrane penetrating peptide

<400> SEQUENCE: 12

Lys Met Thr Arg Ala Gln Arg Arg Ala Ala Ala Arg Arg Asn Arg Trp
1               5                   10                  15

Thr Ala Arg Gly Cys
            20

<210> SEQ ID NO 13
<211> LENGTH: 16
<212> TYPE: PRT
<213> ORGANISM: Unknown
<220> FEATURE:
<223> OTHER INFORMATION: Description of Unknown: hPER1-PTD(830-845)NLS
      exemplary membrane penetrating peptide

<400> SEQUENCE: 13

Gly Arg Arg His His Cys Arg Ser Lys Ala Lys Arg Ser Arg His His
1               5                   10                  15

<210> SEQ ID NO 14
<211> LENGTH: 22
<212> TYPE: PRT
<213> ORGANISM: Unknown
<220> FEATURE:
<223> OTHER INFORMATION: Description of Unknown: hLF1 exemplary
      membrane penetrating peptide

<400> SEQUENCE: 14

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 15
<211> LENGTH: 22
<212> TYPE: PRT
<213> ORGANISM: Unknown
<220> FEATURE:
<223> OTHER INFORMATION: Description of Unknown: hLF2 exemplary
      membrane penetrating peptide

<400> SEQUENCE: 15

Lys Cys Phe Gln Trp Gln Arg Asn Val Arg Lys Val Arg Gly Pro Pro
```

```
1               5                   10                  15

Val Ser Cys Ile Lys Arg
            20

<210> SEQ ID NO 16
<211> LENGTH: 22
<212> TYPE: PRT
<213> ORGANISM: Unknown
<220> FEATURE:
<223> OTHER INFORMATION: Description of Unknown: hLF3 exemplary
      membrane penetrating peptide

<400> SEQUENCE: 16

Lys Cys Phe Gln Trp Gln Arg Asn Ile Arg Lys Val Arg Gly Pro Pro
1               5                   10                  15

Val Ser Cys Ile Lys Arg
            20

<210> SEQ ID NO 17
<211> LENGTH: 22
<212> TYPE: PRT
<213> ORGANISM: Unknown
<220> FEATURE:
<223> OTHER INFORMATION: Description of Unknown: hLF4 exemplary
      membrane penetrating peptide
<220> FEATURE:
<221> NAME/KEY: MOD_RES
<222> LOCATION: (9)..(9)
<223> OTHER INFORMATION: Norvaline

<400> SEQUENCE: 17

Lys Cys Phe Gln Trp Gln Arg Asn Val Arg Lys Val Arg Gly Pro Pro
1               5                   10                  15

Val Ser Cys Ile Lys Arg
            20

<210> SEQ ID NO 18
<211> LENGTH: 22
<212> TYPE: PRT
<213> ORGANISM: Unknown
<220> FEATURE:
<223> OTHER INFORMATION: Description of Unknown: hLF5 exemplary
      membrane penetrating peptide

<400> SEQUENCE: 18

Lys Cys Phe Gln Trp Gln Arg Asn Leu Arg Lys Val Arg Gly Pro Pro
1               5                   10                  15

Val Ser Cys Ile Lys Arg
            20

<210> SEQ ID NO 19
<211> LENGTH: 22
<212> TYPE: PRT
<213> ORGANISM: Unknown
<220> FEATURE:
<223> OTHER INFORMATION: Description of Unknown: hLF6 exemplary
      membrane penetrating peptide
<220> FEATURE:
<221> NAME/KEY: MOD_RES
<222> LOCATION: (9)..(9)
<223> OTHER INFORMATION: Norleucine

<400> SEQUENCE: 19

Lys Cys Phe Gln Trp Gln Arg Asn Leu Arg Lys Val Arg Gly Pro Pro
1               5                   10                  15

Val Ser Cys Ile Lys Arg
```

```
<210> SEQ ID NO 20
<211> LENGTH: 18
<212> TYPE: PRT
<213> ORGANISM: Unknown
<220> FEATURE:
<223> OTHER INFORMATION: Description of Unknown: hLF7 exemplary
      membrane penetrating peptide

<400> SEQUENCE: 20

Cys Phe Gln Trp Gln Arg Asn Val Arg Lys Val Arg Gly Pro Pro Val
1               5                   10                  15

Ser Cys

<210> SEQ ID NO 21
<211> LENGTH: 18
<212> TYPE: PRT
<213> ORGANISM: Unknown
<220> FEATURE:
<223> OTHER INFORMATION: Description of Unknown: hLF8 exemplary
      membrane penetrating peptide

<400> SEQUENCE: 21

Cys Phe Gln Trp Gln Arg Asn Ile Arg Lys Val Arg Gly Pro Pro Val
1               5                   10                  15

Ser Cys

<210> SEQ ID NO 22
<211> LENGTH: 18
<212> TYPE: PRT
<213> ORGANISM: Unknown
<220> FEATURE:
<223> OTHER INFORMATION: Description of Unknown: hLF9 exemplary
      membrane penetrating peptide
<220> FEATURE:
<221> NAME/KEY: MOD_RES
<222> LOCATION: (8)..(8)
<223> OTHER INFORMATION: Norvaline

<400> SEQUENCE: 22

Cys Phe Gln Trp Gln Arg Asn Val Arg Lys Val Arg Gly Pro Pro Val
1               5                   10                  15

Ser Cys

<210> SEQ ID NO 23
<211> LENGTH: 18
<212> TYPE: PRT
<213> ORGANISM: Unknown
<220> FEATURE:
<223> OTHER INFORMATION: Description of Unknown: hLF10 exemplary
      membrane penetrating peptide

<400> SEQUENCE: 23

Cys Phe Gln Trp Gln Arg Asn Leu Arg Lys Val Arg Gly Pro Pro Val
1               5                   10                  15

Ser Cys

<210> SEQ ID NO 24
<211> LENGTH: 18
<212> TYPE: PRT
<213> ORGANISM: Unknown
<220> FEATURE:
<223> OTHER INFORMATION: Description of Unknown: hLF11 exemplary
      membrane penetrating peptide
<220> FEATURE:
```

```
<221> NAME/KEY: MOD_RES
<222> LOCATION: (8)..(8)
<223> OTHER INFORMATION: Norleucine

<400> SEQUENCE: 24

Cys Phe Gln Trp Gln Arg Asn Leu Arg Lys Val Arg Gly Pro Pro Val
1               5                   10                  15

Ser Cys

<210> SEQ ID NO 25
<211> LENGTH: 16
<212> TYPE: PRT
<213> ORGANISM: Unknown
<220> FEATURE:
<223> OTHER INFORMATION: Description of Unknown: hLF12 exemplary
      membrane penetrating peptide

<400> SEQUENCE: 25

Phe Gln Trp Gln Arg Asn Val Arg Lys Val Arg Gly Pro Pro Val Ser
1               5                   10                  15

<210> SEQ ID NO 26
<211> LENGTH: 16
<212> TYPE: PRT
<213> ORGANISM: Unknown
<220> FEATURE:
<223> OTHER INFORMATION: Description of Unknown: hLF13 exemplary
      membrane penetrating peptide

<400> SEQUENCE: 26

Phe Gln Trp Gln Arg Asn Ile Arg Lys Val Arg Gly Pro Pro Val Ser
1               5                   10                  15

<210> SEQ ID NO 27
<211> LENGTH: 16
<212> TYPE: PRT
<213> ORGANISM: Unknown
<220> FEATURE:
<223> OTHER INFORMATION: Description of Unknown: hLF14 exemplary
      membrane penetrating peptide
<220> FEATURE:
<221> NAME/KEY: MOD_RES
<222> LOCATION: (7)..(7)
<223> OTHER INFORMATION: Norvaline

<400> SEQUENCE: 27

Phe Gln Trp Gln Arg Asn Val Arg Lys Val Arg Gly Pro Pro Val Ser
1               5                   10                  15

<210> SEQ ID NO 28
<211> LENGTH: 16
<212> TYPE: PRT
<213> ORGANISM: Unknown
<220> FEATURE:
<223> OTHER INFORMATION: Description of Unknown: hLF15 exemplary
      membrane penetrating peptide

<400> SEQUENCE: 28

Phe Gln Trp Gln Arg Asn Leu Arg Lys Val Arg Gly Pro Pro Val Ser
1               5                   10                  15

<210> SEQ ID NO 29
<211> LENGTH: 16
<212> TYPE: PRT
<213> ORGANISM: Unknown
<220> FEATURE:
<223> OTHER INFORMATION: Description of Unknown: hLF16 exemplary
      membrane penetrating peptide
```

-continued

```
<220> FEATURE:
<221> NAME/KEY: MOD_RES
<222> LOCATION: (7)..(7)
<223> OTHER INFORMATION: Norleucine

<400> SEQUENCE: 29

Phe Gln Trp Gln Arg Asn Leu Arg Lys Val Arg Gly Pro Pro Val Ser
1               5                   10                  15

<210> SEQ ID NO 30
<211> LENGTH: 11
<212> TYPE: PRT
<213> ORGANISM: Unknown
<220> FEATURE:
<223> OTHER INFORMATION: Description of Unknown: hLF17 exemplary
      membrane penetrating peptide

<400> SEQUENCE: 30

Phe Gln Trp Gln Arg Asn Val Arg Lys Val Arg
1               5                   10

<210> SEQ ID NO 31
<211> LENGTH: 11
<212> TYPE: PRT
<213> ORGANISM: Unknown
<220> FEATURE:
<223> OTHER INFORMATION: Description of Unknown: hLF18 exemplary
      membrane penetrating peptide

<400> SEQUENCE: 31

Phe Gln Trp Gln Arg Asn Ile Arg Lys Val Arg
1               5                   10

<210> SEQ ID NO 32
<211> LENGTH: 11
<212> TYPE: PRT
<213> ORGANISM: Unknown
<220> FEATURE:
<223> OTHER INFORMATION: Description of Unknown: hLF19 exemplary
      membrane penetrating peptide
<220> FEATURE:
<221> NAME/KEY: MOD_RES
<222> LOCATION: (7)..(7)
<223> OTHER INFORMATION: Norvaline

<400> SEQUENCE: 32

Phe Gln Trp Gln Arg Asn Val Arg Lys Val Arg
1               5                   10

<210> SEQ ID NO 33
<211> LENGTH: 11
<212> TYPE: PRT
<213> ORGANISM: Unknown
<220> FEATURE:
<223> OTHER INFORMATION: Description of Unknown: hLF20 exemplary
      membrane penetrating peptide

<400> SEQUENCE: 33

Phe Gln Trp Gln Arg Asn Leu Arg Lys Val Arg
1               5                   10

<210> SEQ ID NO 34
<211> LENGTH: 11
<212> TYPE: PRT
<213> ORGANISM: Unknown
<220> FEATURE:
<223> OTHER INFORMATION: Description of Unknown: hLF21 exemplary
      membrane penetrating peptide
<220> FEATURE:
```

```
<221> NAME/KEY: MOD_RES
<222> LOCATION: (7)..(7)
<223> OTHER INFORMATION: Norleucine

<400> SEQUENCE: 34

Phe Gln Trp Gln Arg Asn Leu Arg Lys Val Arg
1               5                   10

<210> SEQ ID NO 35
<211> LENGTH: 18
<212> TYPE: PRT
<213> ORGANISM: Unknown
<220> FEATURE:
<223> OTHER INFORMATION: Description of Unknown: hLF22 exemplary
      membrane penetrating peptide

<400> SEQUENCE: 35

Cys Phe Gln Trp Gln Arg Asn Met Arg Lys Val Arg Gly Pro Pro Val
1               5                   10                  15

Ser Cys

<210> SEQ ID NO 36
<211> LENGTH: 27
<212> TYPE: PRT
<213> ORGANISM: Unknown
<220> FEATURE:
<223> OTHER INFORMATION: Description of Unknown: C45D18 exemplary
      membrane penetrating peptide

<400> SEQUENCE: 36

Asp Thr Trp Ala Gly Val Glu Ala Ile Ile Arg Ile Leu Gln Gln Leu
1               5                   10                  15

Leu Phe Ile His Phe Arg Ile Gly Cys Arg His
            20                  25

<210> SEQ ID NO 37
<211> LENGTH: 20
<212> TYPE: PRT
<213> ORGANISM: Unknown
<220> FEATURE:
<223> OTHER INFORMATION: Description of Unknown: LR20 exemplary
      membrane penetrating peptide

<400> SEQUENCE: 37

Arg Ile Leu Gln Gln Leu Leu Phe Ile His Phe Arg Ile Gly Cys Arg
1               5                   10                  15

His Ser Arg Ile
            20

<210> SEQ ID NO 38
<211> LENGTH: 17
<212> TYPE: PRT
<213> ORGANISM: Unknown
<220> FEATURE:
<223> OTHER INFORMATION: Description of Unknown: LR17 exemplary
      membrane penetrating peptide

<400> SEQUENCE: 38

Arg Ile Leu Gln Gln Leu Leu Phe Ile His Phe Arg Ile Gly Cys Arg
1               5                   10                  15

His

<210> SEQ ID NO 39
<211> LENGTH: 15
<212> TYPE: PRT
```

```
<213> ORGANISM: Unknown
<220> FEATURE:
<223> OTHER INFORMATION: Description of Unknown: LR15 exemplary
      membrane penetrating peptide

<400> SEQUENCE: 39

Arg Ile Leu Gln Gln Leu Leu Phe Ile His Phe Arg Ile Gly Cys
1               5                   10                  15

<210> SEQ ID NO 40
<211> LENGTH: 10
<212> TYPE: PRT
<213> ORGANISM: Unknown
<220> FEATURE:
<223> OTHER INFORMATION: Description of Unknown: LR15DL exemplary
      membrane penetrating peptide

<400> SEQUENCE: 40

Arg Ile Phe Ile His Phe Arg Ile Gly Cys
1               5                   10

<210> SEQ ID NO 41
<211> LENGTH: 8
<212> TYPE: PRT
<213> ORGANISM: Unknown
<220> FEATURE:
<223> OTHER INFORMATION: Description of Unknown: LR8DHF exemplary
      membrane penetrating peptide

<400> SEQUENCE: 41

Arg Ile Phe Ile Arg Ile Gly Cys
1               5

<210> SEQ ID NO 42
<211> LENGTH: 6
<212> TYPE: PRT
<213> ORGANISM: Unknown
<220> FEATURE:
<223> OTHER INFORMATION: Description of Unknown: LR8DHFRI exemplary
      membrane penetrating peptide

<400> SEQUENCE: 42

Arg Ile Phe Ile Gly Cys
1               5

<210> SEQ ID NO 43
<211> LENGTH: 6
<212> TYPE: PRT
<213> ORGANISM: Unknown
<220> FEATURE:
<223> OTHER INFORMATION: Description of Unknown: LR8DRIHF exemplary
      membrane penetrating peptide

<400> SEQUENCE: 43

Phe Ile Arg Ile Gly Cys
1               5

<210> SEQ ID NO 44
<211> LENGTH: 12
<212> TYPE: PRT
<213> ORGANISM: Human immunodeficiency virus
<220> FEATURE:
<223> OTHER INFORMATION: Tat exemplary membrane penetrating peptide

<400> SEQUENCE: 44

Tyr Gly Arg Lys Lys Lys Arg Arg Gln Arg Arg Arg
1               5                   10
```

```
<210> SEQ ID NO 45
<211> LENGTH: 9
<212> TYPE: PRT
<213> ORGANISM: Unknown
<220> FEATURE:
<223> OTHER INFORMATION: Description of Unknown: deltaNTat exemplary
      membrane penetrating peptide

<400> SEQUENCE: 45

Arg Lys Lys Arg Arg Gln Arg Arg Arg
1               5

<210> SEQ ID NO 46
<211> LENGTH: 16
<212> TYPE: PRT
<213> ORGANISM: Unknown
<220> FEATURE:
<223> OTHER INFORMATION: Description of Unknown: Antp exemplary
      membrane penetrating peptide

<400> SEQUENCE: 46

Arg Gln Ile Lys Ile Trp Phe Gln Asn Arg Arg Met Lys Trp Lys Lys
1               5                   10                  15

<210> SEQ ID NO 47
<211> LENGTH: 18
<212> TYPE: PRT
<213> ORGANISM: Unknown
<220> FEATURE:
<223> OTHER INFORMATION: Description of Unknown: bLF exemplary
      membrane penetrating peptide

<400> SEQUENCE: 47

Pro Glu Trp Phe Lys Cys Arg Arg Trp Gln Trp Arg Met Lys Lys Leu
1               5                   10                  15

Gly Ala

<210> SEQ ID NO 48
<211> LENGTH: 22
<212> TYPE: PRT
<213> ORGANISM: Unknown
<220> FEATURE:
<223> OTHER INFORMATION: Description of Unknown: bLF2 exemplary
      membrane penetrating peptide

<400> SEQUENCE: 48

Lys Cys Arg Arg Trp Gln Trp Arg Met Lys Lys Leu Gly Ala Pro Ser
1               5                   10                  15

Ile Thr Cys Val Arg Arg
            20

<210> SEQ ID NO 49
<211> LENGTH: 18
<212> TYPE: PRT
<213> ORGANISM: Unknown
<220> FEATURE:
<223> OTHER INFORMATION: Description of Unknown: bLF3 exemplary
      membrane penetrating peptide

<400> SEQUENCE: 49

Cys Arg Arg Trp Gln Trp Arg Met Lys Lys Leu Gly Ala Pro Ser Ile
1               5                   10                  15

Thr Cys

<210> SEQ ID NO 50
```

```
<211> LENGTH: 16
<212> TYPE: PRT
<213> ORGANISM: Unknown
<220> FEATURE:
<223> OTHER INFORMATION: Description of Unknown: LF1 exemplary
      membrane penetrating peptide

<400> SEQUENCE: 50

Phe Gln Trp Gln Arg Asn Met Arg Lys Val Arg Gly Pro Pro Val Ser
1               5                   10                  15

<210> SEQ ID NO 51
<211> LENGTH: 11
<212> TYPE: PRT
<213> ORGANISM: Unknown
<220> FEATURE:
<223> OTHER INFORMATION: Description of Unknown: LF2 exemplary
      membrane penetrating peptide

<400> SEQUENCE: 51

Phe Gln Trp Gln Arg Asn Met Arg Lys Val Arg
1               5                   10

<210> SEQ ID NO 52
<211> LENGTH: 18
<212> TYPE: PRT
<213> ORGANISM: Unknown
<220> FEATURE:
<223> OTHER INFORMATION: Description of Unknown: SynB1 exemplary
      membrane penetrating peptide

<400> SEQUENCE: 52

Arg Gly Gly Arg Leu Ser Tyr Ser Arg Arg Arg Phe Ser Thr Ser Thr
1               5                   10                  15

Gly Arg

<210> SEQ ID NO 53
<211> LENGTH: 15
<212> TYPE: PRT
<213> ORGANISM: Unknown
<220> FEATURE:
<223> OTHER INFORMATION: Description of Unknown: Penetratin PTD
      exemplary membrane penetrating peptide

<400> SEQUENCE: 53

Arg Gln Ile Lys Trp Phe Gln Asn Arg Arg Met Lys Trp Lys Lys
1               5                   10                  15

<210> SEQ ID NO 54
<211> LENGTH: 12
<212> TYPE: PRT
<213> ORGANISM: Unknown
<220> FEATURE:
<223> OTHER INFORMATION: Description of Unknown: PTD-4 exemplary
      membrane penetrating peptide

<400> SEQUENCE: 54

Pro Ile Arg Arg Arg Lys Lys Leu Arg Arg Leu Lys
1               5                   10

<210> SEQ ID NO 55
<211> LENGTH: 12
<212> TYPE: PRT
<213> ORGANISM: Unknown
<220> FEATURE:
<223> OTHER INFORMATION: Description of Unknown: PTD-5 exemplary
      membrane penetrating peptide
```

```
<400> SEQUENCE: 55

Arg Arg Gln Arg Arg Thr Ser Lys Leu Met Lys Arg
1               5                   10

<210> SEQ ID NO 56
<211> LENGTH: 15
<212> TYPE: PRT
<213> ORGANISM: Unknown
<220> FEATURE:
<223> OTHER INFORMATION: Description of Unknown: FHV Coat-(35-49)
      exemplary membrane penetrating peptide

<400> SEQUENCE: 56

Arg Arg Arg Arg Asn Arg Thr Arg Arg Asn Arg Arg Arg Val Arg
1               5                   10                  15

<210> SEQ ID NO 57
<211> LENGTH: 19
<212> TYPE: PRT
<213> ORGANISM: Unknown
<220> FEATURE:
<223> OTHER INFORMATION: Description of Unknown: BMV Gag-(7-25)
      exemplary membrane penetrating peptide

<400> SEQUENCE: 57

Lys Met Thr Arg Ala Gln Arg Arg Ala Ala Ala Arg Arg Asn Arg Trp
1               5                   10                  15

Thr Ala Arg

<210> SEQ ID NO 58
<211> LENGTH: 13
<212> TYPE: PRT
<213> ORGANISM: Unknown
<220> FEATURE:
<223> OTHER INFORMATION: Description of Unknown: HTLV-II Rex-(4-16)
      exemplary membrane penetrating peptide

<400> SEQUENCE: 58

Thr Arg Arg Gln Arg Thr Arg Arg Ala Arg Arg Asn Arg
1               5                   10

<210> SEQ ID NO 59
<211> LENGTH: 13
<212> TYPE: PRT
<213> ORGANISM: Unknown
<220> FEATURE:
<223> OTHER INFORMATION: Description of Unknown: D-Tat exemplary
      membrane penetrating peptide

<400> SEQUENCE: 59

Gly Arg Lys Lys Arg Arg Gln Arg Arg Arg Pro Pro Gln
1               5                   10

<210> SEQ ID NO 60
<211> LENGTH: 13
<212> TYPE: PRT
<213> ORGANISM: Unknown
<220> FEATURE:
<223> OTHER INFORMATION: Description of Unknown: R9-Tat exemplary
      membrane penetrating peptide

<400> SEQUENCE: 60

Gly Arg Arg Arg Arg Arg Arg Arg Arg Arg Pro Pro Gln
1               5                   10

<210> SEQ ID NO 61
```

```
<211> LENGTH: 27
<212> TYPE: PRT
<213> ORGANISM: Unknown
<220> FEATURE:
<223> OTHER INFORMATION: Description of Unknown: Transportan exemplary
      membrane penetrating peptide

<400> SEQUENCE: 61

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 62
<211> LENGTH: 17
<212> TYPE: PRT
<213> ORGANISM: Unknown
<220> FEATURE:
<223> OTHER INFORMATION: Description of Unknown: MAP exemplary
      membrane penetrating peptide

<400> SEQUENCE: 62

Lys Leu Ala Leu Lys Leu Ala Leu Lys Leu Ala Leu Ala Leu Lys Leu
1               5                   10                  15

Ala

<210> SEQ ID NO 63
<211> LENGTH: 27
<212> TYPE: PRT
<213> ORGANISM: Unknown
<220> FEATURE:
<223> OTHER INFORMATION: Description of Unknown: SBP exemplary
      membrane penetrating peptide

<400> SEQUENCE: 63

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 64
<211> LENGTH: 27
<212> TYPE: PRT
<213> ORGANISM: Unknown
<220> FEATURE:
<223> OTHER INFORMATION: Description of Unknown: FBP exemplary
      membrane penetrating peptide

<400> SEQUENCE: 64

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 65
<211> LENGTH: 27
<212> TYPE: PRT
<213> ORGANISM: Unknown
<220> FEATURE:
<223> OTHER INFORMATION: Description of Unknown: MPG exemplary
      membrane penetrating peptide

<400> SEQUENCE: 65

Gly Ala Leu Phe Leu Gly Phe Leu Gly Ala Ala Gly Ser Thr Met Gly
1               5                   10                  15
```

```
Ala Trp Ser Gln Pro Lys Lys Arg Lys Val
            20                  25

<210> SEQ ID NO 66
<211> LENGTH: 27
<212> TYPE: PRT
<213> ORGANISM: Unknown
<220> FEATURE:
<223> OTHER INFORMATION: Description of Unknown: MPG(deltaNLS) exemplary
      membrane penetrating peptide

<400> SEQUENCE: 66

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 67
<211> LENGTH: 21
<212> TYPE: PRT
<213> ORGANISM: Unknown
<220> FEATURE:
<223> OTHER INFORMATION: Description of Unknown: Pep-1 exemplary
      membrane penetrating peptide

<400> SEQUENCE: 67

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 68
<211> LENGTH: 21
<212> TYPE: PRT
<213> ORGANISM: Unknown
<220> FEATURE:
<223> OTHER INFORMATION: Description of Unknown: Pep-2 exemplary
      membrane penetrating peptide

<400> SEQUENCE: 68

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Ser Gly Gly Gly Ser Gly Gly Gly Ser
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70
```

```
Gly Gly Ser Gly Gly Ser Gly Gly Ser Gly Gly Ser
1               5                   10
```

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Gly Gly Gly Gly Gly Gly Gly Gly Gly Gly Gly Gly
1               5                   10
```

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Gly Gly Gly Ser Gly Gly Gly Ser Gly Gly Ser Gly Gly Gly Ser
1               5                   10                  15
```

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Gly Gly Gly Ala Gly Gly Gly Ala Gly Gly Gly Ala Gly Gly Gly Ala
1               5                   10                  15
```

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Gly Gly Gly Ala Gly Gly Gly Ser Gly Gly Gly Ala Gly Gly Gly Ser
1               5                   10                  15
```

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Ala Ala Ala Ala Ala Ala Ala Ala Ala Ala Ala
1               5                   10
```

<210> SEQ ID NO 76
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 76

Ala Ala Ala Ser Ala Ala Ala Ser Ala Ala Ala Ser
1               5                   10

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ala Ala Ser Ala Ala Ala Ser Ala Ala Ala Ser Ala Ala Ala Ser
1               5                   10                  15

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Ala Gly Ser Ala Ala Gly Ser Ala Ala Gly Ser
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Gly Gly Ser Ala Gly Gly Ser Ala Gly Gly Ser
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Gly Thr Gly Gly Gly Thr Gly Gly Gly Thr
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Ala Ala Thr Ala Ala Ala Thr Ala Ala Ala Thr
1               5                   10
```

```
<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Arg Arg Arg Arg Arg Arg Arg Arg Arg Arg
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Arg Arg Arg Arg Arg Arg Arg Arg Arg Arg Arg Arg Arg Arg Arg
1               5                   10                  15

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Arg Arg Arg Arg Arg Arg Arg Arg Arg Arg Arg Arg Arg Arg Arg
1               5                   10                  15

Arg Arg Arg Arg Arg Arg
            20

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Lys Lys Lys Lys Lys Lys Lys Lys Lys Lys
1               5                   10

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Arg Arg Arg His Arg Arg Arg Arg His Arg Arg Arg Arg His
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 87

Arg Arg Arg Arg Lys Arg Arg Arg Lys Arg Arg Arg Lys
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Lys Lys Lys Arg Lys Lys Lys Lys Arg Lys Lys Lys Lys Arg
1               5                   10                  15

<210> SEQ ID NO 89
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ser Arg Arg Ala Arg Arg Ser Pro Arg Glu Ser Gly Lys Lys Arg Lys
1               5                   10                  15

Arg Lys Arg Gly Gly Gly Ser Gly Gly Gly Ser Gly Gly Gly Ser Arg
                20                  25                  30

Arg Arg Arg Arg Arg Arg Arg Arg Arg Arg
            35                  40

<210> SEQ ID NO 90
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Cys Gly Ala Tyr Asp Leu Arg Arg Arg Glu Arg Gln Ser Arg Leu Arg
1               5                   10                  15

Arg Arg Glu Arg Gln Ser Arg Gly Gly Gly Ser Gly Gly Gly Ser Gly
                20                  25                  30

Gly Gly Ser Arg Arg Arg Arg Arg Arg Arg Arg Arg Arg Arg
            35                  40                  45

<210> SEQ ID NO 91
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Tyr Gly Arg Lys Lys Arg Arg Gly Arg Arg Thr His Arg Leu
1               5                   10                  15

Pro Gly Gly Gly Ser Gly Gly Gly Ser Gly Gly Gly Ser Arg Arg Arg
                20                  25                  30

Arg Arg Arg Arg Arg Arg Arg
```

```
                35                  40

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ile Gly Cys Arg His Gly Gly Ser Gly Gly Ser Gly Gly
1               5                   10                  15

Ser Arg Arg Arg Arg Arg Arg Arg Arg Arg
        20                  25

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Cys Gly Asn Lys Arg Thr Arg Gly Cys Gly Gly Ser Gly Gly
1               5                   10                  15

Ser Gly Gly Gly Ser Arg Arg Arg Arg Arg Arg Arg Arg Arg
        20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Cys Ala Gly Arg Arg Ser Ala Tyr Cys Gly Gly Ser Gly Gly
1               5                   10                  15

Ser Gly Gly Gly Ser Arg Arg Arg Arg Arg Arg Arg Arg Arg
        20                  25                  30

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Ser Gly Lys Lys Gly Gly Lys Lys His Cys Gln Lys Tyr Gly Gly
1               5                   10                  15

Gly Ser Gly Gly Gly Ser Gly Gly Gly Ser Arg Arg Arg Arg Arg
        20                  25                  30

Arg Arg Arg Arg Arg
        35

<210> SEQ ID NO 96
<211> LENGTH: 37
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 96

Tyr Lys Gln Cys His Lys Lys Gly Gly Lys Lys Gly Ser Gly Gly
1               5                   10                  15

Gly Ser Gly Gly Gly Ser Gly Gly Gly Ser Arg Arg Arg Arg Arg
                20                  25                  30

Arg Arg Arg Arg Arg
            35

<210> SEQ ID NO 97
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Lys Met Thr Arg Ala Gln Arg Arg Ala Ala Arg Arg Asn Arg Trp
1               5                   10                  15

Thr Ala Arg Gly Cys Gly Gly Ser Gly Gly Gly Ser Gly Gly Gly
                20                  25                  30

Ser Arg Arg Arg Arg Arg Arg Arg Arg Arg Arg
            35                  40

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Arg Arg His His Cys Arg Ser Lys Ala Lys Arg Ser Arg His His Gly
1               5                   10                  15

Gly Gly Ser Gly Gly Gly Ser Gly Gly Gly Ser Arg Arg Arg Arg
                20                  25                  30

Arg Arg Arg Arg Arg Arg
            35

<210> SEQ ID NO 99
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Lys Cys Phe Gln Trp Gln Arg Asn Met Arg Lys Val Arg Gly Pro Pro
1               5                   10                  15

Val Ser Cys Ile Lys Arg Gly Gly Gly Ser Gly Gly Gly Ser Gly Gly
                20                  25                  30

Gly Ser Arg Arg Arg Arg Arg Arg Arg Arg Arg Arg
            35                  40                  45

<210> SEQ ID NO 100
<211> LENGTH: 41
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 100

Pro Glu Trp Phe Lys Cys Arg Arg Trp Gln Trp Arg Met Lys Lys Leu
1               5                   10                  15

Gly Ala Gly Gly Ser Gly Gly Ser Gly Gly Ser Gly Gly Ser Lys Lys
                20                  25                  30

Lys Lys Lys Lys Lys Lys Lys
            35                  40

<210> SEQ ID NO 101

<400> SEQUENCE: 101

000

<210> SEQ ID NO 102
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Lys Cys Phe Gln Trp Gln Arg Asn Val Arg Lys Val Arg Gly Pro Pro
1               5                   10                  15

Val Ser Cys Ile Lys Arg Ala Ala Gly Ser Ala Ala Gly Ser Ala Ala
                20                  25                  30

Gly Ser Lys Lys Lys Lys Arg Lys Lys Lys Arg Lys Lys Lys Lys
            35                  40                  45

Arg

<210> SEQ ID NO 103
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Arg Arg His His Cys Arg Ser Lys Ala Lys Arg Ser Arg His His
1               5                   10                  15

Gly Gly Gly Ser Gly Gly Gly Ser Gly Gly Gly Ser Arg Arg Arg Arg
                20                  25                  30

Arg Arg Arg Arg Arg Arg Arg
            35

<210> SEQ ID NO 104
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Cys Gly Asn Lys Arg Thr Arg Gly Cys Gly Gly Gly Gly Gly Gly Gly
1               5                   10                  15

Gly Gly Arg Arg Arg Arg Lys Arg Arg Arg Lys Arg Arg Arg Arg
```

```
                20                  25                  30

Lys

<210> SEQ ID NO 105
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Cys Arg Arg Trp Gln Trp Arg Met Lys Lys Leu Gly Ala Pro Ser
1               5                   10                  15

Ile Thr Cys Val Arg Arg
            20

<210> SEQ ID NO 106
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Cys Tyr Gly Arg Lys Lys Arg Arg Gln Arg Arg Arg Arg Arg Arg Arg
1               5                   10                  15

Arg Arg Arg Arg Arg Arg Arg Arg Arg Arg Arg Arg Arg Arg Arg Arg
            20                  25                  30

Arg Arg

<210> SEQ ID NO 107
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Arg Gln Ile Lys Trp Phe Gln Asn Arg Arg Met Lys Trp Lys Lys Ala
1               5                   10                  15

Ala Ser Ala Ala Ala Ser Ala Ala Ala Ser Arg Arg Arg Lys Lys
            20                  25                  30

Lys Arg Arg Arg Lys Lys Lys
        35

<210> SEQ ID NO 108
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Ser Gly Gly Gly Ser Gly Gly Gly Ser Arg Arg Arg Arg
1               5                   10                  15

Arg Arg Arg Arg Arg Arg Arg
            20

<210> SEQ ID NO 109
```

-continued

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 5 to 20 "Arg"
      residues, wherein some positions may be absent

<400> SEQUENCE: 109

Arg Arg Arg Arg Arg Arg Arg Arg Arg Arg Arg Arg Arg Arg Arg Arg
1               5                   10                  15

Arg Arg Arg Arg
            20
```

UNITED STATES PATENT AND TRADEMARK OFFICE
CERTIFICATE OF CORRECTION

| | |
|---|---|
| PATENT NO. | : 12,152,248 B2 |
| APPLICATION NO. | : 17/006629 |
| DATED | : November 26, 2024 |
| INVENTOR(S) | : Xavier de Mollerat du Jeu |

Page 1 of 1

It is certified that error appears in the above-identified patent and that said Letters Patent is hereby corrected as shown below:

On the Title Page

In Column 1, under Related U.S. Application Data, Line 1, delete "(60)" and insert -- (63) --, therefor.

In the Claims

In Column 114, Claim 16, Line 42, delete "N-trimethylamonium" and insert
-- N-trimethylammonium --, therefor.

In Column 114, Claim 16, Line 43, delete "(DOPE)" and insert -- (DOPC) --, therefor.

In Column 114, Claim 16, Line 44, delete "ammonio)" and insert -- ammonium) --, therefor.

In Column 114, Claim 16, Line 45, delete "trimethylammonio)" and insert -- trimethylammonium) --, therefor.

In Column 114, Claim 16, Line 49, delete "trimethylammonio)" and insert -- trimethylammonium) --, therefor.

In Column 114, Claim 16, Line 60, delete "dipalmitoylphasphatidylethanolamine" and insert
-- dipalmitoylphosphatidylethanolamine --, therefor.

In Column 114, Claim 16, Line 65, delete "[N--(N'," and insert -- [N-(N', --, therefor.

Signed and Sealed this
Twenty-first Day of January, 2025

Coke Morgan Stewart
*Acting Director of the United States Patent and Trademark Office*